United States Patent
Tange et al.

(10) Patent No.: US 9,708,628 B2
(45) Date of Patent: Jul. 18, 2017

(54) CATIONIC LIPID HAVING IMPROVED INTRACELLULAR KINETICS

(71) Applicants: NOF CORPORATION, Tokyo (JP); NATIONAL UNIVERSITY CORPORATION HOKKAIDO UNIVERSITY, Sapporo-shi, Hokkaido (JP)

(72) Inventors: Kota Tange, Kawasaki (JP); Masaya Arai, Kawasaki (JP); Kazuhiro Kubo, Kawasaki (JP); Hidetaka Akita, Sapporo (JP); Hideyoshi Harashima, Sapporo (JP); Hiroto Hatakeyama, Sapporo (JP); Ryohei Ishiba, Sapporo (JP); Masami Ukawa, Sapporo (JP); Hiroki Tanaka, Sapporo (JP)

(73) Assignees: NOF Corporation, Tokyo (JP); National University Corporation Hokkaido University, Sapporo (JP)

( * ) Notice: Subject to any disclaimer, the term of this patent is extended or adjusted under 35 U.S.C. 154(b) by 335 days.

(21) Appl. No.: 14/280,016

(22) Filed: May 16, 2014

(65) Prior Publication Data

US 2014/0335157 A1    Nov. 13, 2014

Related U.S. Application Data

(63) Continuation-in-part of application No. PCT/JP2012/079160, filed on Nov. 9, 2012.

(30) Foreign Application Priority Data

Nov. 18, 2011    (JP) ................. 2011-252309

(51) Int. Cl.
   *A61K 47/20*    (2006.01)
   *C12N 15/88*    (2006.01)
   (Continued)

(52) U.S. Cl.
   CPC ............ *C12N 15/88* (2013.01); *A61K 9/0019* (2013.01); *A61K 9/1271* (2013.01);
   (Continued)

(58) Field of Classification Search
   CPC .... C12N 15/88; A61K 9/0019; A61K 9/1271; A61K 9/1272; A61K 47/20; A61K 47/22;
   (Continued)

(56) References Cited

U.S. PATENT DOCUMENTS

| 3,640,715 A * | 2/1972 | Huckstadt | ............. G03C 1/346 430/377 |
| 4,217,914 A * | 8/1980 | Jacquet | ................. A01N 33/12 132/202 |
| 2005/0164391 A1 | 7/2005 | Chu et al. | |

FOREIGN PATENT DOCUMENTS

| CN | 101039701 A | 9/2007 |
| DE | 25 21 898 A1 | 12/1975 |

(Continued)

OTHER PUBLICATIONS

Hama et al., *Molecular Therapy*, 13(4): 786-794 (2006).
(Continued)

*Primary Examiner* — Noble Jarrell
*Assistant Examiner* — Daniel Carcanague
(74) *Attorney, Agent, or Firm* — Leydig, Voit & Mayer, Ltd.

(57) ABSTRACT

The present invention relates to a compound represented by the formula (1)

(Continued)

wherein $X^a$ and $X^b$ are each independently $X^1$ or $X^2$;

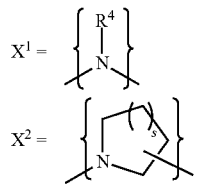

s is 1 or 2,
$R^4$ is an alkyl group having 1-6 carbon atoms,
$n^a$ and $n^b$ are each independently 0 or 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each independently an ester bond, an amide bond, a carbamate bond, an ether bond or a urea bond, and
$R^{3a}$ and $R^{3b}$ are each independently a sterol residue, a liposoluble vitamin residue or an aliphatic hydrocarbon group having 12-22 carbon atoms,
and use thereof.

20 Claims, 23 Drawing Sheets

(51) Int. Cl.
    *A61K 47/22*    (2006.01)
    *A61K 9/127*    (2006.01)
    *C07C 323/25*   (2006.01)
    *C07D 311/72*   (2006.01)
    *A61K 9/00*     (2006.01)
(52) U.S. Cl.
    CPC ............ *A61K 9/1272* (2013.01); *A61K 47/20* (2013.01); *A61K 47/22* (2013.01); *C07C 323/25* (2013.01); *C07D 311/72* (2013.01); *C07C 2101/16* (2013.01)

(58) Field of Classification Search
    CPC .. C07C 323/25; C07C 2101/16; C07D 311/72
    USPC ...................................................... 546/248
    See application file for complete search history.

(56) References Cited

FOREIGN PATENT DOCUMENTS

| | | | |
|---|---|---|---|
| DE | 2521898 A1 | * | 12/1975 |
| FR | 2921256 | * | 3/2009 |
| GB | 1 513 671 | | 6/1978 |
| JP | 2010-507680 A | | 3/2010 |
| JP | 2011-121966 A | | 6/2011 |
| WO | WO 99/58152 A1 | | 11/1999 |
| WO | WO 00/27795 A1 | | 5/2000 |
| WO | WO 01/54405 A1 | | 7/2001 |
| WO | WO 2006/027711 A2 | | 3/2006 |
| WO | WO 2008/045486 A2 | | 4/2008 |
| WO | WO 2008/147438 A2 | | 12/2008 |
| WO | WO 2010/054405 A1 | | 5/2010 |

OTHER PUBLICATIONS

Passirani et al., *Biomaterials*, 29(24-25): 3477-3496 (2008).
Wheeler et al., *Gene Therapy*, 6: 271-281 (1999).
Japanese Patent Office, International Search Report in International Patent Application No. PCT/JP2012/079160 (Feb. 19, 2013).
Akita et al., *Advanced Healthcare Materials*, 2(8): 1120-1125 (2013).
Kogure et al., *Advanced Drug Delivery Reviews*, 60(4-5): 559-571 (2007).
Quaglia et al., *Journal of Medicinal Chemistry*, 31(9): 1861-1866 (1988).
Thiel et al., *Justus Lievigs Annalen Der Chemie*, 622(1): 107-116 (1959).
European Patent Office, Supplementary European Search Report in European Patent Application No. 12850198 (Sep. 10, 2015).
Ren et al., *Bioorganic & Medicinal Chemistry Letters*, 10(9):891-894 (2000).

* cited by examiner

B-2

B-2-4

Green: Lysosome(LysotrackerGreen)   Red: pDNA(Rhodamine)

Blue: Nucleus(Hoechst33342)  Green: Lysosome(LysotrackerGreen)

Green: Lipid membrane(NBD-DOPE)   Red: pDNA(Rhodamine)

B-2　　　　　　　　B-2-4

Blue: Nucleus(Hoechst33342)　Green: Lipid membrane (NBD-DOPE)
Red: pDNA(Rhodamine)

CATIONIC LIPID HAVING IMPROVED INTRACELLULAR KINETICS

CROSS REFERENCES TO RELATED APPLICATIONS

This application is based on a patent application No. 2011-252309 filed in Japan on Nov. 18, 2011, and International Patent Application No. PCT/JP2012/079160, filed on Nov. 9, 2012, the contents of which are incorporated in full herein.

TECHNICAL FIELD OF THE INVENTION

The present invention relates to a cationic lipid having improved intracellular kinetics, a lipid membrane structure containing same, and use thereof.

BACKGROUND OF THE INVENTION

For practicalization of nucleic acid therapy, an effective and safe nucleic acid delivery carrier is demanded. While virus vectors are nucleic acid delivery carriers with good expression efficiency, they have practical problems from the aspect of safety. Therefore, the development of non-viral nucleic acid delivery carriers that can be used more safely is ongoing. Among them, carriers using a cationic lipid are non-viral nucleic acid delivery carriers most generally used at present.

Cationic lipids are largely composed of an amine moiety and a lipid moiety, wherein the amine moiety showing cationicity and a polyanion nucleic acid electrostatically interact to form a positively-charged liposome or lipid membrane structure, which promotes uptake into cells and delivers the nucleic acid into cells.

As known cationic lipids generally and widely used, DOTAP and DODAP can be mentioned. These known cationic lipids form a positively-charged liposome or lipid membrane structure when combined with a phospholipid, which electrostatically interacts with a nucleic acid to be able to deliver the nucleic acid to the target cells (non-patent document 1).

Patent document 1 describes a cationic lipid containing a large amount of amino group so as to increase the amount of uptake into cells. The document argues that this cationic lipid shows high cellular uptake potency and acts on various cells having different cellular membrane compositions.

On the other hand, for a nucleic acid delivery carrier using a cationic lipid to exhibit a practical effect in vivo, the requirements of good in vivo kinetics, specifically high stability in blood, property to highly accumulate in the target such as tumor, and the like need to be fulfilled. Given the problem, Wheeler et al. showed that a lipid membrane structure containing a cationic lipid having pKa adjusted to around neutral shows a long lifetime in blood after intravenous injection, accumulates in tumor sites, and can mediate the expression of nucleic acid in the tumor sites (non-patent document 2).

While cationic lipids having improved in vivo kinetics have been developed as shown above, in view of the property of the nucleic acid delivery carriers that they generally introduce exogenous substances into cells, a large effect output from a small uptake amount is desired. That is, when a lipid membrane structure is used as a delivery carrier of an expression vector into cells, it is desired to increase the expression level per unit lipid membrane structure incorporated into the cells and enhance intracellular expression efficiency. To enhance the intracellular expression efficiency, it is necessary to also improve, besides in vivo kinetics, intracellular kinetics such as uptake process, escape from endosome and the like, nuclear membrane permeation and the like. Moreover, it is known that dissociation of nucleic acids from the carrier and enhancement of the bindability of transcription factors are necessary to facilitate intracellular transcription (non-patent document 3).

Examples of the facilitation of intracellular dissociation of nucleic acid from a lipid membrane structure include a compound wherein one amine moiety and two lipid moieties are bonded via disulfide (patent document 2) and a compound wherein one amine moiety and two lipid moieties are each bonded via a disulfide bond (patent document 3). It is described that these compounds have an effect to dissociate the nucleic acid interacting with the amine moiety from the lipid membrane structure by utilizing intracellular cleavage of the disulfide bond.

However, despite the progress in this field, the intracellular expression efficiency achieved by nucleic acid delivery carriers using conventional cationic lipid is not fully satisfactory.

DOCUMENT LIST

Patent Documents patent document 1: JP-A-2011-121966
patent document 2: WO 99/58152

Non-Patent Documents non-patent document 1: Biomaterials 29(24-25):3477-96, 2008
non-patent document 2: Gene Therapy 6:271-281, 1999
non-patent document 3: Molecular Therapy 13(4):786-794, 2006

SUMMARY OF THE INVENTION

Problems to be Solved by the Invention

In view of the property of the nucleic acid delivery carriers using cationic lipid that they introduce exogenous substances into cells, they are demanded to exhibit a large effect from a small uptake amount, namely, to increase the expression level per unit lipid membrane structure incorporated in cells, and enhance intracellular expression efficiency. An object of the present invention is to provide a cationic lipid capable of achieving high intracellular expression efficiency when used as a nucleic acid delivery carrier.

Means of Solving the Problems

In view of the above-mentioned problems, the present inventors have conducted intensive studies and found that the compound of patent document 2 maintains a structure having two lipid moieties even after cleavage of disulfide bond and, as a result, the lipid membrane structure does not collapse in the cell, and the encapsulate compound such as nucleic acid and the like is not efficiently released into the cytoplasm. When the compound of patent document 2 is used for nucleic acid introduction, moreover, nucleic acid is released into the cell while being interactive with an amine moiety, which possibly prevents a transcription factor from accessing and binding to the nucleic acid.

Furthermore, when the compounds of patent documents 2 and 3 are used, the produced residues are divided into the amine moiety, which is a polar group, and the lipid moiety, which is a non-polar group, upon intracellular cleavage of the disulfide bond, thus losing its surface activity. While the disappearance of such surface activity is advantageous for inducing the collapse of an intracellular lipid membrane structure, it does not allow expectation of destabilization of endosome membrane and an endosomal escape promoting effect associated therewith.

Taking note of such new technical problems, further studies have been made. As a result, they have found that these problems can be solved by binding an amine moiety and a lipid moiety in a stable binding manner resistant to intracellular cleavage and binding two molecules of the obtained surfactant via a disulfide bond, instead of binding the amine moiety and the lipid moiety via a disulfide bond, which resulted in the completion of the present invention.

Accordingly, the present invention encompasses the following.

[1] A compound represented by the formula (1)

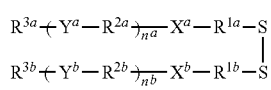

wherein $X^a$ and $X^b$ are each independently $X^1$ or $X^2$;

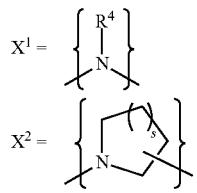

s is 1 or 2,
$R^4$ is an alkyl group having 1-6 carbon atoms,
$n^a$ and $n^b$ are each independently 0 or 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each independently an ester bond, an amide bond, a carbamate bond, an ether bond or a urea bond, and
$R^{3a}$ and $R^{3b}$ are each independently a sterol residue, a liposoluble vitamin residue or an aliphatic hydrocarbon group having 12-22 carbon atoms.
[2] The compound of [1], wherein $X^a$ and $X^b$ are each independently $X^1$.
[3] The compound of [1], wherein $X^a$ and $X^b$ are each independently $X^2$.
[4] The compound of any of [1] to [3], wherein $R^{3a}$ and $R^{3b}$ are each independently a liposoluble vitamin residue or an aliphatic hydrocarbon group having 12-22 carbon atoms.
[5] The compound of any of [1] to [4], wherein $R^{3a}$ and $R^{3b}$ are each independently a liposoluble vitamin residue.
[6] The compound of any of [1] to [4], wherein $R^{3a}$ and $R^{3b}$ are each independently an aliphatic hydrocarbon group having 12-22 carbon atoms.
[7] A lipid membrane structure comprising the compound of any of [1] to [6] as a membrane-constituting lipid.

[8] An agent for introducing a nucleic acid, comprising the compound of any of [1] to [6] or the lipid membrane structure of [7].
[9] A method of introducing a nucleic acid into a cell, comprising contacting the lipid membrane structure of [7], which encapsulates the nucleic acid, with the cell.
[10] A method of introducing a nucleic acid into a cell, comprising administering the lipid membrane structure of [9], which encapsulates the nucleic acid, to a living organism so that it will be delivered to the target cell.

Effect of the Invention

The present invention relates to a compound having two tertiary amino groups and two lipid moieties, and a disulfide bond which is a biodegradable group, and a lipid membrane structure containing the compound. The compound of the present invention can form a stable lipid membrane structure such as liposome and the like, and can adjust pKa of the lipid membrane structure to near neutral. Moreover, when transgene is performed using the cationic lipid of the present invention, the disulfide bond contained in the cationic lipid of the present invention is cleaved in the intracellular reductive environment, and release of the encapsulated substance (nucleic acid) is promoted due to the destabilization of the lipid membrane structure. Therefore, not only intracellular expression efficiency of the delivered gene, namely, intracellular expression efficiency per unit lipid membrane structure incorporated in cells, can be enhanced, but also efficient gene knockdown via the delivered nucleic acid can be achieved.

When transgene is performed using the compound of the present invention, or a lipid membrane structure containing the same, degradation of the nucleic acid by the serum components is suppressed, which is advantageous for transgene in the presence of serum or transgene in vivo.

DESCRIPTION OF EMBODIMENTS

Figure 1:
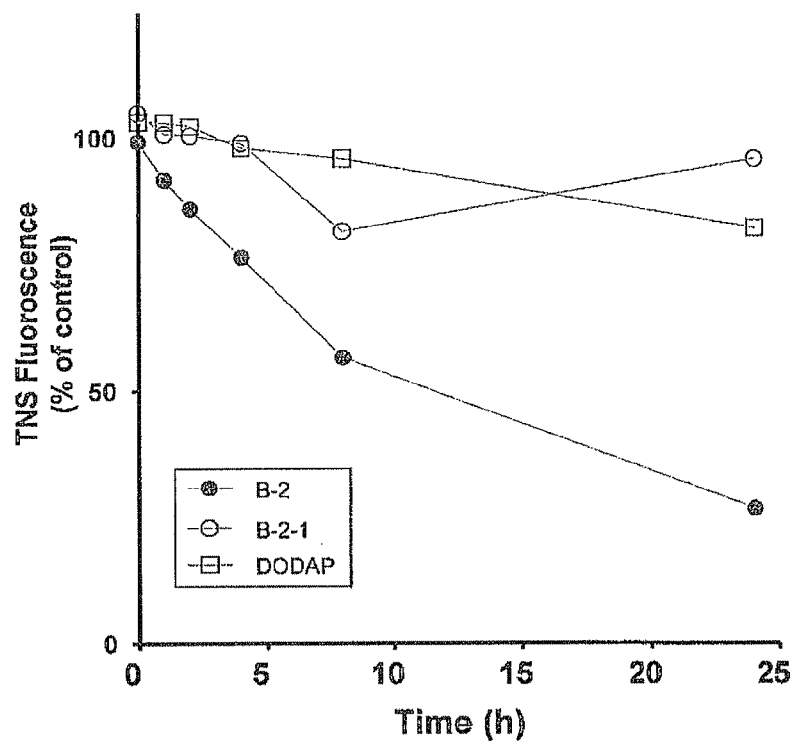
FIG. 1 shows the destabilization property of various lipid membranes in the presence of a reducing agent.

While the embodiments of the present invention are explained in the following, the present invention is not limited thereto.

The present invention provides a compound represented by the formula (1).

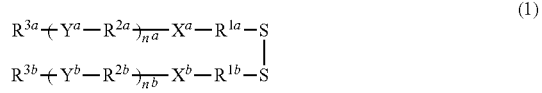

In the formula (1), $X^a$ and $X^b$ are each independently $X^1$ or $X^2$ shown below.

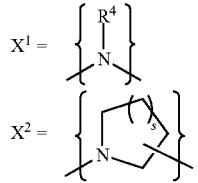

$R^4$ in $X^1$ is an alkyl group having 1-6 carbon atoms, which may be linear, branched or cyclic. The alkyl group preferably has a carbon number of 1-3. Specific examples of the alkyl group having 1-6 carbon atoms include methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like. $R^4$ is preferably a methyl group, an ethyl group, a propyl group or an isopropyl group, most preferably a methyl group.

The s in $X^2$ is 1 or 2. When s is 1, $X^2$ is a pyrrolidinium group, and when s is 2, $X^2$ is a piperidinium group. s is preferably 2. While the binding direction of $X^2$ is not limited, a nitrogen atom in $X^2$ preferably binds to $R^{1a}$ and $R^{1b}$.

$X^a$ may be the same as or different from $X^b$, and $X^a$ is preferably the same group as $X^b$.

$n^a$ and $n^b$ are each independently 0 or 1, preferably 1. When $n^a$ is 1, $R^{3a}$ binds to $X^a$ via $Y^a$ and $R^{2a}$, and when $n^a$ is 0, a structure of $R^{3a}$—$X^a$—$R^{1a}$—S— is taken. Similarly, when $n^b$ is 1, $R^{3b}$ binds to $X^b$ via $Y^b$ and $R^{2b}$, and when $n^b$ is 0, a structure of $R^{3b}$—$X^b$—$R^{1b}$—S— is taken.

$n^a$ may be the same as or different from $n^b$, and $n^a$ is preferably the same as $n^b$.

$R^{1a}$ and $R^{1b}$ are each independently an alkylene group having 1-6 carbon atoms, which may be linear or branched, preferably linear. Specific examples of the alkylene group having 1-6 carbon atoms include methylene group, ethylene group, trimethylene group, isopropylene group, tetramethylene group, isobutylene group, pentamethylene group, neopentylene group and the like. $R^{1a}$ and $R^{1b}$ are each preferably a methylene group, an ethylene group, a trimethylene group, an isopropylene group or a tetramethylene group, most preferably an ethylene group.

$R^{1a}$ may be the same as or different from $R^{1b}$, and $R^{1a}$ is preferably the same group as $R^{1b}$.

$R^{2a}$ and $R^{2b}$ are each independently an alkylene group having 1-6 carbon atoms, which may be linear or branched, preferably linear. Examples of the alkylene group having 1-6 carbon atoms include those recited as the examples of the alkylene group having 1-6 carbon atoms for $R^{1a}$ or $R^{1b}$. $R^{2a}$ and $R^{2b}$ are each preferably a methylene group, an ethylene group, a trimethylene group, an isopropylene group or a tetramethylene group.

When $X^a$ and $X^b$ are each $X^1$, $R^{2a}$ and $R^{2b}$ are preferably trimethylene groups. When $X^a$ and $X^b$ are each $X^2$, $R^{2a}$ and $R^{2b}$ are preferably ethylene groups.

$R^{2a}$ may be the same as or different from $R^{2b}$, and $R^{2a}$ is preferably the same group as $R^{2b}$.

$Y^a$ and $Y^b$ are each independently an ester bond, an amide bond, a carbamate bond, an ether bond or a urea bond, preferably an ester bond, an amide bond or a carbamate bond, most preferably an ester bond. While the binding direction of $Y^a$ and $Y^b$ is not limited, when $Y^a$ is an ester bond, a structure of $R^{3a}$—CO—O—$R^{2a}$— is preferable, and when $Y^b$ is an ester bond, a structure of $R^{3b}$—CO—O—$R^{2b}$— is preferable.

$Y^a$ may be the same as or different from $Y^b$, and $Y^a$ is preferably the same group as $Y^b$.

$R^{3a}$ and $R^{3b}$ are each independently a sterol residue, a liposoluble vitamin residue or an aliphatic hydrocarbon group having 12-22 carbon atoms, preferably a liposoluble vitamin residue or an aliphatic hydrocarbon group having 12-22 carbon atoms, most preferably a liposoluble vitamin residue.

Examples of the sterol residue include a cholesteryl group (cholesterol residue), a cholestaryl group (cholestanol residue), a stigmasteryl group (stigmasterol residue), a β-sitosteryl group (β-sitosterol residue), a lanosteryl group (lanosterol residue), and an ergosteryl group (ergosterol residue) and the like. The sterol residue is preferably a cholesteryl group or a cholestaryl group.

As the liposoluble vitamin residue, a residue derived from liposoluble vitamin, as well as a residue derived from a derivative obtained by appropriately converting a hydroxyl group, aldehyde or carboxylic acid, which is a functional group in liposoluble vitamin, to other reactive functional group can be used. As for liposoluble vitamin having a hydroxyl group, for example, the hydroxyl group can be converted to a carboxylic acid by reacting with succinic acid anhydride, glutaric acid anhydride and the like. Examples of the liposoluble vitamin include retinoic acid, retinol, retinal, ergosterol, 7-dehydrocholesterol, calciferol, cholecalciferol, dihydroergocalciferol, dihydrotachysterol, tocopherol, tocotrienol and the like. Preferable examples of the liposoluble vitamin include retinoic acid and tocopherol.

The aliphatic hydrocarbon group having 12-22 carbon atoms may be linear or branched, preferably linear. The aliphatic hydrocarbon group may be saturated or unsaturated. In the case of an unsaturated aliphatic hydrocarbon group, the aliphatic hydrocarbon group generally contains 1-6, preferably 1-3, more preferably 1-2 unsaturated bonds. While the unsaturated bond includes a carbon-carbon double bond and a carbon-carbon triple bond, it is preferably a carbon-carbon double bond. The aliphatic hydrocarbon group has a carbon number of preferably 12-18, most preferably 13-17. While the aliphatic hydrocarbon group includes an alkyl group, an alkenyl group, an alkynyl group and the like, it is preferably an alkyl group or an alkenyl group. Specific examples of the aliphatic hydrocarbon group having 12-22 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, decadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group and the like. The aliphatic hydrocarbon group having 12-22 carbon atoms is preferably tridecyl group, tetradecyl group, heptadecyl group, octadecyl group, heptadecadienyl group or octadecadienyl group, particularly preferably tridecyl group, heptadecyl group or heptadecadienyl group.

In one embodiment, an aliphatic hydrocarbon group having 12-22 carbon atoms, which is derived from fatty acid, aliphatic alcohol, or aliphatic amine is used. When $R^{3a}$ (or $R^{3b}$) is derived from fatty acid, $Y^a$ (or $Y^b$) is an ester bond or an amide bond, and fatty acid-derived carbonyl carbon is included in $Y^a$ (or $Y^b$). For example, when linoleic acid is used, $R^{3a}$ (or $R^{3b}$) is a heptadecadienyl group.

$R^{3a}$ may be the same as or different from $R^{3b}$, and $R^{3a}$ is preferably the same group as $R^{3b}$.

In one embodiment, $X^a$ is the same as $X^b$, $n^a$ is the same as $n^b$, $R^{1a}$ is the same as $R^{1b}$, $R^{2a}$ is the same as $R^{2b}$, $R^{3a}$ is the same as $R^{3b}$, and $Y^a$ is the same as $Y^b$.

In one embodiment,
$X^a$ and $X^b$ are each independently $X^1$,
$R^4$ is an alkyl group having 1-3 carbon atoms, $n^a$ and $n^b$ are each 1,
$R^{1a}$ and $R^{1b}$ are each independently an alkylene group having 1-6 carbon atoms, $R^{2a}$ and $R^{2b}$ are each independently an alkylene group having 1-6 carbon atoms,
$Y^a$ and $Y^b$ are each an ester bond or an amide bond, and
$R^{3a}$ and $R^{3b}$ are each independently an aliphatic hydrocarbon group having 12-22 carbon atoms.

In one embodiment,
$X^a$ and $X^b$ are each $X^1$,
$R^4$ is an alkyl group having 1-3 carbon atoms, $n^a$ and $n^b$ are each 1,
$R^{1a}$ and $R^{1b}$ are each an alkylene group having 1-6 carbon atoms,
$R^{2a}$ and $R^{2b}$ are each an alkylene group having 1-6 carbon atoms,
$Y^a$ and $Y^b$ are each an ester bond or an amide bond,
$R^{3a}$ and $R^{3b}$ are each an aliphatic hydrocarbon group having 12-22 carbon atoms,
$X^a$ is the same as $X^b$,
$R^{1a}$ is the same as $R^{1b}$,
$R^{2a}$ is the same as $R^{2b}$, and
$R^{3a}$ is the same as $R^{3b}$.

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—, and
$R^{3a}$ and $R^{3b}$ are each independently an alkyl group or alkenyl group having 13-17 carbon atoms.

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—,
$R^{3a}$ and $R^{3b}$ are each an alkyl group or alkenyl group having 13-17 carbon atoms, and
$R^{3a}$ is the same as $R^{3b}$.

In one embodiment,
$X^a$ and $X^b$ are each independently $X^1$,
$R^4$ is an alkyl group having 1-3 carbon atoms, $n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond or an amide bond, and
$R^{3a}$ and $R^{3b}$ are each independently a liposoluble vitamin residue (e.g., retinoic acid residue, tocopherol residue).

In one embodiment,
$X^a$ and $X^b$ are each $X^1$,
$R^4$ is an alkyl group having 1-3 carbon atoms, $n^a$ and $n^b$ are each 1,
$R^{1a}$ and $R^{1b}$ are each an alkylene group having 1-6 carbon atoms,
$R^{2a}$ and $R^{2b}$ are each an alkylene group having 1-6 carbon atoms,
$Y^a$ and $Y^b$ are each an ester bond or an amide bond,
$R^{3a}$ and $R^{3b}$ are each a liposoluble vitamin residue (e.g., retinoic acid residue, tocopherol residue),
$X^a$ is the same as $X^b$,
$R^{1a}$ is the same as $R^{1b}$,
$R^{2a}$ is the same as $R^{2b}$, and
$R^{3a}$ is the same as $R^{3b}$.

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—, and
$R^{3a}$ and $R^{3b}$ are each independently a liposoluble vitamin residue (e.g., retinoic acid residue, tocopherol residue).

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—,
$R^{3a}$ and $R^{3b}$ are each a liposoluble vitamin residue (e.g., retinoic acid residue, tocopherol residue), and
$R^{3a}$ is the same as $R^{3b}$.

In one embodiment,
$X^a$ and $X^b$ are each independently $X^2$,
t is 2,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond, and
$R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms).

In one embodiment,
$X^a$ and $X^b$ are each independently $X^2$,
t is 2,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond,
$R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms),
$X^a$ is the same as $X^b$,
$R^{1a}$ is the same as $R^{1b}$,
$R^{2a}$ is the same as $R^{2b}$, and
$R^{3a}$ is the same as $R^{3b}$.

In one embodiment,
$X^a$ and $X^b$ are each independently $X^2$,
t is 2,
$R^{1a}$ and $R^{1b}$ are each an ethylene group,
$R^{2a}$ and $R^{2b}$ are each independently an alkylene group having 1-6 carbon atoms,
$Y^a$ and $Y^b$ are each an ester bond,
$R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms),
$X^a$ is the same as $X^b$,
$R^{2a}$ is the same as $R^{2b}$, and
$R^{3a}$ is the same as $R^{3b}$.

Specific examples of the compound of the present invention include the compounds of the following B-2, B-2-2, B-2-3, B-2-4, B-2-5, TS-C4E, TS-C5P, TS-P2C1, TS-P3C1, TS-P4C1, TS-P4C2, TS-P4C3, TS-P4C4, TG-C3M and TSamide-C3M.

TABLE 1

| compound name | structure |
|---|---|
| B-2 | 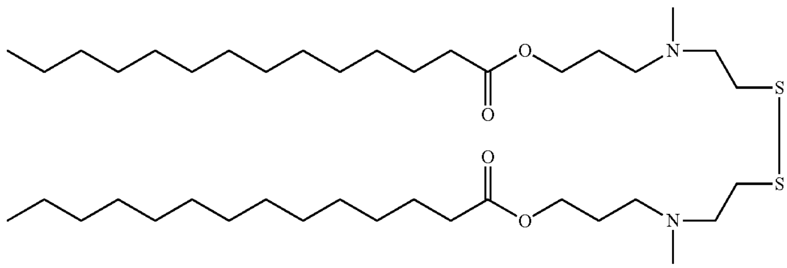 [SMILES: CCCCCCCCCCCCCC(=O)OCCCN(C)CCSSCCN(C)CCCOC(=O)CCCCCCCCCCCCC] |
| B-2-2 | 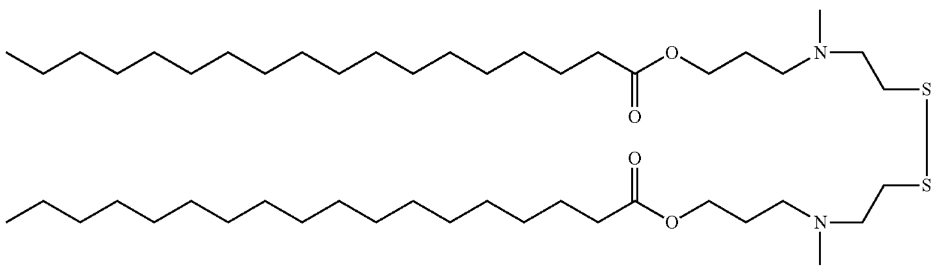 [SMILES: CCCCCCCCCCCCCCCCCC(=O)OCCCN(C)CCSSCCN(C)CCCOC(=O)CCCCCCCCCCCCCCCCC] |
| B-2-3 | 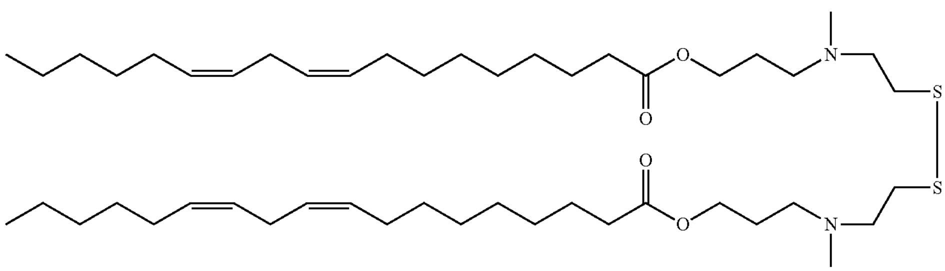 [SMILES: CCCCC/C=C\C/C=C\CCCCCCCC(=O)OCCCN(C)CCSSCCN(C)CCCOC(=O)CCCCCCC/C=C\C/C=C\CCCCC] |
| B-2-4 | 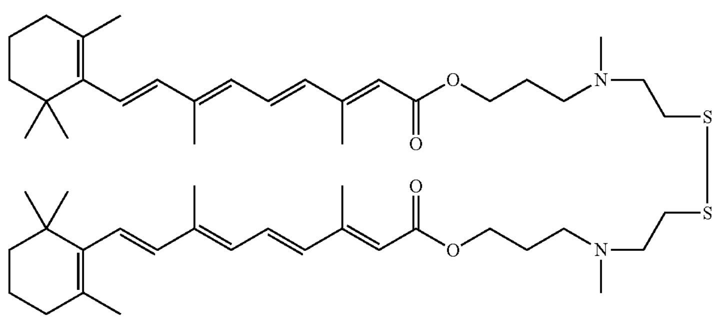 [SMILES: CC1=C(/C=C/C(C)=C/C=C/C(C)=C/C(=O)OCCCN(C)CCSSCCN(C)CCCOC(=O)/C=C(C)/C=C/C=C(C)/C=C/C2=C(C)CCCC2(C)C)C(C)(C)CCC1] |
| B-2-5 | 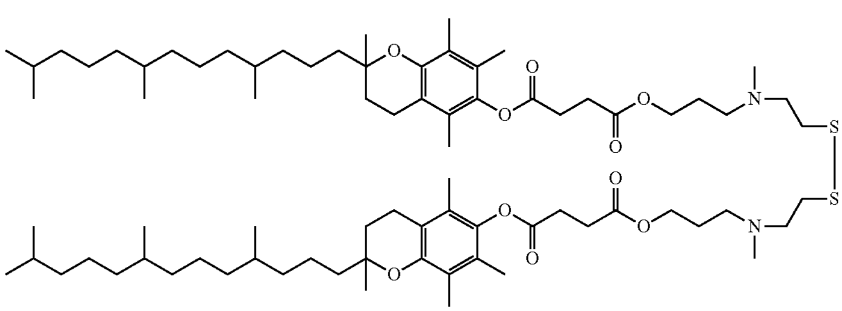 [SMILES: Cc1c(C)c2c(c(C)c1OC(=O)CCC(=O)OCCCN(C)CCSSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

TABLE 1-continued
| compound name | structure |
|---|---|
| TS-C4E | 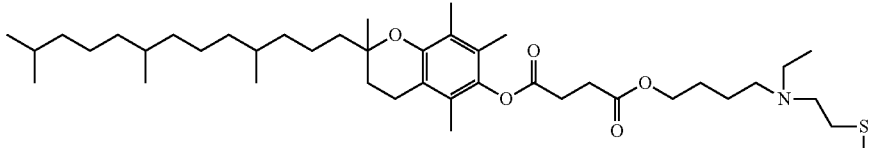 |
| TS-C5P | 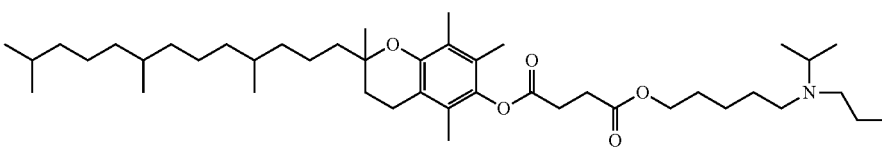 |
| TS-P2C1 | 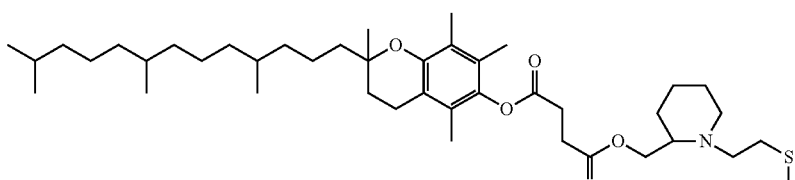 |
| TS-P3C1 | 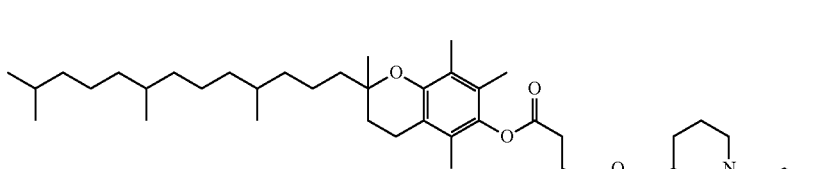 |

TABLE 1-continued

| compound name | structure |
|---|---|
| TS-P4C1 | 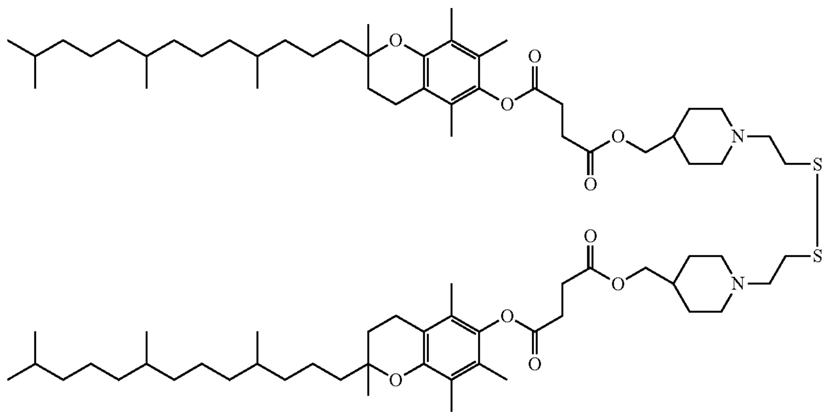 [SMILES: Cc1c(C)c2c(c(C)c1OC(=O)CCC(=O)OCC1CCN(CCSSCCN3CCC(COC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| TS-P4C2 | 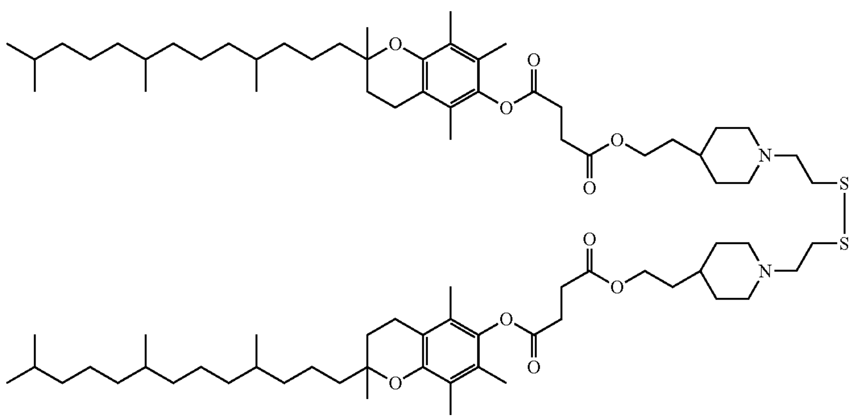 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| TS-P4C3 | 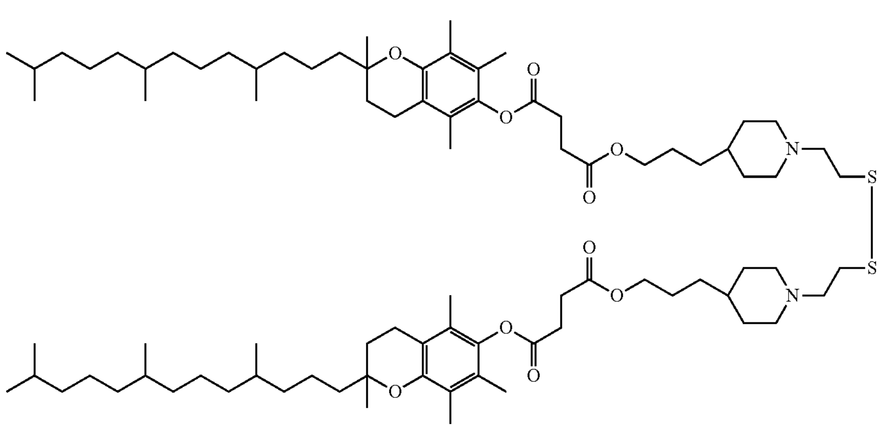 [SMILES: Cc1c(C)c2c(c(C)c1OC(=O)CCC(=O)OCCCC1CCN(CCSSCCN3CCC(CCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |

TABLE 1-continued

| compound name | structure |
|---|---|
| TS-P4C4 | 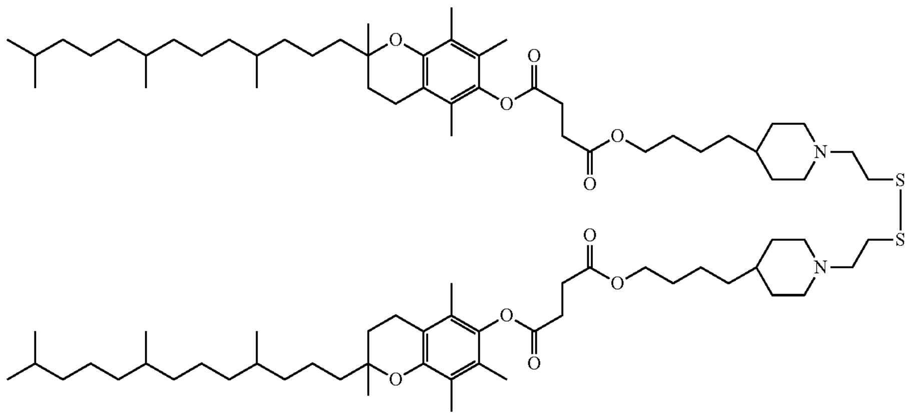 [SMILES: Cc1c(C)c2c(c(C)c1OC(=O)CCC(=O)OCCCCC1CCN(CCSSCCN3CCC(CCCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| TG-C3M | 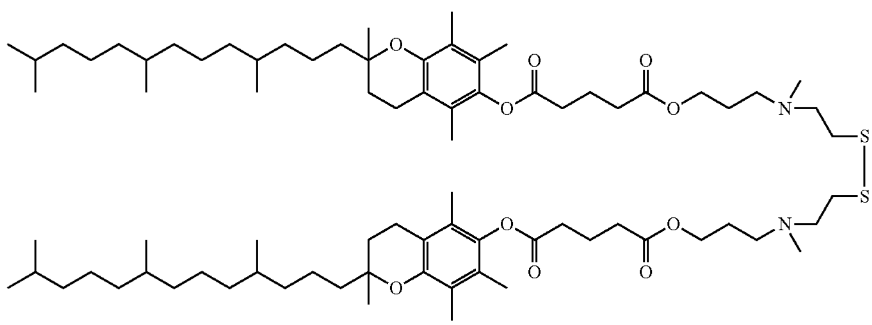 [SMILES: Cc1c(C)c2c(c(C)c1OC(=O)CCCC(=O)OCCCN(C)CCSSCCN(C)CCCOC(=O)CCCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| TSamide-C3M | 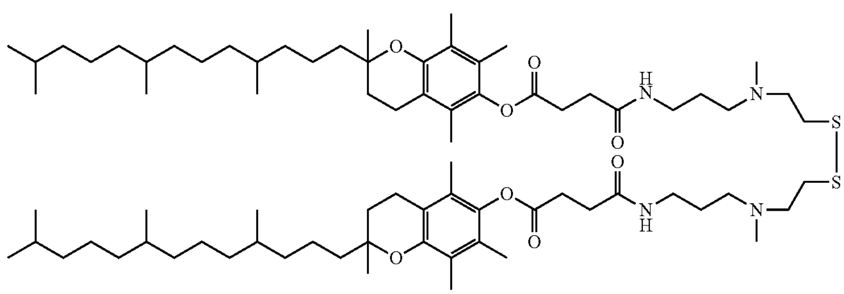 [SMILES: Cc1c(C)c2c(c(C)c1OC(=O)CCC(=O)NCCCN(C)CCSSCCN(C)CCCNC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

The production method of the compound of the present invention is explained now.

The compound of the present invention has an —S—S— (disulfide) bond. Therefore, the production method includes, for example, a method including producing
$R^{3a}$—$(Y^a$—$R^{2a})_n{}^a$—$X^a$—$R^{1a}$—SH, and
$R^{3b}$—$(Y^b$—$R^{2b})_n{}^b$—$X^b$—$R^{1b}$—SH, and
subjecting them to oxidation (coupling) to give the compound of the present invention containing —S—S—, a method including sequentially bonding necessary parts to a compound containing an —S—S— bond to finally obtain the compound of the present invention and the like. Preferred is the latter method.

A specific example of the latter method is shown below, which is not to be construed as limitative.

Examples of the starting compound include —S—S— bond-containing two terminal carboxylic acid, two terminal carboxylate, two terminal amine, two terminal isocyanate, two terminal alcohol, two terminal alcohol having a leaving group such as MsO (mesylate group) and the like, a two terminal carbonate having a leaving group such as pNP (p-nitrophenylcarbonate group) and the like, and the like.

For example, when a compound containing $X^1$ or $X^2$ for $X^a$ and $X^b$ is produced, two terminal functional groups of compound (1) containing an —S—S— bond are reacted with an —NH— group in compound (2) having the —NH— group and one functional group at the terminal, the functional group at the terminal in compound (2) which did not contribute to the reaction is reacted with a functional group in compound (3) containing $R^3$, whereby the compound of the present invention containing an —S—S— bond, $R^{1a}$ and $R^{1b}$, $X^a$ and $X^b$, $R^{2a}$ and $R^{2b}$, $Y^a$ and $Y^b$, and $R^{3a}$ and $R^{3b}$ can be obtained.

In the reaction of compound (1) and compound (2), an alkali catalyst such as potassium carbonate, sodium carbonate, potassium t-butoxide and the like may be used as a catalyst, or the reaction may be performed without a catalyst. Preferably, potassium carbonate or sodium carbonate is used as a catalyst.

The amount of catalyst is 0.1-100 molar equivalents, preferably, 0.1-20 molar equivalents, more preferably 0.1-5 molar equivalents, relative to compound (1). The amount of compound (2) to be charged is 1-50 molar equivalents, preferably 1-10 molar equivalents, relative to compound (1).

The solvent to be used for the reaction of compound (1) and compound (2) is not particularly limited as long as it is a solvent or aqueous solution that does not inhibit the reaction. For example, ethyl acetate, dichloromethane, chloroform, benzene, toluene and the like can be mentioned. Among these, toluene and chloroform are preferable.

The reaction temperature is −20 to 200° C., preferably 0 to 80° C., more preferably 20 to 50° C., and the reaction time is 1-48 hr, preferably 2-24 hr.

When the reaction product of compound (1) and compound (2) is reacted with compound (3), an alkali catalyst such as potassium carbonate, sodium carbonate, potassium t-butoxide and the like, or an acid catalyst such as PTS (p-toluenesulfonic acid), MSA (methanesulfonic acid) and the like may be used, like the catalyst used for the reaction of compound (1) and compound (2), or the reaction may be performed without a catalyst.

In addition, the reaction product of compound (1) and compound (2) may be directly reacted with compound (3) by using a condensing agent such as DCC (dicyclohexylcarbodiimide), DIC (diisopropylcarbodiimide), EDC (1-ethyl-3-(3-dimethylaminopropyl)carbodiimide hydrochloride) and the like. Alternatively, compound (3) may be treated with a condensing agent to be once converted to an anhydride and the like, after which it is reacted with the reaction product of compound (1) and compound (2).

The amount of compound (3) to be charged is 1-50 molar equivalents, preferably 1-10 molar equivalents, relative to the reaction product of compound (1) and compound (2).

The catalyst to be used is appropriately selected according to the functional groups to be reacted.

The amount of catalyst is 0.05-100 molar equivalents, preferably 0.1-20 molar equivalents, more preferably 0.2-5 molar equivalent, relative to compound (1).

The solvent to be used for the reaction of the reaction product of compound (1) and compound (2) with compound (3) is not particularly limited as long as it is a solvent or aqueous solution that does not inhibit the reaction. For example, ethyl acetate, dichloromethane, chloroform, benzene, toluene and the like can be mentioned. Among these, toluene and chloroform are preferable.

The reaction temperature is 0 to 200° C., preferably 0 to 120° C., more preferably 20 to 50° C., and the reaction time is 1 hr-48 hr, preferably 2-24 hr.

The reaction product obtained by the above-mentioned reaction can be appropriately purified by a general purification method, for example, washing with water, silica gel column chromatography, crystallization, recrystallization, liquid-liquid extraction, reprecipitation, ion exchange column chromatography and the like.

As specific examples, Examples using a compound having an —S—S— bond and leaving groups such as MsO (mesylate group) and the like at two terminals as a starting material, and involving binding 3-(methylamino)-1-propanol, and binding fatty acid or liposoluble vitamin are described below (see Examples 1-5). Those of ordinary skill in the art can produce a desired compound of the present invention by appropriately selecting the starting material and performing the reactions according to the method of the Examples.

The lipid membrane structure of the present invention is now explained. The lipid membrane structure of the present invention contains a compound represented by the above-mentioned formula (1) as a membrane-constituting lipid. Here, the "lipid membrane structure" in the present invention means a particle having membrane structure wherein the hydrophilic groups of amphipathic lipid are arranged in the interface, facing the aqueous phase side.

While the form of the inventive lipid membrane structure containing a lipid is not particularly limited, for example, liposome (monolayer liposome, multilayer liposome), O/W emulsion, W/O/W emulsion, spherical micelle, worm-like micelle, or disordered layer structure and the like can be mentioned as a form of dispersion in an aqueous solvent. The lipid membrane structure is preferably a liposome.

The lipid membrane structure of the present invention may further contain a molecule other than the compound of the present invention, for example, a lipid (phospholipid (phosphatidylinositol, phosphatidylserine, phosphatidylethanolamine, phosphatidylcholine etc.), glycolipid, peptidelipid, cholesterol, cationic lipid other than the compound of the present invention, PEG lipid etc.), a surfactant (e.g., CHAPS, sodium cholate, octylglucoside, N-D-gluco-N-methylalkaneamides etc.), polyethylene glycol, a protein and the like.

While the content of the compound of the present invention to be contained in the lipid membrane structure of the present invention is not particularly limited, when the lipid membrane structure is used as the below-mentioned agent for introducing a nucleic acid, it is generally an amount sufficient for introducing the nucleic acid. For example, the compound of the present invention is contained in 5-100 mol %, preferably 10-70 mol %, more preferably 30-50 mol %, of the total lipid.

In addition, the lipid membrane structure of the present invention can be used after modifying a surface of the lipid membrane with functional elements capable of conferring various functions to a lipid membrane structure, such as polyarginine peptide described in WO 2005/032593, GALA peptide, which is described in WO 2008/105178, that potentiates resistance to biological components, polyalkyleneglycol that enhances stability in blood, and others, by a method known for each element.

The lipid membrane structure of the present invention can be prepared by dispersing the compound of the present invention and other constituent components (lipid etc.) in a suitable dispersing medium, for example, aqueous solvent and alcoholic solvent, and performing an operation to induce organization as necessary. Examples of the "operation to induce organization" include, but are not limited to, methods known per se such as an ethanol dilution method, a simple hydration method, sonication, heating, vortex, an ether injecting method, a French press method, a cholic acid method, a $Ca^{2+}$ fusion method, a freeze-thaw method, a reversed-phase evaporation method and the like.

A nucleic acid can be introduced into a cell in vivo and/or in vitro by encapsulating the nucleic acid in the lipid membrane structure of the present invention and contacting the lipid membrane structure with the cell. Therefore, the present invention provides an agent for introducing a nucleic acid, containing the above-mentioned compound or lipid membrane structure of the present invention.

Any nucleic acid can be introduced into a cell. Examples of the kind of nucleic acid include, but are not limited to, DNA, RNA, chimera nucleic acid of DNA and RNA, DNA/RNA hybrid and the like. While any nucleic acid having 1 to 3 chains can be used, it is preferably a single strand or double strand. The nucleic acid may be other type of nucleotide such as N-glycoside of purine or pyrimidine base or other oligomer having a non-nucleotide backbone (e.g., commercially available peptide nucleic acid (PNA) etc.), other oligomer containing a special bond (said oligomer comprising base pairing or a nucleotide having a configuration permitting attachment of base, which are found in DNA and RNA) and the like. Furthermore, it may be a nucleic acid added with known modification, for example, one with a label known in the field, one with a cap, methylated one, one or more natural nucleotides substituted by an analog, one with intramolecular nucleotidyl modification, for example, one with non-charge bond (e.g., methylphosphonate, phosphotriester, phosphoramidate, carbamate and the like), one with a charged bond or sulfur-containing bond (e.g., phosphorothioate, phosphorodithioate and the like), for example, one with a side chain group such as protein (nuclease, nuclease inhibitor, toxin, antibody, signal peptide, poly-L-lysine and the like), sugar (e.g., monosaccharide and the like) and the like, one with an intercalating compound (e.g., acridine, psoralen and the like), one with a chelate compound (e.g., metal, radioactive metal, boron, oxidative metal and the like), one containing an alkylating agent, or one with a modified bond (e.g., α anomer-type nucleic acid and the like).

Any kind of DNA can be selected as appropriate according to the object of use. For example, plasmid DNA, cDNA, antisense DNA, chromosomal DNA, PAC, BAC and the like can be mentioned. Preferred are plasmid DNA, cDNA and antisense DNA, and more preferred is plasmid DNA. A circular DNA such as plasmid DNA and the like can be digested as appropriate with a restriction enzyme and the like, and also used as a linear DNA. Also, any kind of RNA can be selected as appropriate according to the object of use. For example, siRNA, miRNA, shRNA, antisense RNA, messenger RNA, single strand RNA genome, double strand RNA genome, RNA replicon, transfer RNA, ribosomal RNA and the like can be mentioned, with preference given to siRNA, miRNA, shRNA, mRNA, antisense RNA, and RNA replicon.

The nucleic acid used in the present invention is preferably purified by a method generally used by those of ordinary skill in the art.

In one embodiment, the nucleic acid used in the present invention has a low and suppressed CpG sequence frequency, and preferably does not contain a CpG sequence. Using a nucleic acid with a low CpG sequence frequency, the nucleic acid introduced into the cell stays in the cell for a long period, and maintains the physiological effect thereof for a long period. For example, when a plasmid DNA (expression vector) free of a CpG sequence is used as a nucleic acid to be used in the present invention, the object gene can be expressed in a sustained manner for a longer period. In the present specification, the CpG sequence is a 2 base sequence of a type having guanine appearing after cytosine from 5' to 3'. For example, the frequency of the CpG sequence in the nucleic acid used in the present invention is not more than one per 50 bases, preferably not more than one per 100 bases, more preferably not more than one per 1000 bases, most preferably none.

In addition, a CpG sequence induces an innate immune response, and therefore, the development of side effects such as inflammation and the like caused by the innate immune response can be avoided by using a nucleic acid having low and suppressed CpG sequence frequency (preferably, nucleic acid free of CpG sequence) in the present invention. Particularly, since the compound and the lipid membrane structure of the present invention themselves are less stimulatory, and they scarcely induce production of inflammatory cytokine when administered to the body. Thus, the risk of developing side effects such as inflammation and the like caused by innate immune response can be suppressed to the minimum by using the lipid membrane structure of the present invention and a nucleic acid having low and suppressed CpG sequence frequency (preferably, nucleic acid free of CpG sequence) in combination.

Examples of the embodiment of using the agent for introducing a nucleic acid of the present invention so as to introduce a nucleic acid into cells in the body include use for the administration of a nucleic acid for the prophylaxis and/or treatment to the body (in vivo) with the aim of preventing or treating a disease, such as what is called gene therapy. Therefore, in one preferable embodiment of the present invention, the nucleic acid to be introduced into cells by the agent for introducing a nucleic acid of the present invention has a prophylactic and/or therapeutic activity for a given disease.

To introduce a nucleic acid into cells by the use of the agent for introducing a nucleic acid of the present invention, the lipid structure of the present invention encapsulating the nucleic acid is formed by the co-presence of the object nucleic acid when forming the lipid membrane structure of the present invention. For example, when a liposome is formed by an ethanol dilution method, an aqueous nucleic acid solution and a solution of the constituent components (lipid etc.) of the lipid membrane structure of the present invention in an ethanol are vigorously stirred in a vortex and the like, and the mixture is diluted with an appropriate buffer. When a liposome is formed by a simple hydration method, the constituent components (lipid etc.) of the lipid membrane structure of the present invention are dissolved in an appropriate organic solvent, and the solution is placed in a glass container and dried under reduced pressure to evaporate the solvent, whereby a lipid thin film is obtained. Thereto is added an aqueous nucleic acid solution and, after hydration, the mixture is sonicated by a sonicator. The present invention also provides such above-mentioned lipid membrane structure encapsulating a nucleic acid.

As one form of liposome encapsulating a nucleic acid, a multifunctional envelope-type nano device (MEND; hereinafter sometimes to be abbreviated as "MEND" in the present specification) prepared by encapsulating an electrostatic complex of a nucleic acid and a polycation (e.g., protamine) in a liposome can be mentioned (Kogure K et al., Multifunctional envelope-type nano device (MEND) as a non-viral gene delivery system. Adv Drug Deliv Rev. 2008). This structure can be used as a drug delivery system for selectively delivering a nucleic acid and the like into a particular cell, and useful for, for example, a DNA vaccine, gene therapy of tumor and the like, by introducing antigen gene into dendritic cells.

The surface charge (zeta potential) of the lipid membrane structure of the present invention encapsulating the nucleic acid is preferably −10 to +10 mV, more preferably −10 to +5 mV. In a further embodiment, the surface charge (zeta potential) of the lipid membrane structure of the present invention is preferably −15-+10 mV, more preferably −13-+7 mV. In conventional transgene, particles electrically charged to have a plus surface potential have been mainly used. This is useful as a method for promoting electrostatic interactions with heparin sulfate on the negatively-charged cell surface to enhance uptake into cells. However, positive surface charge may induce suppression of transcription due to the intracellular interaction with the introduced gene and suppression of translation due to the intracellular interaction with mRNA. This problem can be solved by adjusting the surface charge to fall within the above-mentioned range. The surface charge can be measured using Metasizer Nano (Malvern). The surface charge of the lipid membrane structure can be adjusted by the composition of the constituent component of the lipid membrane structure containing the compound of the present invention.

The thus-obtained lipid membrane structure of the present invention encapsulating the nucleic acid is brought into contact with cells to introduce the encapsulated nucleic acid into the cells. The kind of the cell is not particularly limited, a prokaryotic or eucaryotic cell can be used, with preference given to eucaryote. The kind of the eukaryotic cell is not particularly limited and, for example, vertebrates such as mammals including human (human, monkey, mouse, rat, hamster, bovine etc.), birds (chicken, ostrich etc.), amphibia (frog etc.), fishes (zebrafish, rice-fish etc.) and the like, invertebrates such as insects (silk moth, moth, Drosophila etc.) and the like, plants, microorganisms such as yeasts, and the like can be mentioned. More preferably, the target cell in the present invention is an animal or plant cell, more preferably a mammalian cell. The cell may be a culture cell line including a cancer cell, or a cell isolated from an individual or tissue, or a cell of a tissue or tissue piece. The cell may be an adherent cell or a non-adherent cell.

In one embodiment using the compound of the present invention, wherein $R^{3a}$ and $R^{3b}$ are retinoic acid residues, the target cell into which the nucleic acid is to be introduced is preferably a cell expressing cellular retinoic acid-binding protein II (CRABPII). Since CRABPII has a function to transport retinoic acid to the nucleus in a sumoylation dependent manner, use of the compound of the present invention, wherein $R^{3a}$ and $R^{3b}$ are retinoic acid residues, is expected to promote transport of the nucleic acid into the nucleus, due to the function of CRABPII. Whether the cell expresses CRABPII can be confirmed by Western blotting and the like. Specific examples of the organ that expresses CRABPII include, but are not limited to, normal tissues such as skin, testis, uterus, ovary, choroid plexus and the like, various cancer tissues (retina blastoma, Wilms' tumor), and specific examples of the cell that expresses CRABPII include, but are not limited to, fibrosarcoma cell (HT1080 cell), orally squamous cell carcinoma (BHY cell), breast cancer cell (KATO3 cell, BT474, MCF-7, MDA-MB-134) and the like.

The step of contacting the lipid membrane structure of the present invention encapsulating the nucleic acid with the cell in vitro is specifically explained below.

The cells are suspended in a suitable medium several days before contact with the lipid membrane structure, and cultured under appropriate conditions. At the time of contact with the lipid membrane structure, the cells may or may not be in a proliferative phase.

The culture medium on contact may be a serum-containing medium or a serum-free medium, wherein the serum concentration of the medium is preferably not more than 30%, more preferably not more than 20%, since when the medium contains excess protein such as serum and the like, the contact between the complex and the cell may be inhibited.

The cell density on contact is not particularly limited, and can be appropriately determined in consideration of the kind of the cell and the like. It is generally within the range of $1 \times 10^4$-$1 \times 10^7$ cells/mL.

A suspension of the aforementioned lipid membrane structure is added to the thus-prepared cells. The amount of the complex-containing solution to be added is not particularly limited, and can be appropriately determined in consideration of the cell number and the like. The concentration of the lipid membrane structure to be contacted with the cells is not particularly limited as long as the desired introduction of the nucleic acid into the cells can be achieved. The lipid concentration is generally 1-100 nmol/ml, preferably 10-50 nmol/ml, and the concentration of the nucleic acid is generally 0.01-100 μg/ml, preferably 0.1-10 μg/ml.

The temperature, humidity and $CO_2$ concentration when the complex-containing solution is added to the medium and the cells are cultured are appropriately determined in consideration of the kind of the cell. In the case of a mammalian cell, temperature about 37° C., humidity about 95% and $CO_2$ concentration about 5% are generally employed. While the culture period can also be appropriately determined in consideration of the conditions such as the kind of the cell and the like, it is generally 0.1-24 hr, preferably 0.25-4 hr, more preferably 0.5-2 hr. When the above-mentioned culture time is too short, the nucleic acid is not sufficiently introduced into the cells, and when the culture time is too long, the cells may become weak.

By the above-mentioned culture, the nucleic acid is introduced into cells. The culture is further continued preferably by exchanging the medium with a fresh medium, or adding a fresh medium to the medium. When the cell is a mammal-derived cell, the fresh medium preferably contains a serum or nutrition factor.

As mentioned above, a nucleic acid can be introduced into cells not only outside the body (in vitro) but also in the body (in vivo) by using the lipid membrane structure of the present invention. That is, by administration of the lipid membrane structure of the present invention encapsulating the nucleic acid to a subject, the lipid membrane structure reaches and contacts with the target cells, and the nucleic acid encapsulated in the lipid membrane structure is introduced into the cells in vivo. The subject to which the complex can be administered is not particularly limited and, for example, vertebrates such as mammals including human (human, monkey, mouse, rat, hamster, bovine etc.), birds (chicken, ostrich etc.), amphibia (frog etc.), fishes (zebrafish, rice-fish etc.) and the like, invertebrates such as insects (silk moth, moth, Drosophila etc.) and the like, plants and the like can be mentioned. The subject of administration of the complex is preferably human or other mammal.

The kind of the target cell is not particularly limited, and a nucleic acid can be introduced into cells in various tissues (e.g., liver, kidney, pancreas, lung, spleen, heart, blood, muscle, bone, brain, stomach, small intestine, large intestine, skin, adipose tissue etc.) by using the lipid membrane structure of the present invention.

The administration method of the complex is not particularly limited as long as the complex reaches and contacts with the target cells, and the compound to be introduced, which is contained in the complex, can be introduced into the cells, and an administration method known per se (oral administration, parenteral administration (intravenous administration, intramuscular administration, topical administration, transdermal administration, subcutaneous administration, intraperitoneal administration, spray etc.) etc.) can be appropriately selected in consideration of the kind of the compound to be introduced, the kind and the site of the target cell and the like. The dose of the lipid membrane structure is not particularly limited as long as the introduction of the compound into the cells can be achieved, and can be appropriately selected in consideration of the kind of the subject of administration, administration method, the kind of the compound to be introduced, the kind and the site of the target cell and the like.

When the compound or lipid membrane structure of the present invention is used as an agent for introducing a nucleic acid, they can be formulated according to a conventional method.

When the agent is provide as a reagent for studies, the carrier of the present invention can be provide as it is or as a sterile solution or suspension with, for example, water or other physiologically acceptable solution (e.g., the aforementioned aqueous solvent, organic solvent such as ethanol, methanol, DMSO and the like or a mixture of aqueous solvent and organic solvent etc.). The agent can appropriately contain physiologically acceptable excipient, vehicle, preservative, stabilizer, binder and the like, which are known per se.

When the agent is provide as a medicament, the carrier of the present invention can be provide as an oral preparation (for example, tablet, capsule etc.) or parenteral agent (for example, injection, spray etc.) as it is or by blending the carrier with a pharmaceutically acceptable known additives such as carrier, flavor, excipient, vehicle, preservative, stabilizer, binder and the like in a conventionally admitted unit dosage form required for practicing preparation formulation.

The agent for introducing a nucleic acid of the present invention can also be provided in the form of a kit. The kit can contain, in addition to the compound or lipid membrane structure of the present invention, a reagent used for the introduction of a nucleic acid. In one embodiment, the agent (or kit) for introducing a nucleic acid of the present invention further contains a polycation (e.g., protamine). Using the agent (or kit) for introducing a nucleic acid of the present invention in this embodiment, an electrostatic complex of nucleic acid and polycation (e.g., protamine) can be easily encapsulated in the lipid membrane structure of the present invention to constitute MEND, which can be subjected to the intracellular introduction of a nucleic acid.

EXPLANATION OF ABBREVIATIONS pDNA: plasmid DNA
Chol: Cholesterol
NBD-DOPE: 1,2-Dioleoyl-sn-glycero-3-phosphoethanolamine-N-(7-nitro-2-1,3-benzoxadiazol-4-yl)
DMEM: Dulbecco's modified eagle medium
$PEG_{2000}$-DSG: 1,2-Distearoyl-sn-glycerol, methoxypolyethylene Glycol (PEG MW 2000)
$PEG_{2000}$-DMG: 1,2-Dimyristoyl-sn-glycerol, methoxypolyethylene Glycol (PEG MW 2000)
DOPE: 1,2-Dioleyl-sn-glycero-3-phosphoethanolamine
SOPS: 1-Stearoyl-2-oleoyl-sn-glycero-3-phosphoethanolamine
SOPC: 1-Stearoyl-2-oleoyl-sn-glycero-3-phosphocholine

EXAMPLES

Examples of the present invention are explained in more detail in the following.

Table 2 shows the names and structures of the compounds produced in the following Examples and Comparative Examples.

TABLE 2

| | compound name | structure |
|---|---|---|
| Ex. 1 | B-2 | 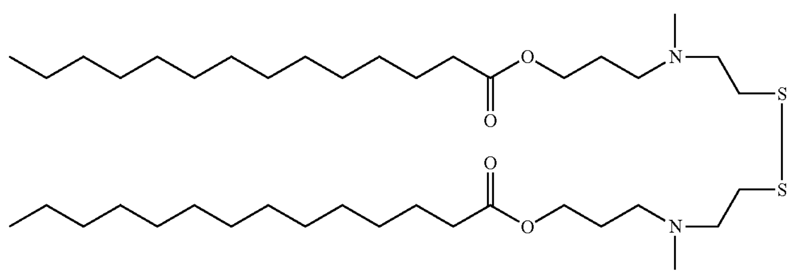 [SMILES: CCCCCCCCCCCCCC(=O)OCCCN(C)CCSSCCN(C)CCCOC(=O)CCCCCCCCCCCCC] |
| Ex. 2 | B-2-2 | 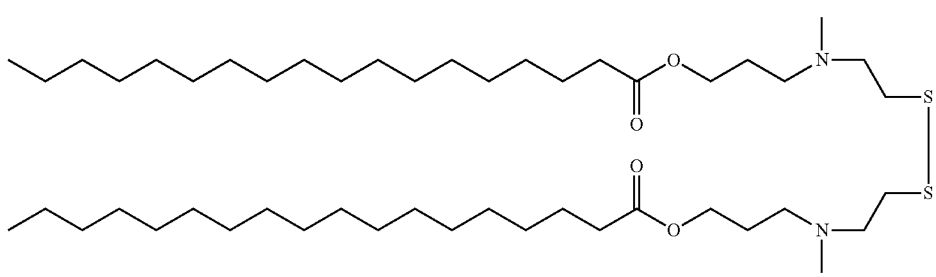 [SMILES: CCCCCCCCCCCCCCCCCC(=O)OCCCN(C)CCSSCCN(C)CCCOC(=O)CCCCCCCCCCCCCCCCC] |
| Ex. 3 | B-2-3 | 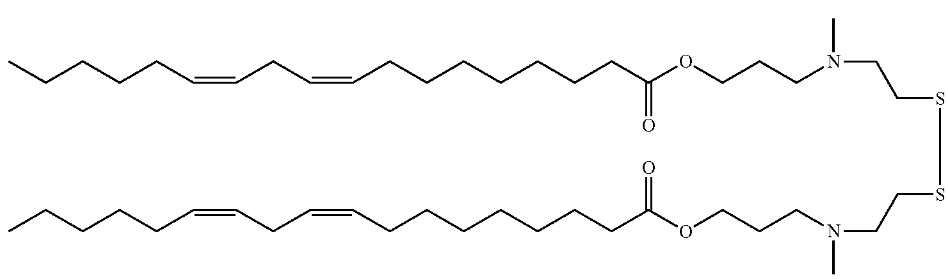 [SMILES: CCCCC/C=C\C/C=C\CCCCCCCC(=O)OCCCN(C)CCSSCCN(C)CCCOC(=O)CCCCCCC/C=C\C/C=C\CCCCC] |

TABLE 2-continued

| compound name | structure |
|---|---|
| Ex. 4 B-2-4 | |
| Ex. 5 B-2-5 | |
| Ex. 6 TS-C4E | |
| Ex. 7 TS-C5P | |

TABLE 2-continued
| compound name | structure |
|---|---|
| Ex. 8 TS-P2C1 | 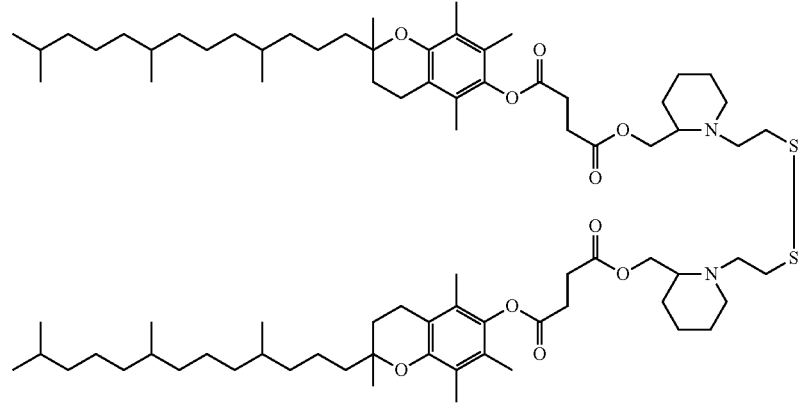 [SMILES: Cc1c(C)c2c(c(C)c1OC(=O)CCC(=O)OCC1CCCCN1CCSSCCN1CCCCC1COC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| Ex. 9 TS-P3C1 | 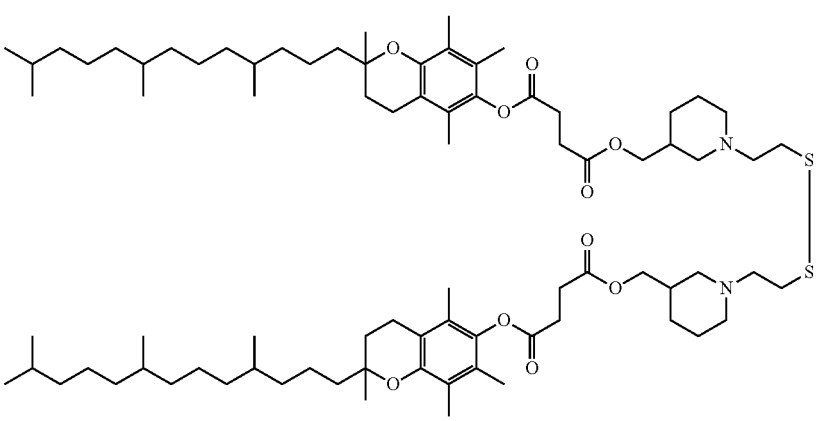 [SMILES: Cc1c(C)c2c(c(C)c1OC(=O)CCC(=O)OCC1CCCN(CCSSCCN3CCCC(COC(=O)CCC(=O)Oc4c(C)c(C)c5c(c4C)CCC(C)(CCCC(C)CCCC(C)CCCC(C)C)O5)C3)C1)CCC(C)(CCCC(C)CCCC(C)CCCC(C)C)O2] |
| Ex. 10 TS-P4C1 | 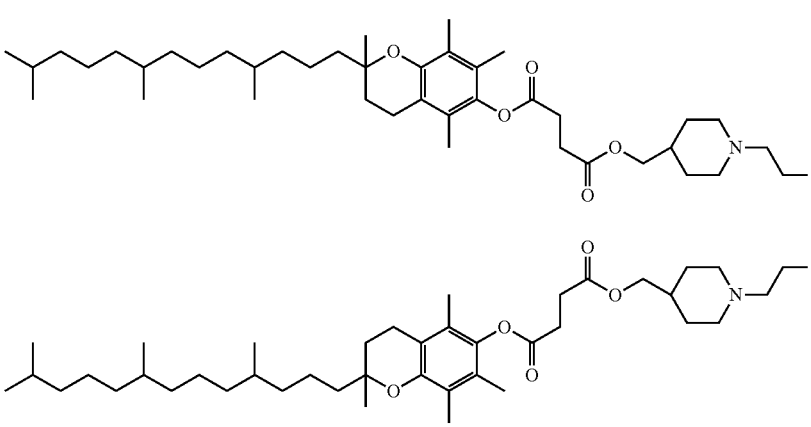 |

TABLE 2-continued

| | compound name | structure |
|---|---|---|
| Ex. 11 | TS-P4C2 | 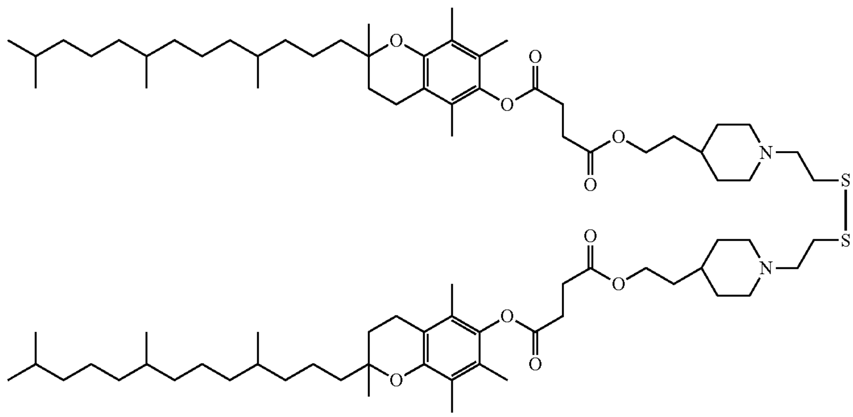 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| Ex. 12 | TS-P4C3 | 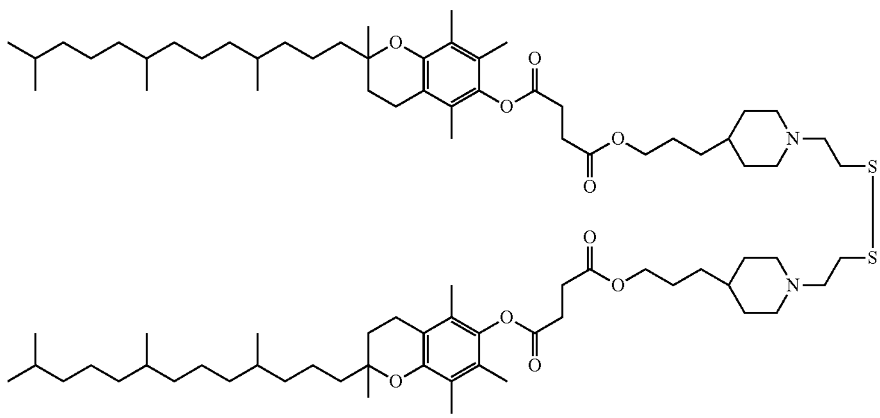 [SMILES: Cc1c(C)c2c(c(C)c1OC(=O)CCC(=O)OCCCC1CCN(CCSSCCN3CCC(CCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| Ex. 13 | TS-P4C4 | 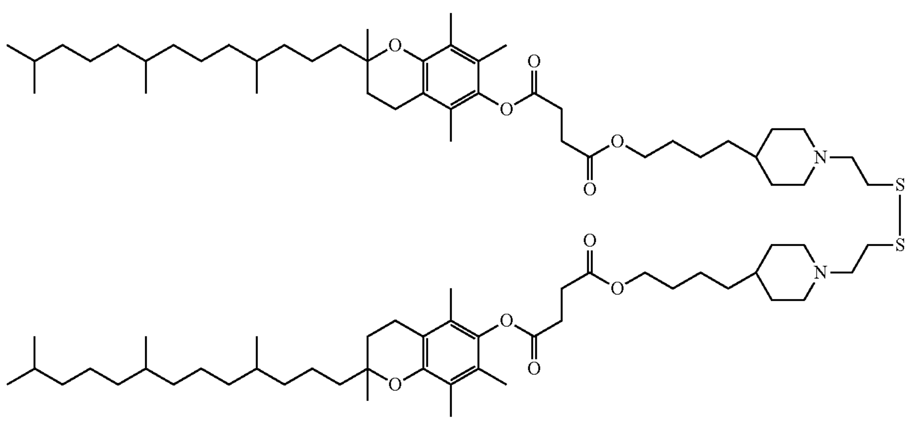 [SMILES: Cc1c(C)c2c(c(C)c1OC(=O)CCC(=O)OCCCCC1CCN(CCSSCCN3CCC(CCCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| Ex. 14 | TG-C3M | 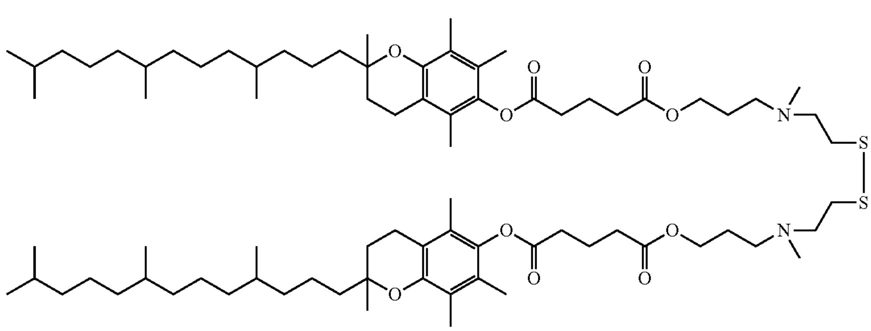 [SMILES: Cc1c(C)c2c(c(C)c1OC(=O)CCCC(=O)OCCCN(C)CCSSCCN(C)CCCOC(=O)CCCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

TABLE 2-continued

| compound name | structure |
|---|---|
| Ex. 15 TSamide-C3M | 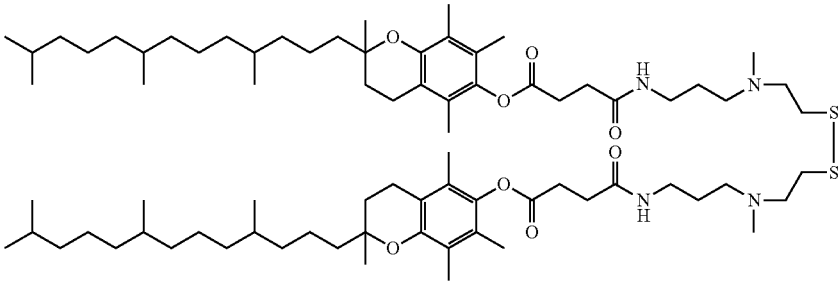 [SMILES: Cc1c(C)c2c(c(C)c1OC(=O)CCC(=O)NCCCN(C)CCSSCCN(C)CCCNC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| Comp. Ex. 1 B-2-1 | 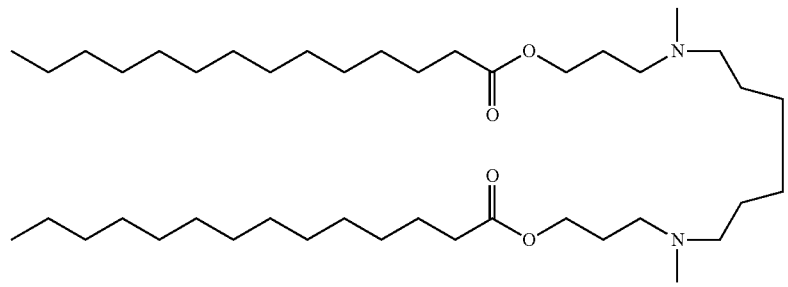 [SMILES: CCCCCCCCCCCCCC(=O)OCCCN(C)CCCCCCN(C)CCCOC(=O)CCCCCCCCCCCCC] |
| Comp. Ex. 2 DADAP | 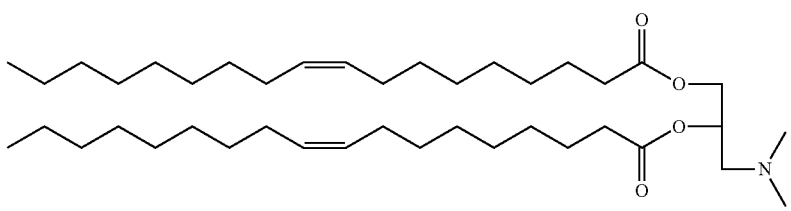 [SMILES: CCCCCCCC/C=C\CCCCCCCC(=O)OCC(CN(C)C)OC(=O)CCCCCCC/C=C\CCCCCCCC] |
| Comp. Ex. 3 DOTAP | 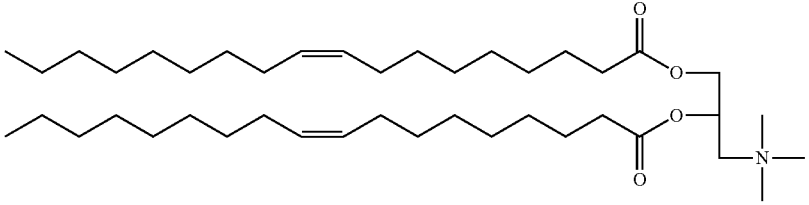 |

[Example 1] (Synthesis of B-2)
<Mesylation>

Acetonitrile (143 ml) was added to 2,2'-dithiodiethanol (manufactured by ACROS) (15 g, 97.2 mmol) and the mixture was dissolved at 20-25° C. Triethylamine (33.3 g, 328 mmol) was added and, after stirring at 20-25° C. for 5 min, methanesulfonyl chloride 34.5 g (300 mmol) was added under ice-cooling and the mixture was reacted at 20-25° C. for 3 hr. TLC analysis (eluent: chloroform/methanol=85/15 (v/v)) confirmed that a spot of the reaction product was obtained and the starting material 2,2'-dithiodiethanol disappeared, with which the reaction was terminated. The reaction was discontinued by adding ethanol (29 mL) to the reaction solution, and insoluble materials were filtered off using filter paper (5A). To the filtrate were added dichloromethane (150 ml) and 10% sodium bicarbonate water (150 g), and the mixture was stirred for 5 min, stood for 10 min and the aqueous layer was removed. To the organic layer was added water (150 g) and the mixture was stirred for 5 min, stood for 10 min and the aqueous layer was removed. After washing 4 times with water, the organic layer was recovered and dehydrated by adding sodium sulfate (4.5 g). After the dehydration treatment, filtration was performed using Opuraito and filter paper (5A). The solvent of the filtrate was evaporated by an evaporator to give a brown liquid (29.4 g).

<Tertiary Amination>

The dimesylated compound (5.0 g, 16 mmol) was dissolved in acetonitrile (127 ml) at 40° C., potassium carbonate (5.5 g, 39.8 mmol) was added and the mixture was stirred at 25° C. for 5 min. 3-(Methylamino)-1-propanol (manufactured by Tokyo Chemical Industry) (7.2 g, 80.8 mmol) was dissolved in acetonitrile (9.2 ml) at 25° C., and added dropwise to the above-mentioned dimesylated compound/acetonitrile solution over 1.5 hr. At 2 hr after completion of dropwise addition, TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (13.2 g).

The obtained brown liquid was dissolved in chloroform (132 ml), and washed with 10% brine (132 ml). The aqueous layer was discarded, and washing with 10% brine was repeated 5 times to remove the starting material, 3-(methylamino)-1-propanol. The chloroform layer was recovered, and the solvent was evaporated by an evaporator to give a pale-yellow transparent liquid (hereinafter di-MAP compound) (4.3 g).

<Acylation>

Myristic acid (1.5 g, 6.7 mmol) was dissolved in dichloromethane (5.8 ml), DMAP (0.082 g, 0.67 mmol) was added, and TEA (0.68 g, 6.7 mmol) was added under ice-cooling. To this solution was added dropwise a solution of di-MAP compound (1 g, 3.4 mmol) and diisopropylcarbodiimide (hereinafter DIC) (1.7 g, 13.5 mmol) dissolved in dichloromethane (5.8 ml) over 1 hr. At 2 hr after completion of the dropwise addition, TLC analysis (eluent: chloroform/methanol=95/5 (v/v)) was performed. The results confirmed disappearance of di-MAP compound, with which the reaction was terminated. Insoluble materials were filtered off using filter paper (5A), and the solvent was evaporated by an evaporator to give a colorless transparent liquid (7.2 g). To the liquid was added acetonitrile (38 ml) and cooling crystallization (10° C.) was performed 3 times. The obtained crystals were dissolved in hexane (45 ml), and acetonitrile (38 ml) was added thereto for extraction washing. The acetonitrile layer was discarded, the extraction washing was further repeated 6 times to remove impurities derived from DIC and myristic acid. The hexane layer was recovered, and the solvent was evaporated by an evaporator to give the object product, compound B-2 (0.73 g).

Results of $^1$H-NMR (400 MHz CDCl$_3$) Analysis

δ0.85~0.9 ppm (t, C$\underline{H}_3$—CH$_2$—, 6H), δ1.22~1.35 ppm (m, CH$_3$—(C$\underline{H}_2$)$_{10}$—, 40H), δ2.67~2.7 ppm (q, —N(CH$_3$)—CH$_2$—C$\underline{H}_2$—S—, 4H), δ2.78~2.82 (q, —N(CH$_3$)—C$\underline{H}_2$—CH$_2$—S—, 4H), δ4.10~4.13 (t, —CH$_2$—C(O)—O—C$\underline{H}_2$—, 4H)

[Example 2] (Synthesis of B-2-2)

di-MAP compound (2.0 g, 6.7 mmol) and stearic acid (4.6 g, 16.2 mmol) were dissolved in chloroform (20 ml), and DMAP (0.33 g, 2.7 mmol) and 1-ethyl-3-(3-dimethylaminopropyl)carbodiimide hydrochloride (hereinafter EDC) (3.9 g, 20.3 mmol) were added. At 4 hr after the reaction, TLC analysis (eluent: chloroform/methanol=95/5 (v/v)) was performed. The results confirmed disappearance of di-MAP compound, with which the reaction was terminated. Thereafter, the reaction mixture was extraction-washed with 5% aqueous sodium bicarbonate (10 g), after which the aqueous layer was discarded. Then, to the recovered organic layer was added water (10 g) to wash the layer with water. The aqueous layer was discarded, and magnesium sulfate (0.4 g) was added to the organic layer to perform a dehydrating treatment. Insoluble materials were filtered off by filtration using Opuraito and filter paper (5A), and the solvent was evaporated by an evaporator to give an orange liquid (hereinafter diacylated compound) (7.9 g).

The diacylated compound was dissolved in hexane (45 ml), and acetonitrile (38 ml) was added to perform extraction washing. The acetonitrile layer was discarded, and hexane/acetonitrile washing was repeated twice. The hexane layer was recovered, and the solvent was evaporated by an evaporator to give a colorless transparent liquid (7.1 g). The obtained liquid was purified by silica gel column chromatography (eluent: ethyl acetate) to give the object product, compound B-2-2 (1.4 g).

Results of $^1$H-NMR (400 MHz CDCl$_3$) Analysis

δ0.85~0.9 ppm (t, C$\underline{H}_3$—CH$_2$—, 6H), δ1.22~1.35 ppm (m, CH$_3$—(C$\underline{H}_2$)$_{14}$—, 56H), δ2.67~2.7 ppm (q, —N(CH$_3$)—CH$_2$—C$\underline{H}_2$—S—, 4H), δ2.78~2.82 (q, —N(CH$_3$)—C$\underline{H}_2$—CH$_2$—S—, 4H), δ4.10~4.13 (t, —CH$_2$—C(O)—O—C$\underline{H}_2$—, 4H)

[Example 3] (Synthesis of B-2-3)

The di-MAP compound (2.0 g, 6.7 mmol) and linoleic acid (4.5 g, 16.0 mmol) were dissolved in chloroform (20 ml), and DMAP (0.33 g, 2.7 mmol) and EDC (3.9 g, 20.3 mmol) were added. At 4 hr after the reaction, TLC analysis (eluent: chloroform/methanol=95/5 (v/v)) was performed. The results confirmed disappearance of the di-MAP compound, with which the reaction was terminated. Thereafter, the reaction mixture was extraction-washed with 5% aqueous sodium bicarbonate (10 g), and the aqueous layer was discarded. Then, to the recovered organic layer was added water (10 g) to wash the layer with water. The aqueous layer was discarded, and magnesium sulfate (0.4 g) was added to the organic layer to perform a dehydrating treatment. Insoluble materials were filtered off by filtration using Opuraito and filter paper (5A), and the solvent was evaporated by an evaporator to give a diacylated compound (6.0 g) as an orange liquid.

The obtained liquid was purified by silica gel column chromatography (eluent: hexane/ethyl acetate=5/5 (v/v)) to give the object product, compound B-2-3 (0.7 g).

Results of $^1$H-NMR (400 MHz CDCl$_3$) Analysis

δ0.85~0.9 ppm (t, C$\underline{H}_3$—CH$_2$—, 6H), δ1.22~1.35 ppm (m, CH$_3$—(C$\underline{H}_2$)$_3$—, (C$\underline{H}_2$)$_4$—CH$_2$—CH$_2$—C(O)—O—, 28H), δ2.67~2.7 ppm (q, —N(CH$_3$)—CH$_2$—C$\underline{H}_2$—S—, 4H), δ4.10~4.13 (t, —CH$_2$—C(O)—O—C$\underline{H}_2$—, 4H), δ5.30~5.40 (m, —CH$_2$—C$\underline{H}$=C$\underline{H}$—CH$_2$—, 8H)

[Example 4]

(Synthesis of B-2-4)

The di-MAP compound (0.40 g, 1.35 mmol) and retinoic acid (all-trans-retinoic acid, Wako Pure Chemical Industries, Ltd.) (0.97 g, 3.24 mmol) were dissolved in chloroform (6.00 g). DMAP (0.07 g, 0.54 mmol) and EDC (0.78 g, 4.05 mmol) were added, and the mixture was reacted at 25±3° C. for 5 hr. TLC analysis (eluent: chloroform/methanol=9/1 v/v) confirmed disappearance of di-MAP compound, with which the reaction was terminated. The solvent was evaporated by an evaporator to give a liquid (2.70 g). The liquid was purified by silica gel column chromatography (eluent: chloroform/methanol=98/2 (v/v)) to give the object product, compound B-2-4 (0.42 g).

Results of $^1$H-NMR (400 MHz CDCl$_3$) Analysis

δ 1.00~1.10 ppm (s, (C$\underline{H}_3$)$_2$C—, 12H), δ 1.45~1.50 ppm (t, (CH$_3$)$_2$C—C$\underline{H}_2$—CH$_2$—, 4H), δ 1.55~1.65 ppm (m, —CH$_2$—C$\underline{H}_2$—CH$_2$—, 4H), δ 1.70~1.75 (s, —CH$_2$—C(C$\underline{H}_3$)=C—, 6H), δ 1.80~1.90 (t, —N(CH$_3$)—CH$_2$—C$\underline{H}_2$—CH$_2$—O—C(O)—, 4H), δ 1.95~2.05 (m, —CH$_2$—C$\underline{H}_2$—C(CH$_3$)=C—, =CH—CH(C$\underline{H}_3$)=CH—, 10H), δ 2.20-2.30 (s, —N(C$\underline{H}_3$)—, 6H), δ 2.30~2.40 (s, —C(C$\underline{H}_3$)=CH—C(O)—O—, 6H), δ 2.45~2.55 (t, —N(CH$_3$)—C$\underline{H}_2$—CH$_2$—CH$_2$—O—C(O)—, 4H), δ 2.65~2.75 (t, —N(CH$_3$)—CH$_2$—C$\underline{H}_2$—S—, 4H), δ 2.75~2.85 (t, —N(CH$_3$)—C$\underline{H}_2$—CH$_2$—S—, 4H), δ 4.10~4.25 (t, —N(CH$_3$)—CH$_2$—CH$_2$—C$\underline{H}_2$—O—C(O)—, 4H)

[Example 5]

(Synthesis of B-2-5)

The di-MAP compound (0.50 g, 1.69 mmol) and D-α-tocopherol succinate (SIGMA-ALDRICH) (2.15 g, 4.06 mmol) were dissolved in chloroform (7.50 g), DMAP (0.08 g, 0.62 mmol) and EDC (0.97 g, 5.07 mmol) were added, and the mixture was reacted at 25±3° C. for 4 hr. TLC analysis (eluent: chloroform/methanol=9/1 v/v) confirmed disappearance of di-MAP compound, with which the reaction was terminated. The solvent was evaporated by an evaporator to give a liquid (2.23 g). The liquid was purified by silica gel column chromatography (eluent: chloroform/methanol=98.5/1.5 (v/v)) to give the object product, compound B-2-5 (0.94 g).

Results of $^1$H-NMR (400 MHz CDCl$_3$) Analysis

δ 0.85~0.9 ppm (t, C$\underline{H}_3$—CH$_2$—, —CH$_2$—(C$\underline{H}_3$—)CH—CH$_2$—, 24H), δ 1.00~1.75 ppm (m, CH$_3$—C$\underline{H}$(CH$_3$)—(C$\underline{H}_2$)$_3$—C$\underline{H}$(CH$_3$)—(C$\underline{H}_2$)$_3$—C$\underline{H}$(CH$_3$)—(C$\underline{H}_2$)$_3$—, 42H), δ 1.75~1.85 ppm (q, —N(CH$_3$)—CH$_2$—C$\underline{H}_2$—CH$_2$—O—C(O)—, 4H), δ 1.95~2.15 (s, —C=C(C$\underline{H}_3$)—, 18H), δ 2.20~2.30 (s, —N(C$\underline{H}_3$)—, 6H), δ 2.40~2.50 (t, —N(CH$_3$)—CH$_2$—CH$_2$—S—, 4H), δ 2.50~2.63 (t, —CH$_2$—C$\underline{H}_2$—CH=CH—, 4H), δ 2.63~2.70 (t, —N(CH$_3$)—C$\underline{H}_2$—CH$_2$—S—, 4H), δ 2.70~2.85 (m, —N(CH$_3$)—C$\underline{H}_2$—CH$_2$—CH$_2$—O—C(O)—, Ph-O—C(O)—CH$_2$—C$\underline{H}_2$—C(O)—, 8H), δ 2.85~3.00 (t, Ph-O—C(O)—CH$_2$—C$\underline{H}_2$—C(O)—, 4H), δ 4.10~4.25 (t, —N(CH$_3$)—CH$_2$—CH$_2$—CH$_2$—O—C(O)—, 4H)

[Example 6]
(Synthesis of TS-C4E)
<Tertiary Amination>

The dimesylated compound (1.00 g, 3.22 mmol) was dissolved in acetonitrile (26 ml) at 25° C., potassium carbonate (1.11 g, 8.05 mmol) was added and the mixture was stirred at 25° C. for 5 min. 4-(Ethylamino)-1-butanol (manufactured by Tokyo Chemical Industry) (3.78 g, 32.21 mmol) was added to the above-mentioned dimesylated compound/acetonitrile solution. At 16 hr after completion of dropwise addition, TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (3.76 g). The obtained brown liquid was dissolved in chloroform (38 ml), and washed with 5% aqueous sodium bicarbonate (38 ml). The aqueous layer was discarded, and washing with 5% aqueous sodium bicarbonate was performed once to remove the starting material, 4-(ethylamino)-1-butanol. The chloroform layer was recovered, and the solvent was evaporated by an evaporator to give a transparent brown liquid (hereinafter di-EAB compound) (0.90 g).

<Acylation>

The di-EAB compound (0.50 g, 1.42 mmol) and D-α-tocopherol succinate (1.51 g, 2.84 mmol) were dissolved in chloroform (5 ml), DMAP (0.07 g, 0.57 mmol) and EDC (0.82 g, 4.25 mmol) were added and the mixture was reacted at 30° C. for 4 hr. TLC analysis (eluent: chloroform/methanol=9/1 (v/v)) confirmed disappearance of the di-EAB compound, whereby the reaction was completed. The solvent was evaporated by an evaporator to give a liquid (3.33 g). This liquid was purified by silica gel column chromatography (eluent: chloroform/methanol=98/2 (v/v)) to give the object product, TS-C4E compound (1.08 g).

Results of $^1$H-NMR (400 MHz CDCl$_3$) Analysis

δ 0.80~0.90 ppm (m, (C$\underline{H}_3$)$_2$—CH—, —CH$_2$—(C$\underline{H}_3$—)CH—CH$_2$—, 24H), δ 1.00~1.85 ppm (m, —N—CH$_2$—C$\underline{H}_3$, CH$_3$—C$\underline{H}$(CH$_3$)—(C$\underline{H}_2$)$_3$—C$\underline{H}$(CH$_3$)—(C$\underline{H}_2$)$_3$—C$\underline{H}$(CH$_3$)—(C$\underline{H}_2$)$_3$—, —O—C(C$\underline{H}_3$)—, —C=C—CH$_2$—C$\underline{H}_2$—, —C(O)—O—CH$_2$—C$\underline{H}_2$—CH$_2$—N—, 66H), δ 1.95~2.10 ppm (s, —C=C(C$\underline{H}_3$)—, 18H), δ 2.40~2.48 ppm (t, —O—CH$_2$—CH$_2$—C$\underline{H}_2$—N—, 4H), δ 2.50~2.55 ppm (q, —N—C$\underline{H}_2$—CH$_3$, 4H), δ 2.56~2.60 ppm (t, —CH$_2$—C$\underline{H}_2$—C=C—O—, 4H), δ 2.70~2.77 ppm (m, —N—C$\underline{H}_2$—CH$_2$—S—, Ph-O—C(O)—CH$_2$—C$\underline{H}_2$—C(O)—O—, 12H), δ 2.91~2.95 ppm (t, Ph-O—C(O)—CH$_2$—C$\underline{H}_2$—C(O)—O—, 4H), δ 4.10~4.15 ppm (t, C(O)—O—C$\underline{H}_2$—CH$_2$—CH$_2$—, 4H)

[Example 7]
(Synthesis of TS-C5P)
<Tertiary Amination>

The dimesylated compound (0.50 g, 1.61 mmol) was dissolved in acetonitrile (13 ml) at 25° C., potassium carbonate (0.56 g, 4.02 mmol) was added and the mixture was stirred at 25° C. for 5 min. 5-(Isopropylamino)-1-pentanol (manufactured by Tokyo Chemical Industry) (2.34 g, 16.11 mmol) was added to the above-mentioned dimesylated compound/acetonitrile solution. At 16 hr after completion of dropwise addition, TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (2.44 g). The obtained brown liquid was dissolved in chloroform (24 ml), and washed with 5% aqueous sodium bicarbonate (24 ml). The aqueous layer was discarded, and washing with 5% aqueous sodium bicarbonate was performed twice to remove the starting material, 5-(isopropylamino)-1-pentanol. The chloroform layer was recovered, and the solvent was evaporated by an evaporator to give a transparent brown liquid (hereinafter di-IAP compound) (0.47 g).

<Acylation>

The di-IAP compound (0.40 g, 0.98 mmol) and D-α-tocopherol succinate (1.04 g, 1.96 mmol) were dissolved in chloroform (4 ml), DMAP (0.05 g, 0.39 mmol) and EDC (0.56 g, 2.94 mmol) was added, and the mixture was reacted at 30° C. for 4 hr. TLC analysis (eluent: chloroform/methanol=9/1 (v/v)) confirmed disappearance of the di-IAP compound and the reaction was completed. The solvent was evaporated by an evaporator to give a liquid (1.34 g). The liquid was purified by silica gel column chromatography (eluent: chloroform/methanol=99/1 (v/v)) to give the object product, TS-05P compound (0.60 g).

Results of $^1$H-NMR (400 MHz CDCl$_3$) Analysis

δ 0.83~0.90 ppm (m, C$\underline{H}_3$)$_2$—CH—, —CH$_2$—(C$\underline{H}_3$—)CH—CH$_2$—, 24H), δ 0.95~0.99 ppm (d, —N—CH(C$\underline{H}_3$) 12H), δ 1.00~1.80 ppm (m, —C(O)—O—CH$_2$—C$\underline{H}_2$—C$\underline{H}_2$—CH$_2$—CH$_2$—, CH$_3$—CH(CH$_3$)—(C$\underline{H}_2$)$_3$—C$\underline{H}$(CH$_3$)—(C$\underline{H}_2$)$_3$—C$\underline{H}$(CH$_3$)—(C$\underline{H}_2$)$_3$—, —O—C(C$\underline{H}_3$)—, —C=C—CH$_2$—C$\underline{H}_2$—, 64H), δ 1.95~2.10 ppm (s, —C=C(C$\underline{H}_3$)—, 18H), δ 2.37~2.42 ppm (t, —CH$_2$—CH$_2$—CH$_2$—C$\underline{H}_2$—N—, 4H), δ 2.56~2.59 ppm (t, —CH$_2$—C$\underline{H}_2$—C=C—O—, 4H), δ 2.69~2.78 ppm (m, —N—C$\underline{H}_2$—CH$_2$—S—, Ph-O—C(O)—C$\underline{H}_2$—CH$_2$—C(O)—O—, 12H), δ 2.85~2.95 ppm (m, Ph-O—C(O)—CH$_2$—C$\underline{H}_2$—C(O)—O—, —N—C$\underline{H}$(CH$_3$)$_2$, 6H), δ 4.05~4.15 ppm (t, —C(O)—O—C$\underline{H}_2$—CH$_2$—CH$_2$—, 4H)

[Example 8]
(Synthesis of TS-P2C1)
<Tertiary Amination>

The dimesylated compound (1.20 g, 3.87 mmol) was dissolved in acetonitrile (31 ml) at 25° C., potassium carbonate (1.34 g, 9.66 mmol) was further added and the mixture was stirred at 25° C. for 5 min. 2-Piperidinemethanol (manufactured by Tokyo Chemical Industry) (4.45 g, 38.66 mmol) was added to the above-mentioned dimesylated compound/acetonitrile solution, and the mixture was reacted at 40° C. for 13 hr. TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (3.90 g). The obtained brown liquid was dissolved in chloroform (39 ml), and washed with 10% brine (39 ml). The aqueous layer was discarded, and washing with 10% brine was repeated 5 times to remove the starting material, 2-piperidinemethanol. The chloroform layer was recovered, and the solvent was evaporated by an evaporator to give a transparent brown liquid (hereinafter di-2PM compound) (1.19 g).

<Acylation>

The di-2PM compound (0.80 g, 2.30 mmol) and D-α-tocopherol succinate (2.56 g, 4.82 mmol) were dissolved in chloroform (8 ml), DMAP (0.11 g, 0.92 mmol) and EDC (1.32 g, 6.89 mmol) were added, and the mixture was reacted at 30° C. for 4 hr. TLC analysis (eluent: chloroform/methanol=9/1 (v/v)) confirmed disappearance of the di-2PM compound, and the reaction was completed. The solvent was evaporated by an evaporator to give a liquid (2.93 g). The liquid was purified by silica gel column chromatography (eluent: chloroform/methanol=99/1 (v/v)) to give the object product, TS-P2C1 compound (0.58 g).

Results of $^1$H-NMR (400 MHz CDCl$_3$) Analysis

δ 0.83~0.88 ppm (m, (C$\underline{H}_3$)$_2$—CH—, —CH$_2$—(C$\underline{H}_3$)CH—CH$_2$—, 24H), δ 1.02~1.80 ppm (m, C$\underline{H}_3$—C$\underline{H}$(C$\underline{H}_3$)—(C$\underline{H}_2$)$_3$—C$\underline{H}$(CH$_3$)—(C$\underline{H}_2$)$_3$—C$\underline{H}$(CH$_3$)—(C$\underline{H}_2$)$_3$—, —CH—N—CH$_2$—CH$_2$—CH$_2$—CH$_2$—, —O—C(C$\underline{H}_3$)—, —C=C—CH$_2$—CH$_2$—, 64H), δ 1.95~2.10 ppm (s, —C=C(C$\underline{H}_3$)—, 18H), δ 2.30~2.36 ppm (m, —C(O)—O—CH$_2$—C$\underline{H}$—, 2H), δ 2.55~2.60 ppm (m, —CH$_2$—C$\underline{H}_2$—C=C—O—, —N—C$\underline{H}^{(a)}$$_2$—CH$_2$—CH$_2$—, 6H), δ 2.76~2.94 ppm (m, —N—C$\underline{H}_2$—C$\underline{H}_2$—S—, Ph-O—C(O)—C$\underline{H}_2$—C$\underline{H}_2$—C(O)—O—, 16H), δ 2.96~3.07 ppm (m, —N—C$\underline{H}^{(a)}$$_2$—CH$_2$—CH$_2$—, 2H), δ 4.12~4.27 ppm (m, —C(O)—O—C$\underline{H}_2$—CH—, 4H)

[Example 9]

(Synthesis of TS-P3C1)

<Tertiary Amination>

The dimesylated compound (1.20 g, 3.87 mmol) was dissolved in acetonitrile (31 ml) at 25° C., potassium carbonate (1.34 g, 9.66 mmol) was further added, and the mixture was stirred at 25° C. for 5 min. 3-Piperidinemethanol (manufactured by Tokyo Chemical Industry) (4.45 g, 38.66 mmol) was added to the above-mentioned dimesylated compound/acetonitrile solution and the mixture was reacted at 30° C. for 6 hr. TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (4.12 g). The obtained brown liquid was dissolved in chloroform (41 ml), and washed with 10% brine (41 ml). The aqueous layer was discarded, and washing with 10% brine was repeated 5 times to remove the starting material, 3-piperidinemethanol. The chloroform layer was recovered, and the solvent was evaporated by an evaporator to give a transparent brown liquid (hereinafter di-3PM compound) (1.30 g).

<Acylation>

The di-3PM compound (0.60 g, 1.72 mmol) and D-α-tocopherol succinate (1.92 g, 3.62 mmol) were dissolved in chloroform (6 ml), DMAP (0.08 g, 0.69 mmol) and EDC (0.99 g, 5.16 mmol) were added, and the mixture was reacted at 30° C. for 7 hr. TLC analysis (eluent: chloroform/methanol=9/1 (v/v)) confirmed disappearance of the di-3PM compound, and the reaction was completed. The solvent was evaporated by an evaporator to give a liquid (1.89 g). The liquid was purified by silica gel column chromatography (eluent: chloroform/methanol=98/2 (v/v)) to give the object product, TS-P3C1 compound (0.70 g).

Results of $^1$H-NMR (400 MHz CDCl$_3$) Analysis

δ 0.83~0.88 ppm (m, (C$\underline{H}_3$)$_2$—CH—, —CH$_2$—(C$\underline{H}_3$)CH—CH$_2$—, 24H), δ 1.02~1.88 ppm (m, CH$_3$—C$\underline{H}$(CH$_3$)—(C$\underline{H}_2$)$_3$—C$\underline{H}$(CH$_3$)—(C$\underline{H}_2$)$_3$—C$\underline{H}$(CH$_3$)—(C$\underline{H}_2$)$_3$—, —C$\underline{H}$—CH$_2$—N—CH$_2$C$\underline{H}_2$—C$\underline{H}_2$—, —O—C(C$\underline{H}_3$)—, —C=C—CH$_2$—CH$_2$—, 62H), δ1.90~2.10 ppm (m, —C=C(C$\underline{H}_3$)—, —CH—C$\underline{H}^{(a)}$$_2$—N—C$\underline{H}^{(a)}$$_2$—CH$_2$—, 22H), δ 2.55~2.60 ppm (t, —CH$_2$—C$\underline{H}_2$—C=C—O—, -4H), δ 2.63~2.66 ppm (m, —N—CH$_2$—C$\underline{H}_2$—S—, 4H), δ 2.73~2.85 ppm (m, —N—C$\underline{H}_2$—CH$_2$—S—, Ph-O—C(O)—C$\underline{H}_2$—CH$_2$—C(O)—O—, —CH—C$\underline{H}^{(e)}$$_2$—N—C$\underline{H}^{(e)}$$_2$—CH$_2$—, 12H), δ 2.90~2.95 ppm (t, Ph-O—C(O)—CH$_2$—C$\underline{H}_2$—C(O)—O—, 4H), δ 3.94~4.04 ppm (m, —C(O)—O—C$\underline{H}_2$—CH—, 4H)

[Example 10]

(Synthesis of TS-P4C1)

<Tertiary Amination>

The dimesylated compound (1.20 g, 3.87 mmol) was dissolved in acetonitrile (31 ml) at 25° C., potassium carbonate (1.34 g, 9.66 mmol) was further added and the mixture was stirred at 25° C. for 5 min. 4-Piperidinemethanol (manufactured by Tokyo Chemical Industry) (4.45 g, 38.66 mmol) was added to the above-mentioned dimesylated compound/acetonitrile solution, and the mixture was reacted at 30° C. for 4 hr. TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (4.25 g). The obtained brown liquid was dissolved in chloroform (42 ml), and washed with 10% brine (42 ml). The aqueous layer was discarded, and washing with 10% brine was repeated 3 times to remove the starting material, 4-piperidinemethanol. The chloroform layer was recovered, and the solvent was evaporated by an evaporator to give a transparent brown liquid (hereinafter di-4PM compound) (1.21 g).

<Acylation>

The di-4PM compound (0.60 g, 1.72 mmol) and D-α-tocopherol succinate (1.92 g, 3.62 mmol) were dissolved in chloroform (6 ml), DMAP (0.08 g, 0.69 mmol) and EDC (0.99 g, 5.16 mmol) were added, and the mixture was reacted at 30° C. for 7 hr. TLC analysis (eluent: chloroform/methanol=9/1 (v/v)) confirmed disappearance of the di-4PM compound, and the reaction was completed. The solvent was evaporated by an evaporator to give a liquid (1.90 g). The liquid was purified by silica gel column chromatography (eluent: chloroform/methanol=98/2 (v/v)) to give the object product, TS-P4C1 compound (1.26 g).

Results of $^1$H-NMR (400 MHz CDCl$_3$) Analysis

δ 0.83~0.88 ppm (m, (C$\underline{H}_3$)$_2$—CH—, —CH$_2$—(C$\underline{H}_3$—)CH—CH$_2$—, 24H), δ 1.02~1.74 ppm (m, CH$_3$—C$\underline{H}$(CH$_3$)—(C$\underline{H}_2$)$_3$—C$\underline{H}$(CH$_3$)—(C$\underline{H}_2$)$_3$—C$\underline{H}$(CH$_3$)—(C$\underline{H}_2$)$_3$—, —N—CH$_2$—C$\underline{H}_2$—CH—, —O—C(C$\underline{H}_3$)—, —C—C=C—CH$_2$—CH$_2$—, 62H), δ1.90~2.10 ppm (m, —C=C(C$\underline{H}_3$)—, —N—C$\underline{H}^{(a)}$$_2$—CH$_2$—CH—, 22H), δ 2.55~2.60 ppm (t, —CH$_2$—C$\underline{H}_2$—C=C—O—, -4H), δ 2.63~2.67 ppm (m, —N—CH$_2$—C$\underline{H}_2$—S—, 4H), δ 2.74~2.77 ppm (t, Ph-O—C(O)—C$\underline{H}_2$—CH$_2$—C(O)—O—, 4H), δ 2.81~2.84 ppm (m, —N—C$\underline{H}_2$—CH$_2$—S—, 4H), δ 2.90~2.95 ppm (m, —N—C$\underline{H}^{(e)}$$_2$—CH$_2$—CH—, Ph-O—C(O)—CH$_2$—C$\underline{H}_2$—C(O)—O—, 8H), δ 3.95~3.98 ppm (d, —C(O)—O—C$\underline{H}_2$—CH—, 4H)

[Example 11]
(Synthesis of TS-P4C2)
<Tertiary Amination>

The dimesylated compound (0.90 g, 2.90 mmol) was dissolved in acetonitrile (27 ml) at 25° C., potassium carbonate (1.00 g, 7.25 mmol) was further added and the mixture was stirred at 25° C. for 5 min. 4-Piperidineethanol (manufactured by Tokyo Chemical Industry) (3.75 g, 28.99 mmol) was added to the above-mentioned dimesylated compound/acetonitrile solution, and the mixture was reacted at 30° C. for 4 hr. TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (3.50 g). The obtained brown liquid was dissolved in chloroform (35 ml), and washed with 10% brine (35 ml). The aqueous layer was discarded, and washing with 10% brine was repeated 5 times to remove the starting material, 4-piperidineethanol. The chloroform layer was recovered, and the solvent was evaporated by an evaporator to give a transparent brown liquid (hereinafter di-4PE compound) (1.18 g).

<Acylation>

The di-4PE compound (0.70 g, 1.86 mmol) and D-α-tocopherol succinate (1.97 g, 3.72 mmol) were dissolved in chloroform (7 ml), DMAP (0.09 g, 0.74 mmol) and EDC (0.99 g, 5.58 mmol) were added, and the mixture was reacted at 30° C. for 9 hr. TLC analysis (eluent: chloroform/methanol=9/1 (v/v)) confirmed disappearance of the di-4PE compound, and the reaction was completed. The solvent was evaporated by an evaporator to give a liquid (2.09 g). The liquid was purified by silica gel column chromatography (eluent: chloroform/methanol=98/2 (v/v)) to give the object product, TS-P4C2 compound (1.14 g).

Results of $^1$H-NMR (400 MHz CDCl$_3$) Analysis

δ 0.83~0.88 ppm (m, (CH$_3$)$_2$—CH—, —CH$_2$—(CH$_3$)CH—CH$_2$—, 24H), δ 1.00~1.81 ppm (m, CH$_3$—CH(CH$_3$)—(CH$_2$)$_3$—CH(CH$_3$)—(CH$_2$)$_3$—CH(CH$_3$)—(CH$_2$)$_3$—, —N—CH$_2$—CH$_2$—CH—, —O—C(CH$_3$)—, —C=C—CH$_2$—CH$_2$—, —C(O)—O—CH$_2$—CH$_2$—CH—, 66H), δ 1.95~2.10 ppm (m, —C=C(CH$_1$)—, —N—CH$^{(a)}$$_2$—CH$_2$—CH—, 22H), δ 2.55~2.60 ppm (t, —CH$_2$—CH$_2$—C=C—O—, -4H), δ 2.62~2.66 ppm (m, —N—CH$_2$—CH$_2$—S—, 4H), δ 2.73~2.77 ppm (t, Ph-O—C(O)—CH$_2$CH$_2$—C(O)—O—, 4H), δ 2.80~2.84 ppm (m, —N—CH$_2$—CH$_2$—S—, 4H), δ 2.86~2.95 ppm (m, —N—CH$^{(e)}$$_2$—CH$_2$—CH—, —O—C(O)—CH$_2$—CH$_2$—C(O)—O—, 8H), δ 4.12~4.17 ppm (t, —C(O)—O—CH$_2$—CH$_2$—CH—, 4H)

[Example 12]
(Synthesis of TS-P4C3)
<Tertiary Amination>

The dimesylated compound (0.80 g, 2.58 mmol) was dissolved in acetonitrile (20 ml) at 25° C., potassium carbonate (0.89 g, 6.44 mmol) was further added and the mixture was stirred at 25° C. for 5 min. 4-Piperidinepropanol (manufactured by Accela ChemBio) (1.11 g, 7.73 mmol) was added to the above-mentioned dimesylated compound/acetonitrile solution, and the mixture was reacted at 30° C. for 21 hr. TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (2.27 g). The obtained brown liquid was dissolved in chloroform (23 ml), and washed with 5% aqueous sodium hydrogen carbonate (23 ml). The aqueous layer was discarded, and further washing once with 5% sodium bicarbonate water was performed to remove the starting material, 4-piperidinepropanol. The chloroform layer was recovered, and the solvent was evaporated by an evaporator to give a transparent brown liquid (hereinafter di-4PP compound) (0.70 g).

<Acylation>

The di-4PP compound (0.60 g, 1.48 mmol) and D-α-tocopherol succinate (1.57 g, 2.97 mmol) were dissolved in chloroform (6 ml), DMAP (0.07 g, 0.59 mmol) and EDC (0.85 g, 4.45 mmol) were added, and the mixture was reacted at 30° C. for 4 hr. TLC analysis (eluent: chloroform/methanol=9/1 (v/v)) confirmed disappearance of the di-4PP compound, and the reaction was completed. The solvent was evaporated by an evaporator to give a liquid (1.89 g). The liquid was purified by silica gel column chromatography (eluent: chloroform/methanol=99/1 (v/v)) to give the object product, TS-P4C3 compound (1.01 g).

Results of $^1$H-NMR (400 MHz CDCl$_3$) Analysis

δ 0.83~0.88 ppm (m, (CH$_3$)$_2$—CH—, —CH$_2$—(CH$_3$)CH—CH$_2$—, 24H), δ 1.05~1.83 ppm (m, CH$_3$—CH(CH$_3$)—(CH$_2$)$_3$—CH(CH$_3$)—(CH$_2$)$_3$—CH(CH$_3$)—(CH$_2$)$_3$—, —N—CH$_2$—CH$_2$—CH—, —O—C(CH$_3$)—, —C=C—CH$_2$—CH$_2$—, —C(O)—O—CH$_2$—CH$_2$—CH—, 70H), δ 1.95~2.10 ppm (m, —C=C(CH$_3$), —N—CH$^{(a)}$$_2$—CH$_2$—CH—, 22H), δ 2.55~2.60 ppm (t, —CH$_2$—CH$_2$—C=C—O—, -4H), δ 2.62~2.66 ppm (m, —N—CH$_2$—CH$_2$—S—, 4H), δ 2.73~2.77 ppm (t, Ph-O—C(O)—CH$_2$CH$_2$—C(O)—O—, 4H), δ 2.80~2.84 ppm (m, —N—CH$_2$—CH$_2$—S—, 4H), δ 2.86~2.95 ppm (m, —N—CH$^{(e)}$$_2$—CH$_2$—CH—, Ph-O—C(O)—CH$_2$—CH$_2$—C(O)—O—, 8H), δ 4.07~4.11 ppm (t, —C(O)—O—CH$_2$—CH$_2$—CH—, 4H)

[Example 13]
(Synthesis of TS-P4C4)
<Tertiary Amination>

The dimesylated compound (0.80 g, 2.58 mmol) was dissolved in acetonitrile (20 ml) at 25° C., potassium carbonate (0.89 g, 6.44 mmol) was further added and the mixture was stirred at 25° C. for 5 min. 4-Piperidinebutanol (manufactured by Accela ChemBio) (1.22 g, 7.73 mmol) was added to the above-mentioned dimesylated compound/acetonitrile solution and the mixture was reacted at 30° C. for 19 hr. TLC analysis (eluent: chloroform/methanol/28% aqueous ammonia=80/20/2 (v/v/v)) was performed to confirm completion of the reaction. Potassium carbonate was filtered off with filter paper (5A) and the solvent was evaporated by an evaporator to give a brown liquid (2.35 g). The obtained brown liquid was dissolved in chloroform (25 ml), and the mixture was washed with 5% aqueous sodium bicarbonate (25 ml). The aqueous layer was discarded, and further washing with 5% aqueous sodium bicarbonate was performed to remove the starting material, 4-piperidinebutanol. The chloroform layer was recovered, and the solvent was evaporated by an evaporator to give a transparent brown liquid (hereinafter di-4PB compound) (1.06 g).

<Acylation>

The di-4PB compound (0.60 g, 1.39 mmol) and D-α-tocopherol succinate (1.47 g, 2.77 mmol) were dissolved in chloroform (6 ml), DMAP (0.07 g, 0.56 mmol) and EDC (0.80 g, 4.16 mmol) were added, and the mixture was reacted at 30° C. for 4 hr. TLC analysis (eluent: chloroform/methanol=9/1 (v/v)) confirmed disappearance of the di-4PB compound, and the reaction was completed. The solvent was evaporated by an evaporator to give a liquid (1.88 g). The liquid was purified by silica gel column chromatography (eluent: chloroform/methanol=99/1 (v/v)) to give the object product, TS-P4C4 compound (0.80 g).

Results of $^1$H-NMR (400 MHz CDCl$_3$) Analysis

δ 0.83~0.88 ppm (m, (CH$_3$)$_2$—CH—, —CH$_2$—(CH$_3$)CH—CH$_2$—, 24H), δ 1.05~1.80 ppm (m, CH$_3$—CH(CH$_3$)—(CH$_2$)$_3$—CH(CH$_3$)—(CH$_2$)$_3$—CH(CH$_3$)—(CH$_2$)$_3$—, —N—CH$_2$—CH$_2$—CH—, —O—C(CH$_3$)—, —C=C—CH$_2$—CH$_2$—, —C(O)—O—CH$_2$—CH$_2$—CH$_2$—CH$_2$—CH—, 74H), δ 1.95~2.10 ppm (m, —C=C(CH$_3$)—, —N—CH$^{(a)}$$_2$—CH$_2$—CH—, 22H), δ 2.55~2.60 ppm (t, —CH$_2$—CH$_2$—C=C—O—, -4H), δ 2.62~2.66 ppm (m, —N—CH$_2$—CH$_2$—S—, 4H), δ 2.73~2.77 ppm (t, Ph-O—C(O)—CH$_2$—CH$_2$—C(O)—O—, 4H), δ 2.80~2.84 ppm (m, —N—CH$_2$CH$_2$—S—, 4H), δ 2.86~2.95 ppm (m, —N—CH$^{(e)}$$_2$—CH$_2$—CH—, Ph-O—C(O)—CH$_2$—CH$_2$—C(O)—O—, 8H), δ 4.06~4.11 ppm (t, —C(O)—O—CH$_2$—CH$_2$—CH—, 4H)

[Example 14]

(Synthesis of TG-C3M)

<Acylation>

The di-MAP compound (0.45 g, 1.52 mmol) and D-α-Tocopherol glutarate (1.65 g, 3.04 mmol) were dissolved in chloroform (5 ml), DMAP (0.07 g, 0.61 mmol) and EDC (0.87 g, 4.55 mmol) were added, and the mixture was reacted at 30° C. for 4 hr. TLC analysis (eluent: chloroform/methanol=9/1 (v/v)) confirmed disappearance of the di-MAP compound, and the reaction was completed. The solvent was evaporated by an evaporator to give a liquid (1.92 g). The liquid was purified by silica gel column chromatography (eluent: chloroform/methanol=98/2 (v/v)) to give the object product, TG-C3M compound (0.85 g).

Results of $^1$H-NMR (400 MHz CDCl$_3$) Analysis

δ 0.85~0.9 ppm (m, (CH$_3$)$_2$—CH—, —CH$_2$—CH(CH$_3$)—CH$_2$—, 24H), δ 1.00~1.78 ppm (m, CH$_3$—CH(CH$_3$)—(CH$_2$)$_3$—CH(CH$_3$)—(CH$_2$)$_3$—CH(CH$_3$)—(CH$_2$)$_3$—, —C(O)O—CH$_2$—CH$_2$—CH$_2$—N—, —O—C(CH$_3$)—, —C=C—CH$_2$—CH$_2$—, 56H), δ 1.95~2.15 ppm (s, —C=C(CH$_3$)—, Ph-O—C(O)—CH$_2$—CH$_2$—C(O)—, 22H), δ 2.22~2.26 ppm (s, —N(CH$_3$)—, 6H), δ 2.42~2.50 ppm (m, Ph-O—C(O)—CH$_2$—CH$_2$—CH$_2$—C(O)—O—, —O—CH$_2$—CH$_2$—CH$_2$—N—, 8H), δ 2.56~2.60 ppm (t, —CH$_2$—CH$_2$—CH=CH—, 4H), δ 2.66~2.70 ppm (m, —N—CH$_2$—CH$_2$—S—, Ph-O—C(O)—CH$_2$—CH$_2$—CH$_2$—C(O)—O—, 8H), δ 2.78~2.82 ppm (m, —N—CH$_2$—CH$_2$—S—, 4H), δ 4.14~4.17 ppm (t, —C(O)—O—CH$_2$—CH$_2$—CH$_2$—N—, 4H)

[Example 15]

(Synthesis of TSamide-C3M)

<Amidation>

To D-α-tocopherol succinate (10 g) were added 15-fold weight of chloroform and 2.0 equivalent amount of 3-bromopropylamine bromate (manufactured by Tokyo Chemical Industry), and 1.5 equivalent amount of EDC hydrochloride (manufactured by Tokyo Chemical Industry) was added by portions. After reaction at room temperature for 2 hr, the reaction mixture was washed 3 times with 10-fold weight of 20 wt % aqueous NaCl solution, and dried over magnesium sulfate. The solvent was evaporated by an evaporator to give a yellow viscous liquid (hereinafter TS amide compound) (7.7 g).

<Secondary Amination>

To the TS amide compound (2.7 g) was added 10 equivalent amount of 2M methylamine/THF solution (manufactured by Tokyo Chemical Industry) and the mixture was reacted at 40° C. for 18 hr. The reaction mixture was washed 3 times with 10-fold weight of 20 wt % aqueous NaCl solution, and dried over magnesium sulfate. The solvent was evaporated by an evaporator. The obtained brown solid (2.6 g) was purified by silica gel column chromatography (eluent: chloroform/methanol=99/1 (v/v)) to give a brown solid (0.64 g) (hereinafter secondary amino compound).

<Tertiary Amination>

To the secondary amino compound (0.64 g) were added 15-fold weight of acetonitrile, 0.10 equivalent amount of dimesylated compound, and 0.10 equivalent amount of potassium carbonate and the mixture was reacted at 40° C. for 18 hr. After the reaction, the solvent was evaporated by an evaporator and the residue was purified by silica gel column chromatography (eluent: chloroform/methanol=98/2-90/10 (v/v)) to give the object compound, TSamide-C3M compound (0.10 g).

Results of $^1$H-NMR (400 MHz CDCl$_3$) Analysis

δ 0.85~0.90 ppm (m, (CH$_3$)$_2$—CH—, —CH$_2$—CH(CH$_3$)—CH$_2$—, 24H), δ 1.00~1.83 ppm (m, CH$_3$—CH(CH$_3$)—(CH$_2$)$_3$—CH(CH$_3$)—(CH$_2$)$_3$—CH(CH$_3$)—(CH$_2$)$_3$—, —NH—CH$_2$—CH$_2$—CH$_2$N(CH$_3$)—, —O—C(CH$_3$)—, —C=C—CH$_2$—CH$_2$—, 56H), δ 1.95~2.15 ppm (s, —C=C(CH$_3$)—, 18H), δ 2.20~2.30 ppm (s, —N(CH$_3$)—, 6H), δ 2.40~2.50 ppm (t, —NH—CH$_2$—CH$_2$—CH$_2$—N—), δ 2.50~2.63 ppm (m, —CH$_2$—CH$_2$—CH=CH—, Ph-OC(O)—CH$_2$—CH$_2$—C(O)NH—, 8H), δ 2.63~2.70 ppm (t, —N(CH$_3$)—CH$_2$—CH$_2$—S—, 4H), δ 2.70~2.85 ppm (m, —N(CH$_3$)—CH$_2$—CH$_2$—S—, 4H), δ 2.85~3.00 ppm (t, Ph-OC(O)—CH$_2$—CH$_2$—C(O)NH—, 4H), δ 3.30~3.40 ppm (t, —NH—CH$_2$—CH$_2$—CH$_2$—N—, 4H), δ 6.85~6.95 ppm (t, —NH—CH$_2$—CH$_2$—CH$_2$—N—, 2H)

[Comparative Example 1]

(Synthesis of B-2-1)

With an intention to compare with the present invention having a disulfide bond, a compound wherein the disulfide bond in the compound of Example 1 was substituted by a carbon bond was synthesized.

<Tertiary Amination>

1,6-Dibromohexane (manufactured by Tokyo Chemical Industry) (6.0 g, 24.6 mmol) was dissolved in DMF (12.7 ml), 3-(methylamino)-1-propanol (manufactured by Tokyo Chemical Industry) (6.6 g, 73.7 mmol) and potassium carbonate (1.7 g, 12.3 mmol) were added, and the mixture was stirred at 20-25° C. for 3 hr. The progress of the reaction was confirmed by TLC (eluent: chloroform/methanol/28% aqueous ammonia solution=80/20/2 (v/v/v)). Potassium carbonate in the reaction mixture was filtered off using filter paper (5A), and the solvent was evaporated by an evaporator to give a brown liquid. The obtained brown liquid was dissolved in chloroform (20 ml), and the mixture was extraction-washed with water (30 g). The solvent in the organic layer was evaporated by an evaporator to give a brown liquid (3.6 g).

<Acylation>

The obtained liquid (2.0 g) (mmol) and myristic acid (4.0 g, 18.4 mmol) were dissolved in chloroform (20 ml), and DMAP (0.37 g, 3.0 mmol) and EDC (4.4 g, 23.1 mmol) were added. At 4 hr after the reaction, TLC analysis (eluent: chloroform/methanol=85/15 (v/v)) was performed. The results confirmed disappearance of the starting material, with which the reaction was terminated. Thereafter, the reaction mixture was extraction-washed with 5% sodium bicarbonate water (10 g), and the aqueous layer was discarded. Then, to the recovered organic layer was added water (10 g) to wash the layer with water. The aqueous layer was discarded, and sodium sulfate (2 g) was added to the organic layer to perform a dehydrating treatment. Insoluble materials were filtered off by filtration using Opuraito and filter paper (5A), and the solvent was evaporated by an evaporator. The obtained concentrated product was dissolved in hexane (47 ml), and the mixture was extraction washed with acetonitrile (39 ml). The hexane layer was recovered, and the solvent was evaporated by an evaporator to give the object product, compound B-2-1 (2.83 g).

Results of $^1$H-NMR (400 MHz CDCl$_3$) Analysis

δ 0.85~0.9 ppm (t, C$\underline{H}_3$—CH$_2$—, 6H), δ 1.22~1.35 ppm (m, CH$_3$—(C$\underline{H}_2$)$_{10}$—, —N(CH$_3$)—CH$_2$—CH$_2$—C$\underline{H}_3$—, 44H), δ 1.40~1.50 ppm (m, —N(CH$_3$)—CH$_2$—C$\underline{H}_2$—CH$_2$—, 4H), δ 2.37~2.41 (t, —N(CH$_3$)—C$\underline{H}_2$—CH$_2$—CH$_2$—, 4H), δ 4.08~4.12 (t, —CH$_2$—C(O)—O—C$\underline{H}_2$—, 4H)

[Experimental Example 1] Preparation of Various MENDs (1) Formation of Nucleic Acid Electrostatic Complex Composed of Plasmid DNA (pDNA) and Protamine A solution of pDNA encoding luciferase gene and protamine (CALBIOCHEM) solution were diluted with 10 mM HEPES buffer to 0.3 mg/mL and 0.05 mg/mL, respectively. While stirring 0.3 mg/mL pDNA (125 μL), 0.24 mg/mL protamine (125 μL) was added dropwise in small portions to prepared an electrostatic complex of protamine and pDNA (N/P ratio=1.2) as a core of the vector. In the method described in the following (2), 10 mM HEPES buffer (pH 5.3) was used and, in the method described in (3), 10 mM HEPES buffer (pH 7.4) was used.

(2) Preparation of MEND by Ethanol Dilution Method

A lipid solution in ethanol was prepared by mixing 5 mM cationic lipid, 5 mM phospholipid and 5 mM cholesterol (Chol) at desired ratios to achieve 165 nmol total lipid in an Eppendorf tube, further adding various PEG lipids (1 mM solution in ethanol) in an amount corresponding to 3 mol % of the total lipid, and adding ethanol to achieve a total volume of 100 μL. While stirring the lipid solution in a vortex mixer, 100 μL of the nucleic acid electrostatic complex (10 mM HEPES; pH 5.3) prepared in [Experimental Example 1] (1) was quickly added, and thereafter 10 mM HEPES buffer (1.8 mL, adjusted to pH 5.3) was added to dilute the mixture to an ethanol concentration of 5%. The mixture was concentrated to about 50 μL by ultrafiltration using Amicon Ultra 4 (Millipore) under centrifugation conditions (room temperature, 2267 rpm, 20 min). Thereafter, it was diluted to 4 mL with 100 mM HEPES buffer (adjusted to pH 7.4), and again concentrated by centrifugation (2267 rpm, 20 min) under room temperature conditions. Finally, it was diluted with 10 mM HEPES buffer (pH 7.4) to a desired lipid concentration.

(3) Preparation of MEND by Simple Hydration Method

A solution of each lipid in chloroform (5 mM DOTAP 24.75 μL, 5 mM DOPE 33 μL, 5 mM Chol 24.75 μL) were mixed in a glass test tube at DOTAP:DOPE:Chol=3:4:3 to achieve 412.5 nmol total lipid. Ethanol was added to a total amount of 250 μL, and the mixture was dried under reduced pressure in a desiccator. The solvent was evaporated to give a lipid thin film. To the lipid thin film was added 250 μL of the gene electrostatic complex (in 10 mM HEPES; pH 7.4) prepared in [Experimental Example 1] (1) to a total lipid concentration of 1.65 mM, and the mixture was stood at room temperature for 10 min to allow for hydration, and sonicated by a sonicator (AIWA MEDICAL INDUSTRY CO., LTD.) for 1 min.

(4) Preparation of MEND Using Rhodamine-Labeled pDNA

Rhodamine-labeled pDNA was prepared using Label/IT CX-Rhodamine Labeling Kit (Mirus) according to the attached protocol. The concentration of the obtained rhodamine-labeled pDNA solution was calculated using Nano Drop (Thermo Scientific). For preparation of MEND encapsulating the rhodamine-labeled pDNA, the pDNA solution described in [Experimental Example 1] (1) was completely replaced by rhodamine-labeled pDNA, and the method described in [Experimental Example 1] (2), (3) was performed to prepare MEND.

(5) Preparation of MEND with Fluorescence-Labeled Lipid Membrane

[Experimental Example 1]

MEND with fluorescence-labeled lipid membrane was prepared by adding a solution of NBD-DOPE (Avanti Polar Lipids) in ethanol in an amount corresponding to 1 mol % of the total lipid during preparation of the MENDs described in (2), (3).

[Experimental Example 2]

Measurement of Particle Size, and Surface Potential of Various MENDs

The particle size and the surface potential were measured by the dynamic light scattering method (Zetasizer Nano; Malve Rn). The particle size and the surface potential of the various MENDs prepared by the preparation method of [Experimental Example 1] are shown in Table 3. The charge of B-2 and DODAP at physiological pH was in a preferable mode of −10 to +10 mV, whereas that of B-2-1 was +12.3, which is not less than +10 mV.

The surface potential of MEND using a known cationic lipid, DOTAP, was about +50 mV.

TABLE 3

| | size (nm) | PDI | zeta (mV) |
|---|---|---|---|
| cationic lipid:SOPE:Chol = 3:4:3 | | | |
| B-2 (Example 1) | 156.3 | 0.14 | −0.08 |
| B-2-1 (Comparative Example 1) | 150.3 | 0.07 | 12.4 |
| B-2-2 (Example 2) | 134.6 | 0.132 | −5.77 |
| B-2-3 (Example 3) | 148.7 | 0.091 | −7.97 |
| DODAP (Comparative Example 2) | 151.1 | 0.093 | −3.18 |
| cationic lipid:SOPE:Chol = 5:3:2 | | | |
| B-2 (Example 1) | 168.9 | 0.11 | −2.95 |
| B-2-1 (Comparative Example 1) | 147.8 | 0.084 | 12.3 |
| DODAP (Comparative Example 2) | 165.6 | 0.106 | 4.13 |
| DOTAP:DOPE:Chol = 3:4:3 | | | |
| DOTAP (Comparative Example 3) | 235.8 | 0.295 | 57.9 |

[Experimental Example 3]

Liposome Destabilization Test in Reductive Environment Evaluation of Lipid Membrane Instability Under Reductive Environment of Various MENDs Using TNS DTT was added to various MEND solutions to a final concentration of 10 mM and the mixtures were stood at 37° C. The fluorescence intensity was measured using TNS (6-(p-Toludino)-2-Naphthalene Sulfonic acid) at the time points of 0, 1, 2, 4, 8, 24 hr later. The MEND solutions were diluted to 0.5 mM. The 0.5 mM MEND solution (12 μL), 20 mM citrate buffer (186 μL, containing 150 mM NaCl, acidic pH (pH 4.0)), and 0.6 mM TNS (2 μL) were added to a 96-well plate for fluorescence measurement (Nunc), and the fluorescence intensity was measured at excitation wavelength 321 nm, detection wavelength 447 nm, at 37° C. As a control, MEND solution added with the same amount of 10 mM HEPES buffer free of DTT at 0 hr and stood for each time at 37° C. was used, and the fluorescence intensity was measured using TNS by the same treatment. The fluorescence intensity under reductive environment was divided by the fluorescence intensity of the control and used as an index of the destabilization of lipid membrane. The results are shown in FIG. 1.

As a result, attenuation of TNS fluorescence due to the DTT treatment was not observed in DODAP and B-2-1 not having a disulfide bond. On the other hand, B-2 showed disappearance of TNS fluorescence in a time-dependent manner. TNS is adsorbed, under an acidic environment of pH 4.0, to a particle surface having a positive surface potential via electrostatically interactions, and emits fluorescence according to the liposoluble environment of the lipid structure part of a liposome. The disappearance of fluorescence in B-2 in this result is considered to stem from the loss of liposoluble environment, and suggests collapse of the lipid membrane structure due to the degradation of lipid.

[Experimental Example 4]
Evaluation of Gene Expression and Intracellular Uptake Activity
(1) Evaluation of Intracellular Uptake Amount of MEND Using B-2 (Example 1), B-2-1 (Comparative Example 1), and DODAP (Comparative Example 2) as cationic lipids, MENDs having a composition of cationic lipid:SOPE: Chol=3:4:3 were prepared by the method described in [Experimental Example 1] (2). For the preparation, $PEG_{2000}DSG$ was used as PEG lipid, and MEND solutions corresponding to 0.55 mM of the lipid concentration were prepared. For cationic MEND, lipids having a composition of DOTAP (Comparative Example 3):DOPE:Chol:=3:4:3 were used, and the cationic MEND was prepared according to the method described in [Experimental Example 1] (3). The lipids of various MENDs were labeled with fluorescence according to the method described in [Experimental Example 1] (5).

Figure 2:
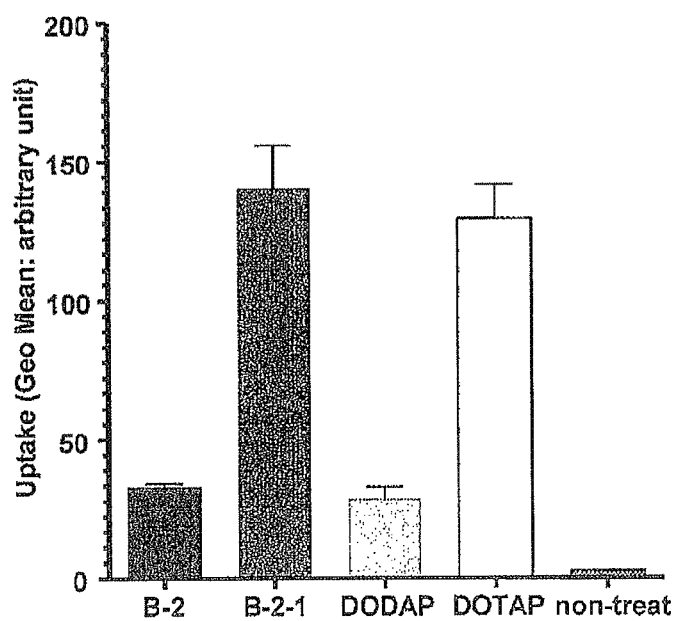
FIG. 2 shows the relative values of intracellular uptake of various MENDs prepared from B-2, B-2-1, DODAP or DOTAP.

HT1080 cells were plated on a 6-well plate at $2 \times 10^5$ cells/2 mL/well 24 hr before, various sample MENDs were diluted with DMEM (FBS+) to a lipid concentration of 27.5 nmol/1 mL/well and transfected into the well. After 1 hr, MEND-containing DMEM was removed, and the cells were washed twice with heparin (20 units/mL, 1 mL), and further once with PBS(−) (1 mL). 0.05% Trypsin solution (500 μL) was added, and the mixture was stood in an incubator at 37° C. for 3 min. DMEM (FBS+) (1 mL) was added and the mixture was centrifuged (700 g, 4° C., 5 min). The supernatant was removed and the cells were suspended in FACS buffer (1 mL). The suspension was centrifuged (700 g, 4° C., 5 min), the supernatant was removed and the cells were resuspended in FACS buffer (500 μL). The suspension was passed through a 44 μm nylon mesh immediately before the measurement, and the fluorescence intensity of intracellular NBD was measured. The results are shown in FIG. 2.

The lipid membrane in MEND was modified with fluorescence-labeled lipid, NBD-DOPE, and the intracellular uptake of MEND was evaluated. As a result, the uptake amount of the neutral particles B-2 and DODAP was extremely low as compared to the MENDs using B-2-1 and DOTAP which are cationic at a physiological pH (pH=7.4), though significantly higher than that of the non-treatment group (background).

(2) Evaluation of Gene Expression by MEND
Using B-2 (Example 1), B-2-1 (Comparative Example 1), and DODAP (Comparative Example 2) as cationic lipids, MENDs having a composition of cationic lipid:SOPE: Chol=3:4:3 were prepared by the method described in [Experimental Example 1] (2). For the preparation, $PEG_{2000}DSG$ was used as PEG lipid, and MEND solutions corresponding to 0.55 mM of the lipid concentration were prepared. For cationic MEND, lipids having a composition of DOTAP:DOPE:Chol:=3:4:3 were used, and the cationic MEND was prepared according to the method described in [Experimental Example 1] (3).

HT1080 cells were plated on a 24-well plate at $4 \times 10^4$ cells/500 μL/well 24 hr before, various MENDs were diluted with DMEM (FBS 10%+) to a pDNA amount of 0.4 μg/500 μL/well and transfected. 24 hr later, the cells were washed with PBS(−) (500 μL), 1× Lysis buffer was added to each well by 75 μL, and the mixture was stood at −80° C. for 30 min or longer. The frozen 24-well plate was thawed on ice, the cells were detached with a cell scraper, and the total amount thereof was transferred into an Eppendorf tube and centrifuged under the conditions of 15000 rpm, 4° C., 5 min. The supernatant (50 μL) was recovered in a different Eppendorf tube, and used for luciferase assay and BCA assay.

Figure 3:
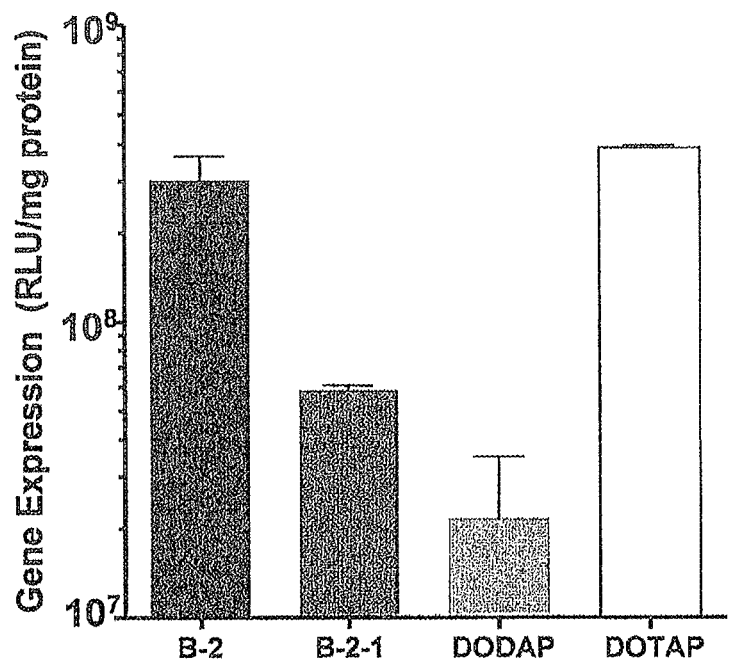
FIG. 3 shows the gene transfer activity of various MENDs prepared from B-2, B-2-1, DODAP or DOTAP.

20 μL thereof was mixed with a Luciferase assay substrate (50 μL), and the luciferase activity in a given time was measured by a luminometer. The obtained lysate was diluted 5-fold with DDW to achieve 25 μL total volume. Thereto was added BCA Protein Assay Reagent (200 μL), and the mixture was stood at 37° C. for 30 min. Thereafter, the absorbance at 562 nm was measured, and the protein amount of the sample was calculated from the absorbance of a BSA solution having a known concentration. The luciferase activity (RLU) was adjusted by dividing with protein amount (mg), and the luciferase activity per cell protein amount (RLU/mg protein) was calculated. The results are shown in FIG. 3.

The activity of MENDs formed from B-2 and B-2-1 exceeded that of a conventionally-known cationic lipid, DODAP. In addition, the activity of MEND prepared from B-2 was significantly higher than that of MEND prepared from B-2-1. Particularly, the activity equivalent to that of DOTAP, which is a conventionally-known cationic lipid, could be obtained in B-2.

Figure 4:
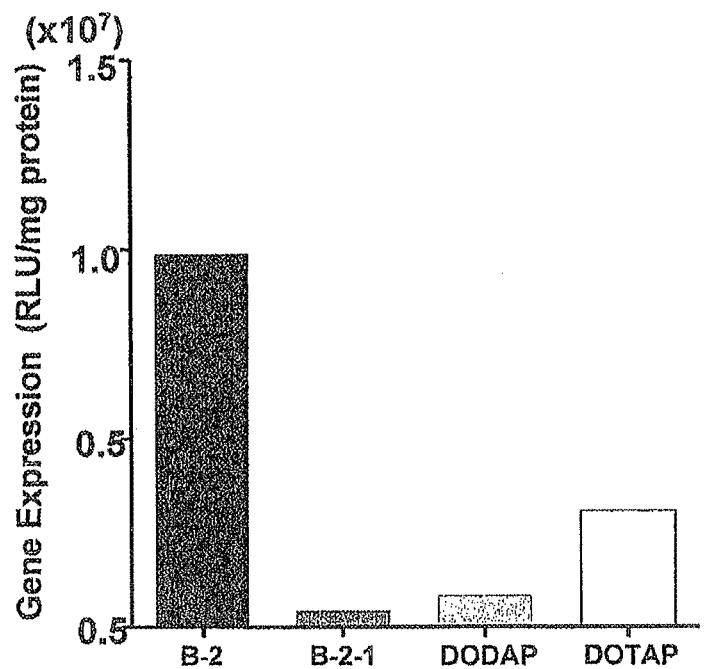
FIG. 4 shows the values of gene expression activity (FIG. 3) of various MENDs prepared from B-2, B-2-1, DODAP or DOTAP, standardized with the intracellular uptake amount (FIG. 4).

It has been clarified that MEND composed of B-2 shows a gene expression activity equivalent to that of MEND composed of cationic lipid DOTAP, even though it shows low uptake into the cell as compared thereto. The gene transfer activity is divided by the intracellular uptake amount obtained in [Experimental Example 4] (1), and the obtained values are shown in FIG. 4. Since the value of B-2 is high as compared to conventional DOTAP, DODAP and B-2-1 free of disulfide group, superior intracellular kinetic property after uptake into the cell is shown.

[Experimental Example 5]
Gene Expression Activity

Figure 5:
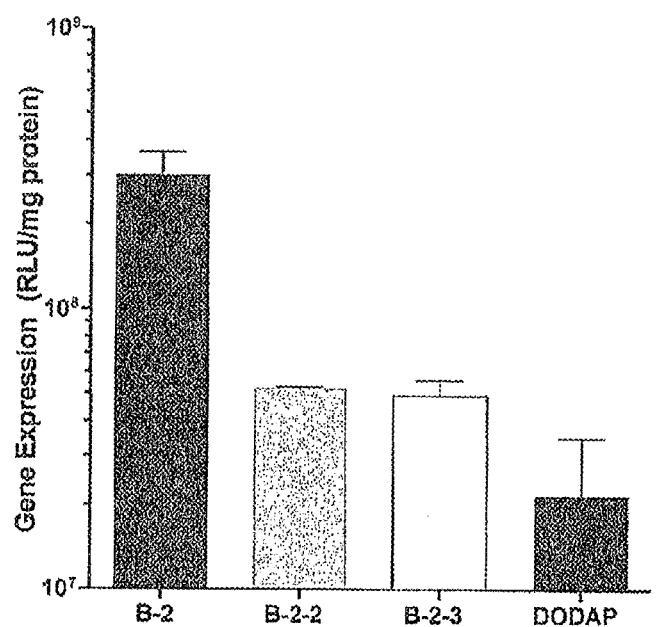
FIG. 5 shows the gene transfer activity of B-2 and derivatives thereof (B-2-2, B-2-3).

Using B-2 (Example 1), B-2-2 (Example 2), and B-2-3 (Example 3) as cationic lipids, MENDs having a composition of cationic lipid:SOPE:Chol=3:4:3 were prepared by the method described in [Experimental Example 1] (2). For the preparation, $PEG_{2000}DSG$ was used as PEG lipid, and MEND solutions corresponding to 0.55 mM of the lipid concentration were prepared. The gene expression was evaluated by the method described in [Example 4] (2). The results are shown in FIG. 5.

It has been clarified that the activity of MENDs formed from B-2-2 and B-2-3 is inferior to that of B-2, but exceeds that of conventional pH-responsive lipid cationic lipid, DODAP.

[Experimental Example 6]
Intracellular Kinetics (Endosomal Escape Efficiency)

For MEND preparation, the Rhodamine-labeled pDNA prepared by the method of [Experimental Example 1] (4)

was used. MEND having a composition of cationic lipid: SOPE:Chol=5:3:2 was prepared by the method described in [Experimental Example 1] (2). For the preparation, $PEG_{2000}$-DMG was used as PEG lipid, and MEND solutions corresponding to 0.55 mM of the lipid concentration were prepared. For cationic MEND, lipids having a composition of DOTAP (Comparative Example 3):DOPE:Chol:=3:4:3 were used, and the cationic MEND was prepared according to the method described in [Experimental Example 1] (3). In addition, cationic MEND having a lipid composition of DOTAP:DOPE:Chol:=3:4:3 was also prepared by a simple hydration method to have a lipid concentration of 0.55 mM.

Figure 6:
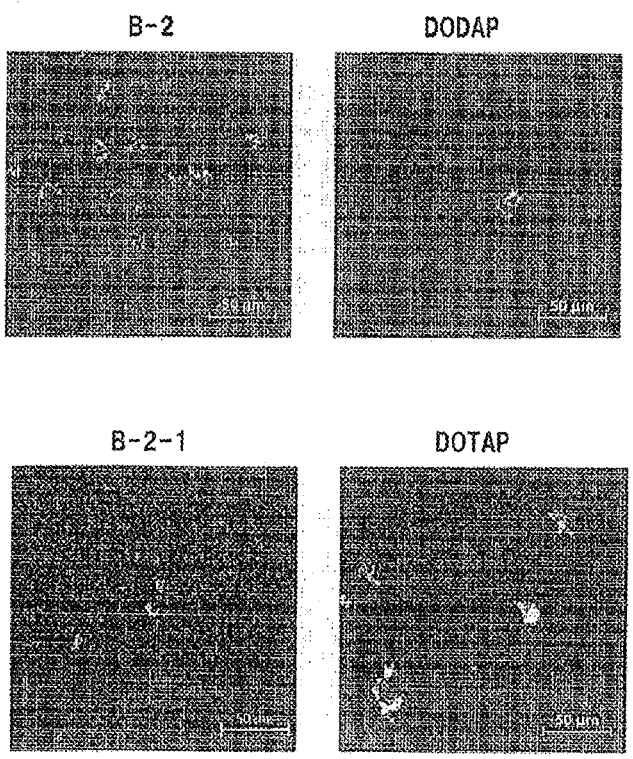
FIG. 6 shows the evaluation of escape of genes, introduced by various MENDs prepared from B-2, B-2-1, DODAP or DOTAP, from endosomes.
Figure 7:
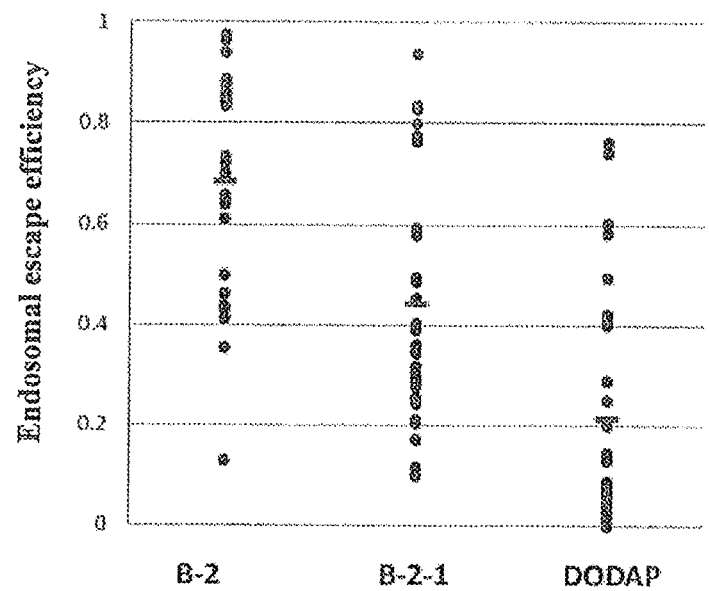
FIG. 7 is a graph showing the escape efficiency of genes introduced by various MENDs prepared from B-2, B-2-1, DODAP and DOTAP, from endosomes.

HT1080 cells were plated on a glass bottom dish at $1 \times 10^5$ cells/2 mL/dish 24 hr before. Since MENDs composed of B-2 or DODAP show low uptake activity into cells, MEND was diluted with Krebs buffer to pDNA 8 μg/1 mL Krebs buffer/dish. As for B-2-1 or DOTAP MEND having a high uptake activity, MEND was diluted with Krebs buffer to pDNA 1.6 μg/1 mL Krebs buffer/dish and transfected into the cells. After 2.5 hr, Lysotracker Green (Life technologies) was added at 1 μL/dish and, 30 min later, Hoechst 33342 (Dojindo) was further added at 1 μL/dish. 3 hr after the transfection, the cells were washed twice with heparin (20 units/mL, 2 mL), Krebs buffer (1 mL) was added, and the mixture was observed by a confocal laser scan microscope. The results are shown in FIG. 6. The results are quantified and shown in FIG. 7.

Rhodamine-labeled pDNA, endosome/lysosome, and nucleus were shown in pseudo colors of red, green and blue, respectively. The endosomal escape potency was evaluated by the colocalization of red and green. The red signal alone was present in B-2, B-2-1 and DOTAP, which seemingly indicates high endosomal escape potency of each MEND. On the other hand, colocalization of red and green was notable in DODAP, and yellow dots were observed. Therefrom it was suggested that the endosomal escape potency is superior in MENDs formed using B-2 or B-2-1 as compared to MEND using DODAP. Furthermore, the gene endosomal escape efficiency was quantified to find higher efficiency in the order of DODAP<B-2-1<B-2.

[Experimental Example 7]
Intracellular Kinetics (Decapsulation Efficiency)

For MEND preparation, the Rhodamine-labeled pDNA prepared by the method of [Experimental Example 1] (4) was used. In addition, the fluorescence label of the lipid constituting MEND was measured by the method described in [Experimental Example 1] (3). MENDs having a composition of cationic lipid:SOPE:Chol=5:3:2 were prepared by the method described in [Experimental Example 1] (2). For the preparation, $PEG_{2000}$-DMG was used as PEG lipid, and MEND solutions corresponding to 0.55 mM of the lipid concentration were prepared. For cationic MEND, a lipid having a composition of DOTAP:DOPE:Chol:=3:4:3 was used, and the cationic MEND was prepared according to the method described in [Experimental Example 1] (3). Lipids having a composition of DOTAP:DOPE:Chol:=3:4:3 were used for the cationic MEND, which was prepared by the method described in [Experimental Example 1] (3).

Figure 8:
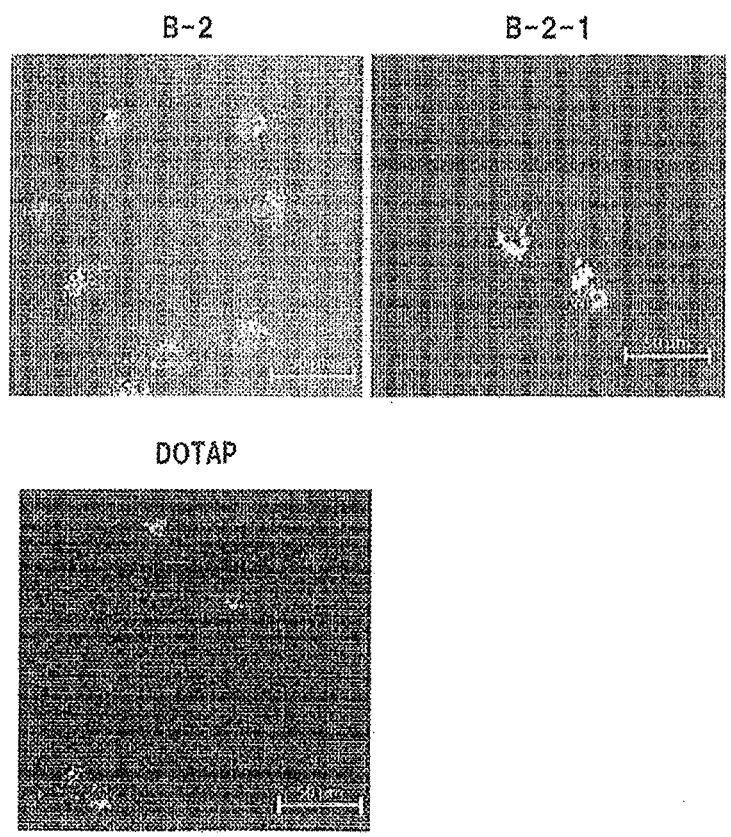
FIG. 8 shows the evaluation of decapsulation efficiency of genes introduced by various MENDs prepared from B-2, B-2-1 and DOTAP.

HT1080 cells were plated on a glass bottom dish at $1 \times 10^5$ cells/2 mL/dish 24 hr before. B-2 MEND was diluted with Krebs buffer to achieve pDNA 8 μg/1 mL Krebs buffer/dish. As for B-2-1 or DOTAP MEND, MEND was diluted with Krebs buffer to achieve pDNA 1.6 μg/1 mL Krebs buffer/dish and transfected. After 2.5 hr, Hoechst 33342 was added at 1 μL/dish and, 30 min later, the cells were washed twice with heparin solution (20 units/mL, 2 mL), Krebs buffer (1 mL) was added, and the cells were observed by a confocal laser scan microscope. The results are shown in FIG. 8.

Rhodamine-labeled pDNA, lipid membrane of MEND and nucleus were shown in pseudo colors of red, green and blue, respectively. Red dots were notable in B-2 and DOTAP, and the gene is considered to have been efficiently dissociated from MEND in the cell. On the other hand, B-2-1 showed clear colocalization of red and green, and almost all pDNAs were observed as yellow dots. Therefrom it is considered that the gene decapsulation efficiency of B-2 MEND is superior to that of B-2-1 MEND.

[Experimental Example 8]
Gene Expression Activity and Activity Duration In Vivo
(1) Preparation of MEND for In Vivo Administration A solution of pDNA encoding luciferase gene and protamine (maker) solution were diluted with 10 mM HEPES buffer to 0.3 mg/mL and 0.24 mg/mL, respectively. While stirring 0.3 mg/mL pDNA (400 μL), 0.23 mg/mL protamine solution (400 μL) was added dropwise in small portions to prepared an electrostatic complex of protamine and pDNA (N/P ratio=1.2) as a core of the vector.

A lipid solution in ethanol was prepared by mixing 5 mM B-2, 5 mM SOPC, and 5 mM Chol at a ratio of B-2:SOPC:Chol=3:4:3 to achieve 165 mM total lipid in an Eppendorf tube. Furthermore, $PEG_{2000}$-DSG was added as PEG lipid in an amount corresponding to 10 mol % of the total lipid, and ethanol was added to achieve the total volume of 750 μL. A solution (750 μL) of the electrostatic complex composed of gene and protamine was mixed with the lipid solution (750 μL), and the mixture was quickly stirred, diluted with 10 mM HEPES solution (pH 5.3) to 15 mL, and subjected to ultrafiltration using Amicon® Ultra-15 100K device at 3,000 rpm, 15 min, 25° C. The solution after ultrafiltration was diluted with 100 mM HEPES buffer (pH 7.4), and subjected to the ultrafiltration again. The solution was diluted with 10 mM HEPES buffer to 750 μL.

(2) Investigation of Time Dependency of Gene Expression Activity of B-2 MEND

Figure 9:
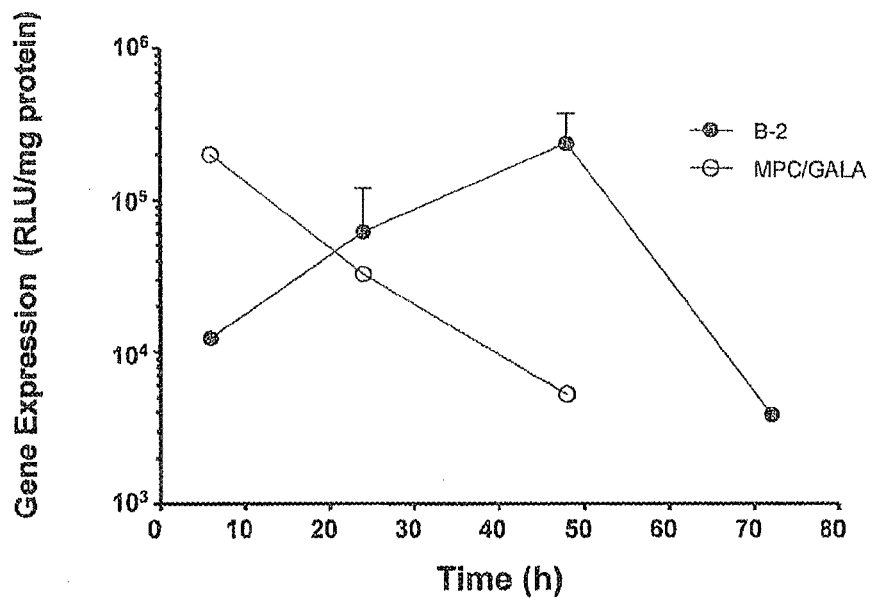
FIG. 9 shows the gene expression activity in the liver after intravenous administration of MENDs prepared from B-2 or cationic lipid.

A MEND solution prepared by the method shown in (1), and cationic MEND using MPC/GALA, which shows high gene expression in the liver (Ukawa et al., Biomaterials, 31(24) 6355-6362 (2010)), were each administered to 5-week-old male ICR mice from the tail vein in an amount corresponding to 40 μg DNA. The mice were euthanized by a cervical spine destaining method 6, 24, 48, 72 hr later, and the liver, lung and spleen were isolated and frozen with liquid nitrogen. They were thawed in a Lysis buffer to prepare homogenates. They were centrifuged at 13,000 rpm, 10 min, 4° C., and the supernatant was collected and used as a measurement sample. The sample solution (20 μL) was mixed with a luciferase substrate (50 μL), and the luciferase activity was measured using Luminescenser-PSN (AB2200 ATTO). In addition, the concentration of the protein in the sample was quantified using a BCA protein assay kit, and the gene expression activity was measured as RLU/mg protein. The results are shown in FIG. 9 and FIG. 10.

It was clarified that the cationic MEND using MPC/GALA showed a peak of gene expression activity 6 hr later, and thereafter showed a rapid decrease in the gene expression with time. The tendency was the same as that of general cationic lipoplex (Sakurai et al., Journal of Controlled Release 17 (2007) 430-437). On the other hand, B-2 MEND showed a gradual increase in the gene expression activity, which reached the maximum 48 hr later. These results suggest that B-2 MEND has superior expression sustainability to the conventional vector (FIG. 9).

Figure 10:
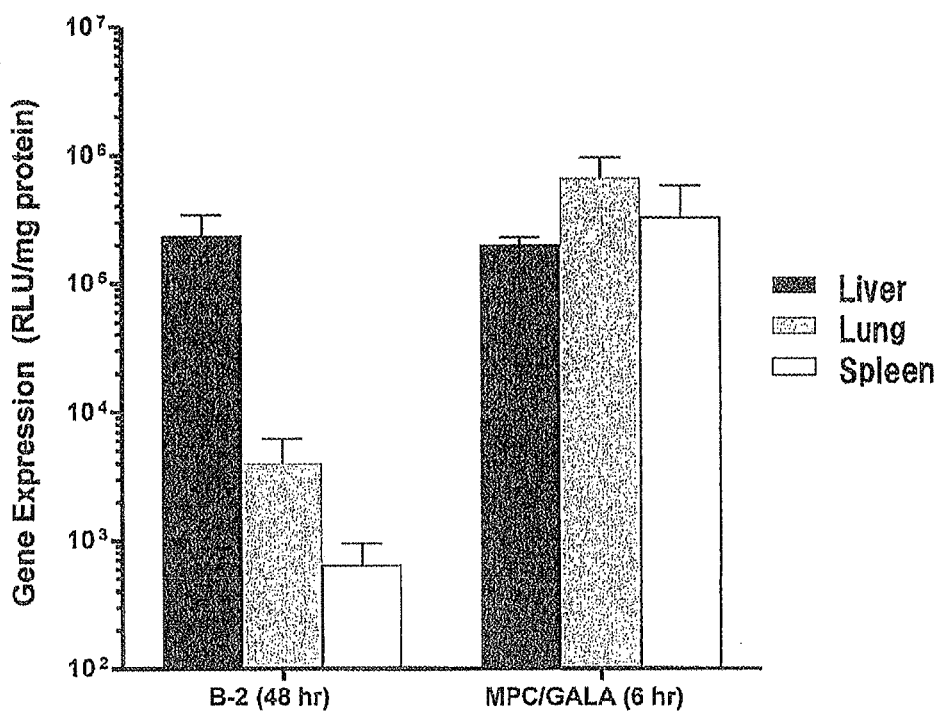
FIG. 10 shows the organ specificity of gene expression by MENDs prepared from B-2 or cationic lipid.

While conventional cationic MEND is poor in organ selectivity and shows a gene expression activity in the lung and spleen, which is of the same level as in the liver, B-2 MEND shows a background-level of gene expression activity in the lung and spleen and is superior in the organ selectivity (particularly, liver selectivity) (FIG. 10).

[Experimental Example 9]
Influence of Endosome and Lysosome Acidification Inhibition on Gene Expression Activity Using B-2 (Example 1), B-2-1 (Comparative Example 1), and DODAP (Comparative Example 2) as cationic lipids, MENDs having a composition of cationic lipid:SOPE:Chol=5:3:2 were prepared by the method described in [Experimental Example 1] (2). For the preparation, $PEG_{2000}$-DMG was used as PEG lipid, and MEND solutions corresponding to 0.55 mM of the lipid concentration were prepared. For cationic MEND, lipids having a composition of DOTAP (Comparative Example 3):DOPE:Chol:=3:4:3 were used, and the cationic MEND was prepared according to the method described in [Experimental Example 1] (3).

HT1080 cells were plated on a 24-well plate at $4 \times 10^4$ cell/500 µL/well 24 hr before, bafilomycin A1 was added at 0.5 µM 30 min before for a pre-treatment. Various MENDs were diluted with DMEM (FBS 10%+) to a pDNA amount of 0.4 µg/500 µL/well, bafilomycin A1 was added at 0.5 µM, and transfection was performed. 3 hr later, the MEND solution was removed, and DMEM (FBS 10%+) was added at 500 µL/well to change the medium. 24 hr later, the cells were washed with PBS(−) (500 µL), 1× Lysis buffer was added to each well by 75 µL, and the mixture was stood at −80° C. for 30 min or longer. The frozen 24-well plate was thawed on ice, the cells were detached with a cell scraper, and the total amount thereof was transferred into an Eppendorf tube and centrifuged under the conditions of 15000 rpm, 4° C., 5 min. The supernatant (50 µL) was recovered in a different Eppendorf tube, and used for luciferase assay and BCA assay. The gene expression was evaluated by the method described in [Example 4] (2).

Figure 11:
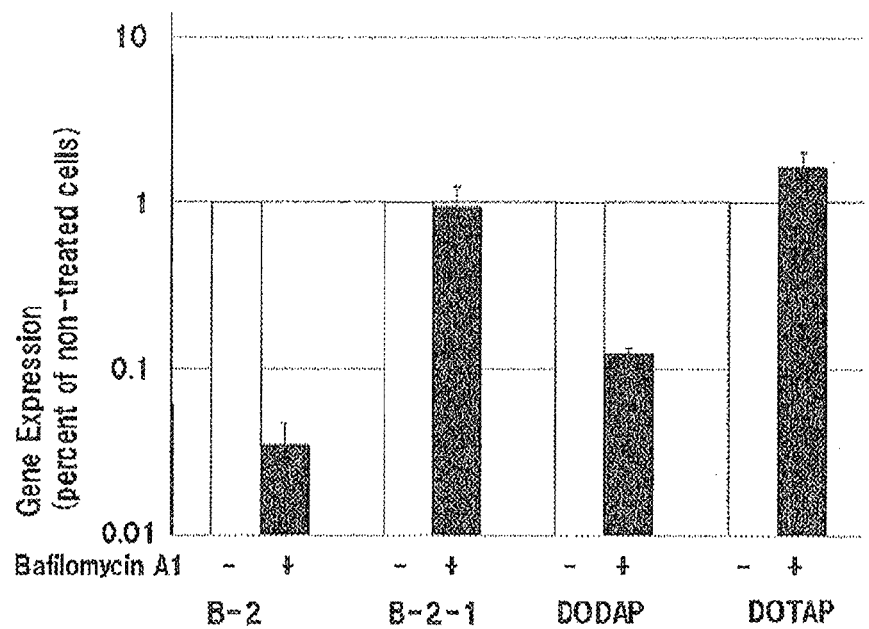
FIG. 11 is a graph showing the influence of endosome, lysosome acidification inhibition on the gene expression activity of various MENDs prepared from B-2, B-2-1, DODAP or DOTAP.

As a result, B-2-1 and DOTAP which are cationic under a physiological pH environment did not show a decrease in the gene expression activity. On the other hand, B-2, DODAP showed a decrease in the gene expression activity. These results suggest that positive charging of the lipid membrane by endosomal acidification contributes to the gene expression activity of B-2, DODAP (FIG. 11).

[Experimental Example 10]
Evaluation of Influence on In Vitro Translation Reaction
Evaluation of Inhibitory Effect on In Vitro Translation System Using Rabbit Reticulocyte Lysate Systems, Nuclease Treated (Promega KK)

MENDs having a composition of B-2:SOPE:Chol=5:3:2 were prepared by the method described in [Experimental Example 1] (2). For the preparation, $PEG_{2000}$-DMG was used as PEG lipid, and MEND solutions corresponding to 0.55 mM of the lipid concentration were prepared. For cationic MEND, lipids having a composition of DOTAP:DOPE:Chol:=3:4:3 were used, and the cationic MEND was prepared according to the method described in [Experimental Example 1] (3).

Luciferase-mRNA solution was diluted to 0.005 µg/µL. Various MEND solutions were added in 0.0625, 0.125, 0.25 µg relative to 1 µL of mRNA solution to adjust the total amount to 6.5 µL. A mixture of RRL (Rabbit Reticulocyte Lysate, 17.5 µL), AAM (Amino Acid Mixture)-Met (0.25 µL), AAM-Leu (0.25 µL), and RRI (Recombinant RNase Inhibitor, 0.5 µL) was added, and the mixture was stood at 30° C. for 90 min.

Figure 12:
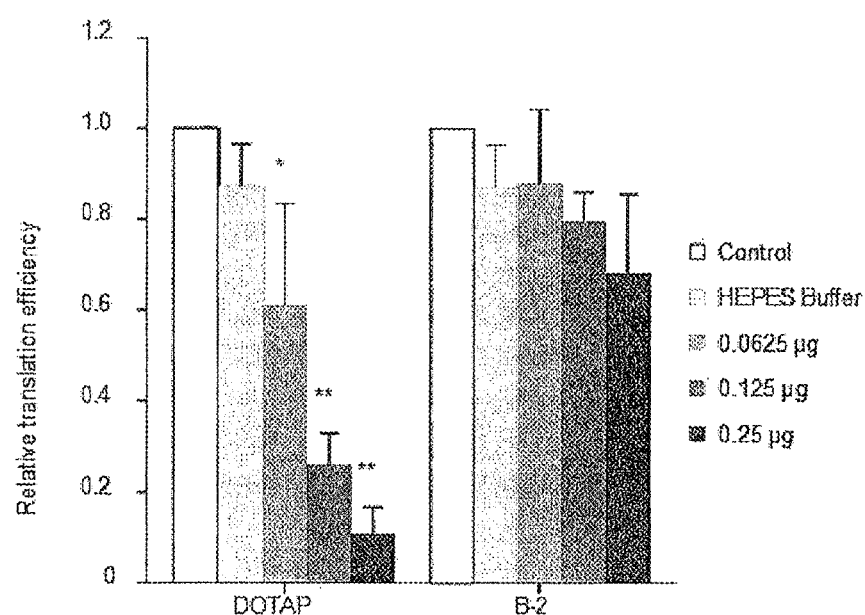
FIG. 12 is a graph showing the influence of various MENDs prepared from B-2 or DOTAP on in vitro translation reaction.

10 µL thereof was mixed with a Luciferase assay substrate (50 µL), and the luciferase activity in a given time was measured by a luminometer. The obtained reaction solution was diluted 500-fold with DDW to achieve the total volume of 25 µL. Thereto was added BCA Protein Assay Reagent (200 µL), and the mixture was stood at 37° C. for 30 min. Thereafter, the absorbance at 562 nm was measured, and the protein amount of the sample was calculated from the absorbance of a BSA solution having a known concentration. The luciferase activity (RLU) was adjusted by dividing with protein amount (mg), and the luciferase activity per cellular protein amount (RLU/mg protein) was calculated. The results are shown in FIG. 12.

As a result, a significant inhibitory effect on an in vitro translation reaction was observed in MEND using DOTAP. However, such effect was not observed in MEND using B-2. Therefrom B-2 is considered to show small intracellular interactions with the nucleic acid.

[Experimental Example 11]
Evaluation of Serum Resistance

MEND having a composition of B-2 (Example 1):SOPE:Chol=3:4:3 or B-2 (Example 1):SOPC:Chol=3:4:3 was prepared by the method described in [Experimental Example 1] (2). For the preparation, $PEG_{2000}$-DMG was used as PEG lipid, and MEND solution corresponding to 0.55 mM of the lipid concentration was prepared.

Blood samples were collected from the abdominal cavity of 4-week-old male ICR mice, and stood at room temperature for 30 min to allow for complete coagulation of the blood. Blood clot was detached from the wall by tapping, and centrifuged at 4,000 rpm, 15 min, 25° C., whereby the supernatant was recovered. Naked pDNA, Core, MEND solution and mouse serum were mixed to give 90% mouse serum, which was treated at 650 rpm and stood at 37° C. 0, 1, 3, 6, 24 hr later, the mixture was frozen by 70 µL at −20° C. and preserved. To the reaction mixture was diluted with water (210 µL), 280 µL of alkali phenol/chloroform/isoamylalcohol was added, and the mixture was vigorously stirred for about 30 seconds, centrifuged at 15,000 rpm, 15 min, 25° C., and the supernatant was recovered. 1% Agarose gel was used for the electrophoresis. A sample (12 µL) was mixed with 6× loading dye (2 µL), and the total amount was applied to the well to perform electrophoresis. The gel was stained by immersing in aqueous EtBr solution for 30 min and photographed.

Figure 13:
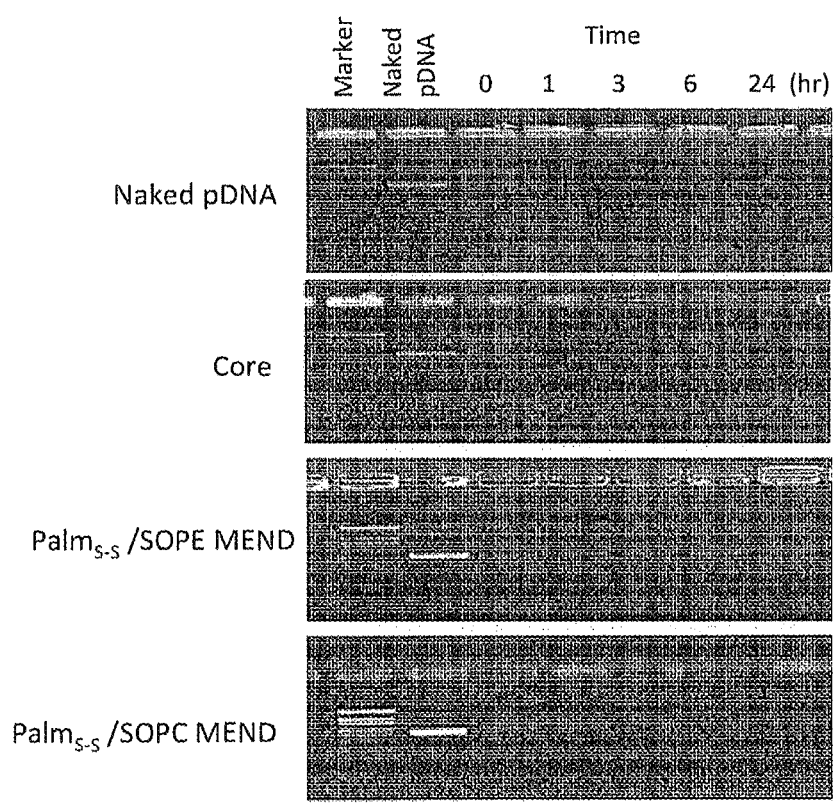
FIG. 13 shows the resistance effect of MEND, prepared from B-2, against degradation of nucleic acid by serum.

In Naked pDNA and Core, pDNA was lysed in 1 hr after mixing with serum, and the band was not observed. However, when they were prepared as MEND, the band was observed even 24 hr later. The results confirmed that MEND prepared using B-2 has serum resistance, and can prevent degradation of pDNA in the serum (FIG. 13).

Figure 14:
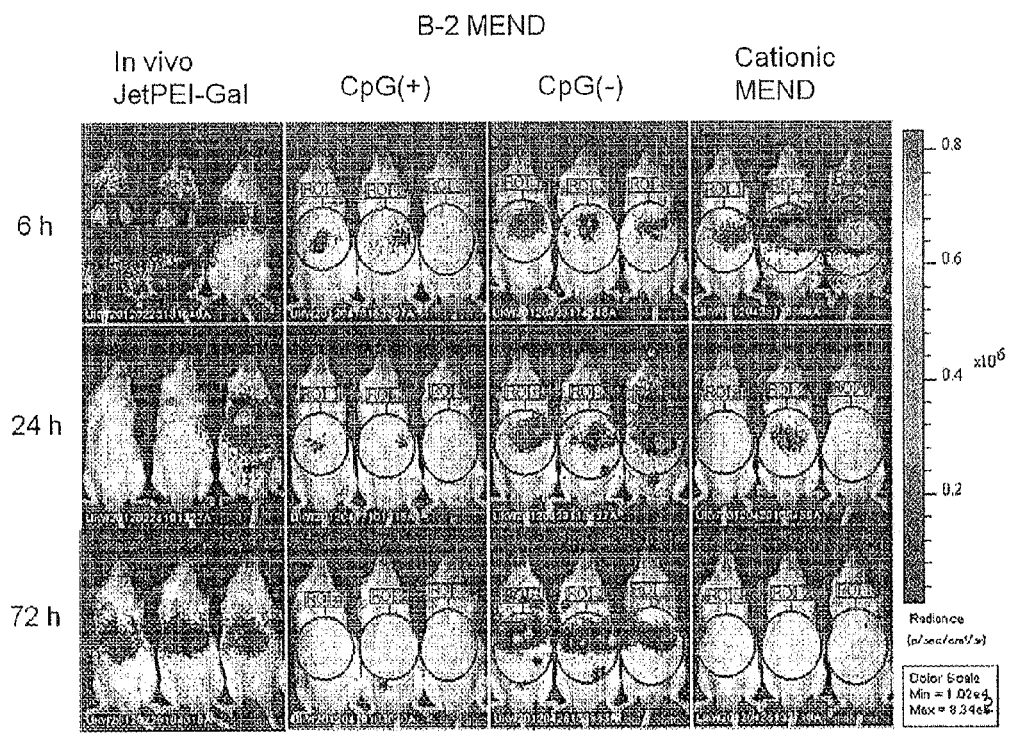
FIG. 14 shows time-course changes in the gene expression activity of an expression vector (CpG(+) or CpG(−)) introduced into the liver by intravenous administration of MEND prepared from B-2, MEND prepared from R8/GALA, or in vivo JetPEI-Gal.
Figure 14:
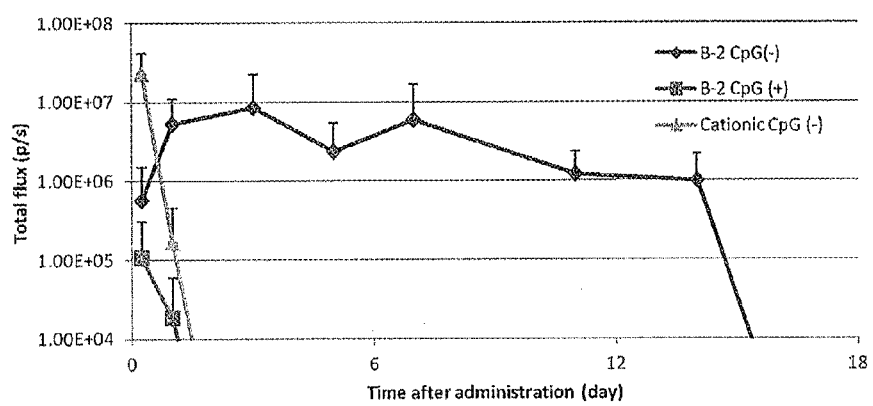

[Experimental Example 12]
Evaluation of Time Course Changes in Gene Expression Activity of B-2 MEND A MEND solution prepared by the method shown in Experimental Example 9, cationic MEND using R8/GALA, which shows high gene expression property in the liver (Khalil et al., J Control Release, 156(3) 374-80), and in vivo JetPEI-Gal (PolyPlus-Transfection) which is a commercially available transgene reagent targeting the liver were each administered to 5-week-old male ICR mice from the tail vein in an amount corresponding to 40 µg DNA. As a DNA to be mounted on MEND composed of B-2 in this case, pCpGfree-Luc(0) described in WO 2011/132713 was used as pDNA completely excluding CpG sequence known to induce immune response and, as a general pDNA having a CpG sequence, a plasmid DNA (pcDNA3.1-Luc(+); CpG sequence total 425) containing a CpG sequence in the back bone of the plasmid DNA and having a CpG sequence even between the initiation codon and the stop codon of the luciferase sequence (marker gene) was used. In gene transfer using cationic MEND and in vivo JetPEI-Gal, pCpGfree-Luc(0) alone was used. 6, 24, 72 hr later, luciferin (in vivo grade, Promega) corresponding to 3 mg was intraperitoneally administered to the mice, and imaging was performed using IVIS LuminaII (Caliper Life Sciences). As for MEND composed of B-2, imaging was performed about twice a week even after 72 hr. The total luminescence amount in the mouse abdomen was calculated as photon/sec from the obtained images, and used as an index of gene expression activity in the liver. The obtained images are shown in FIG. 14 (the upper panel) and a graph of the total luminescence amount is shown in FIG. 14 (the lower panel).

Cationic MEND using R8/GALA showed a strong luminescence 6 hr later, after which the gene expression rapidly decreased over time, and the luminescence was not seen at all 72 hr later. In vivo JetPEI-Gal showed very high lung-derived luminescence and low organ selectivity for the liver, particularly 6 hr later. Furthermore, the sustainability of the gene expression using this vector was also poor. On the other hand, B-2 MEND using pcDNA3.1-Luc(+) showed a weak luminescence 6 hr later, after which the gene expression decreased. When pCpGfree-Luc(0) was used, the luminescence amount increased from 6 hr to 24 hr later, after which the luminescence amount was retained for the subsequent one week, and the luminescence completely disappeared 18 days later. These results show that B-2 MEND combined with pDNA free of CpG sequence is superior in sustainability to the conventional type of carrier.

[Experimental Example 13]
Evaluation of Intrahepatic Behavior of MEND

Figure 15:
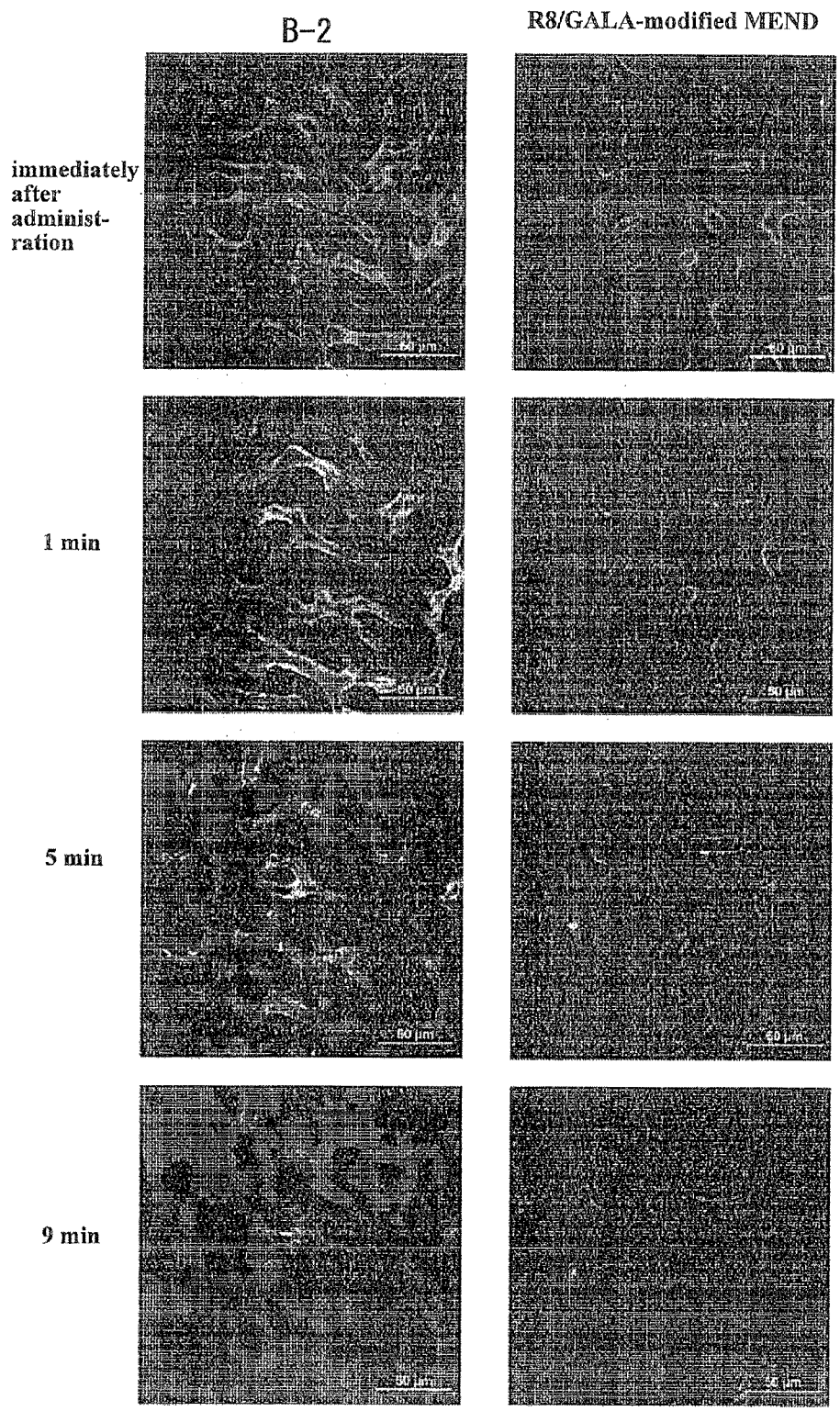
FIG. 15 presents photographs showing the behaviors of MEND prepared from B-2 and MEND prepared from R8/GALA in the liver.

MEND prepared by the method shown in Experimental Example 9, and cationic MEND using R8/GALA showing high gene expression in the liver (Khalil et al., J Control Release, 156(3) 374-80) were each labeled with fluorescence by adding Rhodamine-DOPE (Avanti polar lipids) to a lipid solution in the preparation stage. Rhodamine-DOPE was added to R8/GALA-MEND in an amount of 0.1% of the total lipid concentration, and to B-2 MEND in an amount of 1% of the total lipid concentration. 50 mg/mL Sodium pentobarbital (Nacalai Tesque) was diluted 5-fold with saline and intraperitoneally administered to ICR mice (5-week-old male) for anesthesia. *Griffonia simplicifolia* Lectin I-B4 Isolectin, FITC Conjugate (VECTOR Laboratories, about 80 μL) was administered to the mice under anesthesia from the tail vein to stain the vascular endothelial cells. The mice underwent laparotomy to expose the liver, and Immersol 518F (Carl Zeiss) was added dropwise to the organ to prevent the organ from drying. A winged intravenous indwelling needle connected with an extension tube filled with the MEND solution was indwelled in the tail vein of the mouse. To prevent dislocation of the observation site due to the heart beat of the mouse, a device for fixing the liver by adsorption (Shimizu K et al., J Biosci Bioeng. 112(5): 508-10) was used, and the mouse was observed using a confocal microscope (Nikon A1) with a 60-fold water immersion lens. MEND was administered to the mouse such that 40 μg DNA/mouse was achieved in about 5 seconds from the start of filming and the filming was finished in about 10 min. The results are shown in FIG. 15.

When MEND modified with R8/GALA was used, huge coagulation flowed into the blood of the liver and many particles were adsorbed mainly along the blood vessel walls, whereas when B-2 was used, it was observed that coagulation was not formed and the MEND uniformly flows through the blood vessels, as well as leaked out from the blood vessels with time and transferred into the liver.

Figure 16:
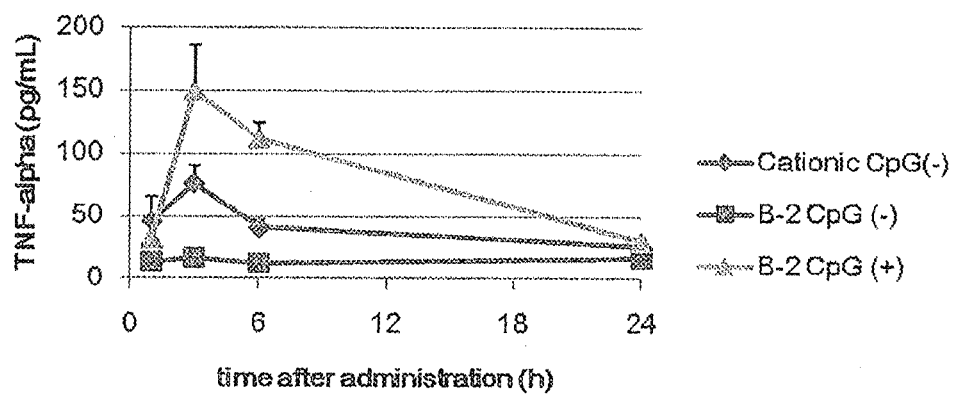
FIG. 16 presents graphs showing the concentration profiles of cytokine in the blood after administration of MEND prepared from B-2 or MEND prepared from R8/GALA, containing an expression vector (CpG(+) or CpG(−)).
Figure 16:
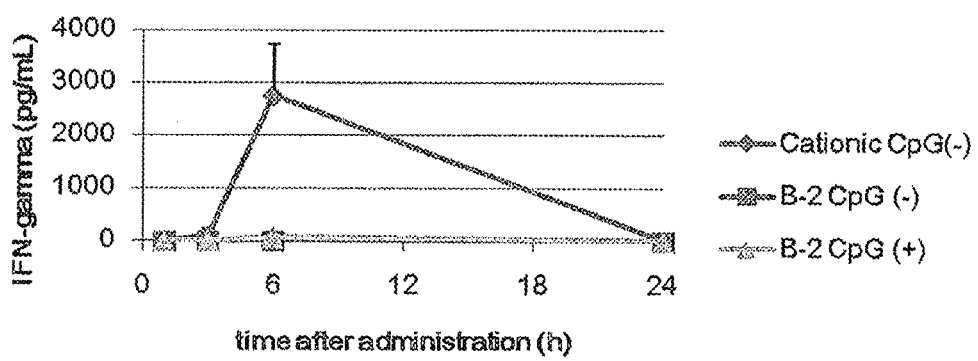
Figure 16:
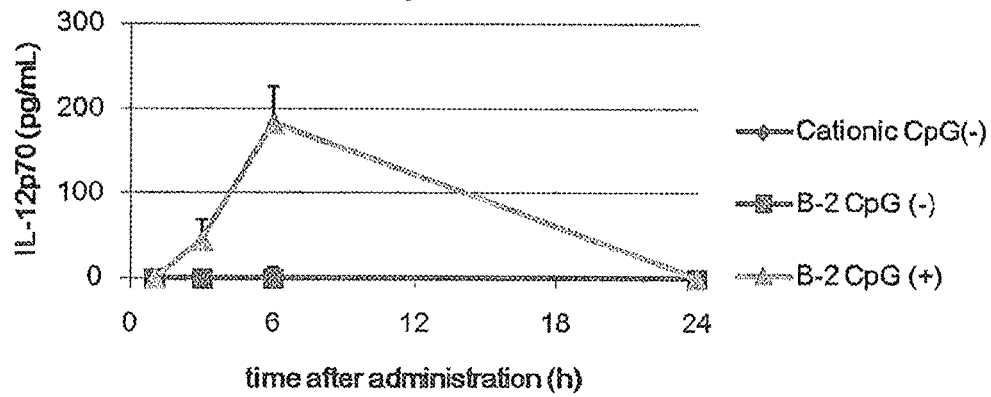

[Experimental Example 14]
Evaluation of Cytokine Production by MEND Administration MENDs used in [Experimental Example 12] were each administered to 5-week-old male ICR mice from the tail vein in an amount corresponding to 40 μg DNA. 1, 3, 6, 24 hr later, the blood was collected from the heart, and TNF-α, IFN-γ, IL-12p70 were measured using Quantikine ELISA kit (R&D Systems). Each blood concentration profile is shown in FIG. 16.

Cationic MEND showed a somewhat high TNF-α value 3 hr after administration, even though it contained pCpGfree-Luc(0), and IFN-γ value became high 6 hr later. On the other hand, B-2 MEND using pcDNA3.1-Luc(+) showed a high TNF-α value 3 hr later, and high IL-12p70 value 6-hr later. In the meantime, when pCpGfree-Luc(0) was introduced using B-2 MEND, 3 kinds of cytokines all maintained the normal value at any time point.

These results suggest that B-2 MEND prepared using pCpGfree-Luc(0) does not easily induce immune response. Therefore, it is considered that decrease in the gene expression activity due to immunity reaction, harmful side effects and the like do not occur easily.

[Experimental Example 15]
Preparation of MEND Using B-2-4, B-2-5

(1) MEND having a composition of B-2-4 (Example 4):DOPE:Chol=3:3:4 or B-2-5 (Example 5):POPE:Chol=3:4:3 was prepared according to the method described in [Experimental Example 1] (1) and (2).

(2) Preparation of MEND Using Cy5-Labeled pDNA

Cy5-labeled pDNA was prepared using Label/IT Cy5 Labeling Kit (Mirus) and according to the attached protocol. The concentration of the obtained Cy5-labeled pDNA solution was calculated using Nano Drop (Thermo Scientific). When MEND encapsulating Cy5-labeled pDNA was prepared, 10% of the pDNA solution described in [Experimental Example 1] (1) was replaced by Cy5-labeled pDNA, and MEND was prepared according to the method described in [Experimental Example 1] (2) and (3).

[Experimental Example 16]
Measurement of Particle Size and Surface Potential of Various MENDs The particle size and the surface potential were measured by the dynamic light scattering method (Zetasizer Nano; Malvern). The particle size and the surface potential of the various MENDs prepared by the preparation method of [Experimental Example 1] are shown in Table 4. Both B-2-4 and B-2-5 showed a preferable charge of −10 to +10 mV at physiological pH.

TABLE 4

|  | size (nm) | PDI | zeta (mV) |
| --- | --- | --- | --- |
| cationic lipid:DOPE:Chol = 3:3:4 | | | |
| B-2-4 (Example 4) | 146.7 | 0.12 | −7.22 |
| cationic lipid:POPE:Chol = 3:4:3 | | | |
| B-2-5 (Example 5) | 131.7 | 0.15 | −9.35 |

[Experimental Example 17]
Electron Microscope Observation by Staining Method

Figure 17:
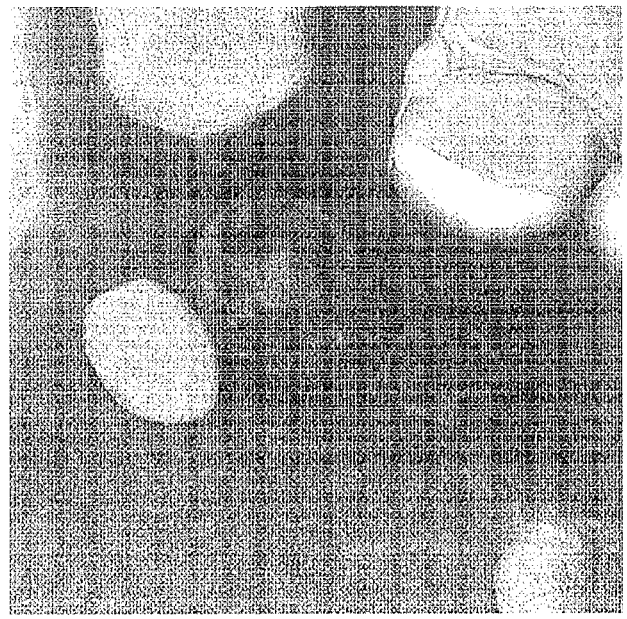
FIG. 17 shows electron micrographs of various MENDs prepared from B-2 or B-2-4.
Figure 17:
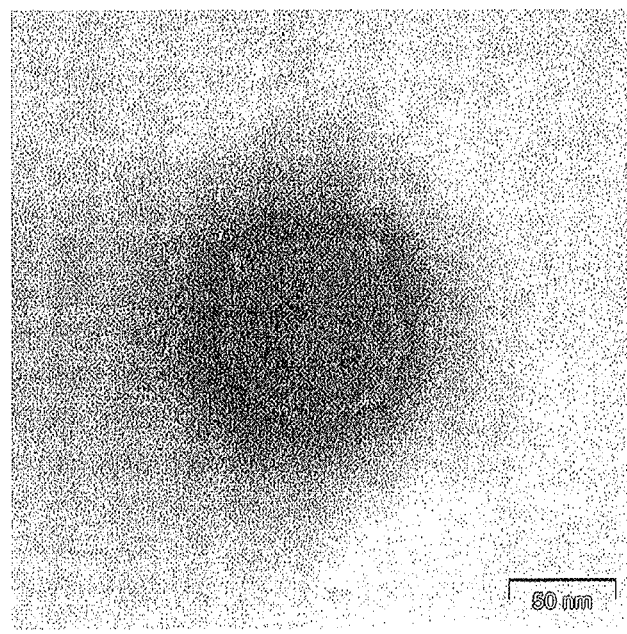

MENDs of B-2 (Example 1) and B-2-4 (Example 4) were prepared according to [Experimental Example 1] (1), (2) and [Experimental Example 15]. For the preparation, $PEG_{2000}$-DMG was used as PEG lipid, and MEND solutions corresponding to 1.38 mM of the lipid concentration were prepared. A 50% sucrose solution (pH 5.3) (5 mL) was added to a centrifugation tube, on which a 10% sucrose solution (pH 5.3) (5 mL) was layered, and a MEND solution (1.5 mL) was further overlaid to form an discontinuous density gradient. Purification was performed by ultracentrifugation (110000 g, 2 h, 25° C.) (Optima™ L-90K Ultracentrifuge, Sw41Ti, BECKMAN). The interface (4 ml) of sucrose density 10% and 50% was recovered, and sucrose was removed by ultrafiltration (1000 g, 3 min, 25° C.) to give a sample solution. A 2-fold diluted sample solution was adsorbed to a 400 mesh carbon film TEM grid, which was absorbed by a filter paper. A 2% phosphotungstic acid solution (pH 7.0) was added and the mixture was stood for 10 seconds. For observation, a transmission electron microscope (JEM-1200EX, JEOL Ltd.) was used. Accelerating voltage was set to 80 kV, and images were taken by a CCD camera (VELETA, JEOL Ltd.). The results are shown in FIG. 17.

In both B-2 in the upper panel and B-2-4 in the lower panel, a structure coated with a monolayer lipid membrane was observed.

[Experimental Example 18]
Evaluation of Gene Expression Activity

Using compositions of B-2-4 (Example 4):DOPE:Chol=3:3:4, B-2-5 (Example 5):POPE:Chol=3:3:4, B-2 (Example 1):SOPE:Chol=5:3:2 as lipids, MENDs were prepared according to [Experimental Example 1](1) and (2). For the preparation, $PEG_{2000}$-DMG was used as PEG lipid, and MEND solutions corresponding to 0.55 mM of the lipid concentration were prepared.

Figure 18:
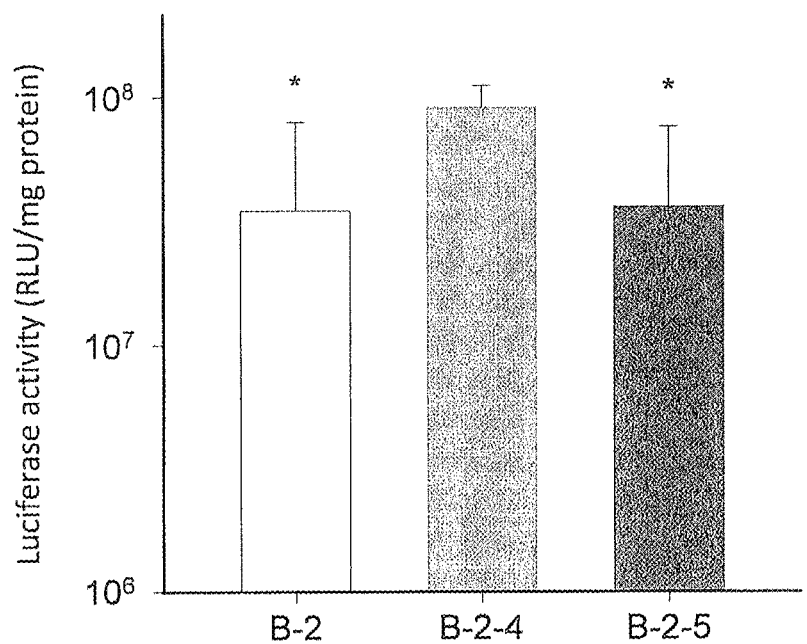
FIG. 18 is a graph showing the expression activity of genes introduced by various MENDs prepared from B-2, B-2-4 or B-2-5.

The gene expression activity was evaluated by the method described in [Experimental Example 4] (2). The results are shown in FIG. 18.

The activity of the MEND formed from B-2-5 was equivalent to the activity of B-2. The activity of the MEND formed from B-2-4 was significantly higher than the activity of B-2 and B-2-5.

[Experimental Example 19]
Time-Course Evaluation of Gene Expression Activity and Intracellular Uptake Amount
(1) Time-Course Observation of Intracellular Uptake Amount of MEND MENDs of B-2-4 (Example 4), B-2 (Example 1) were prepared according to [Experimental Example 1] (1), (2), [Experimental Example 15]. For the preparation, $PEG_{2000}$-DMG was used as PEG lipid, and MEND solutions corresponding to 0.55 mM of the lipid concentration were prepared. For cationic MEND, lipids having a composition of DOTAP (Comparative Example 3):DOPE:Chol:=3:4:3 were used, and the cationic MEND was prepared according to the method described in [Experimental Example 1] (3). pDNA was labeled with fluorescence according to the method described in [Experimental Example 15] (2).

Figure 19:
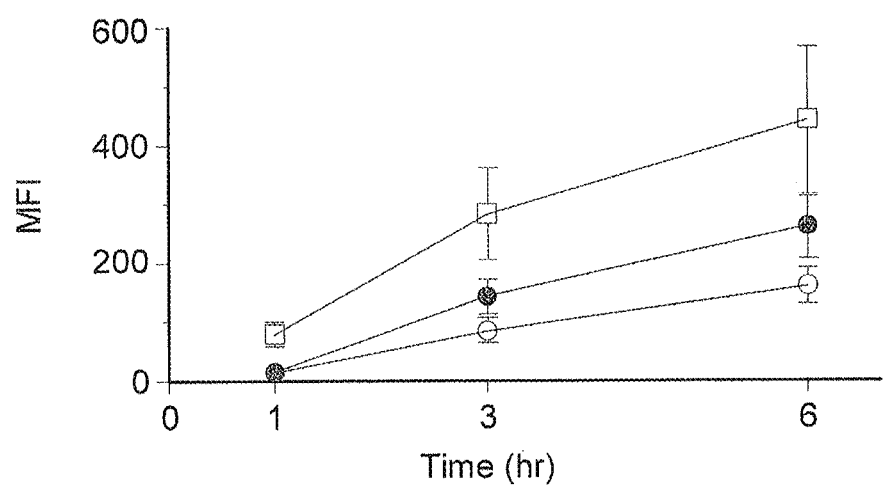
FIG. 19 is a graph showing the time-course changes in the intracellular uptake of various MENDs prepared from B-2, B-2-4 or DOTAP, wherein an open circle shows B-2, a closed circle shows B-2-4, and an open square shows DOTAP.

HT1080 cells were plated on a 6-well plate at $2 \times 10^5$ cells/2 mL/well 24 hr before, various sample MENDs were diluted with DMEM (FBS+) to a pDNA concentration of 1.6 µg/2 mL/well and transfected into the well. After 1, 3, 6 hr, MEND-containing DMEM was removed, and the cells were washed twice with heparin (20 units/mL, 1 mL), and further once with PBS(−) (1 mL). 0.05% Trypsin solution (500 µL) was added, and the cells were stood in an incubator at 37° C. for 3 min. DMEM (FBS+) (1 mL) was added and the mixture was centrifuged (700 g, 4° C., 5 min). The supernatant was removed and the cells were suspended in FACS buffer (1 mL). The suspension was centrifuged (700 g, 4° C., 5 min), the supernatant was removed and the cells were resuspended in FACS buffer (500 µL). The suspension was passed through a 44 µm nylon mesh immediately before the measurement, and the fluorescence intensity of intracellular Cy5 was measured. The results are shown in FIG. 19.

pDNA was fluorescently modified with Cy5, and the intracellular uptake by MEND was evaluated. As a result, the uptake amount of the neutral particles B-2 and B-2-4 was low as compared to the MENDs using DOTAP which is cationic at a physiological pH (pH=7.4). MEND using B-2-4 was more highly uptaken than B-2.

(2) Time-Course Evaluation of Gene Expression Using AB-2550 Kronos Dio (Atto)

MENDs of B-2-4 (Example 4), B-2 (Example 1) were prepared according to [Experimental Example 1] (1), (2), and [Experimental Example 18]. For the preparation, $PEG_{2000}$-DMG was used as PEG lipid, and MEND solutions corresponding to 0.55 mM of the lipid concentration were prepared. For cationic MEND, lipids having a composition of DOTAP (Comparative Example 3):DOPE:Chol:=3:4:3 were used, and the cationic MEND was prepared according to the method described in [Experimental Example 1] (3).

Figure 20:
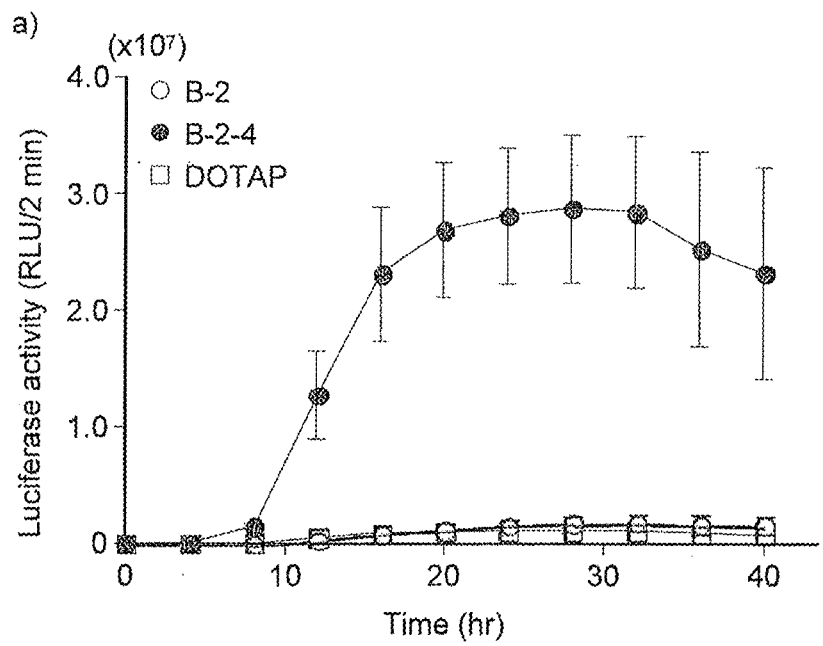
FIG. 20 is a graph showing the gene transfer activity of various MENDs prepared from B-2, B-2-4 or DOTAP.

HT1080 cells were plated on a 3.5 cm cell culture dish at $4 \times 10^4$ cells/2 mL/dish 24 hr before, various MENDs were diluted with DMEM (FES 10%+, Phenol red free) containing a final concentration of 200 µM of D-luciferin potassium to achieve 1.6 µg/2 mL/dish based on the pDNA amount and transfection was performed. According to the Kronos Dio package insert, the luminescence amount was measured for 2 min every 20 min and taken as the luciferase activity (RLU/2 min). The results are shown in FIG. 20.

The activity of MEND formed from B-2-4 was significantly higher than that of MENDs formed from B-2-1 and DOTAP. The activity of B-2 was equivalent to that of DOTAP.

It has been clarified that MEND composed of B-2-4 shows a significantly high gene expression activity as compared to that of MEND composed of cationic lipid DOTAP, even though it shows low uptake into the cell as compared thereto. It was shown that B-2-4 is further superior in the intracellular kinetic property after uptake into the cell as compared to B-2 and conventional DOTAP.

[Experimental Example 20]
Intracellular Kinetics (Endosomal Escape Efficiency)
(1) Evaluation of Endosomal Escape Efficiency For MEND preparation, the Rhodamine-labeled pDNA prepared by the method of [Experimental Example 1] (4) was used. When MEND encapsulating rhodamine-labeled pDNA was prepared, 50% of the pDNA solution described in [Experimental Example 1] (1) was replaced by rhodamine-labeled pDNA.

MENDs having a composition of B-2-4 (Example 4):DOPE:Chol=3:3:4, B-2 (Example 1):SOPE:Chol=5:3:2 were prepared by the method described in [Experimental Example 1] (2). For the preparation, $PEG_{2000}$-DMG was used as PEG lipid, and MEND solutions corresponding to 0.55 mM of the lipid concentration were prepared.

Figure 21:
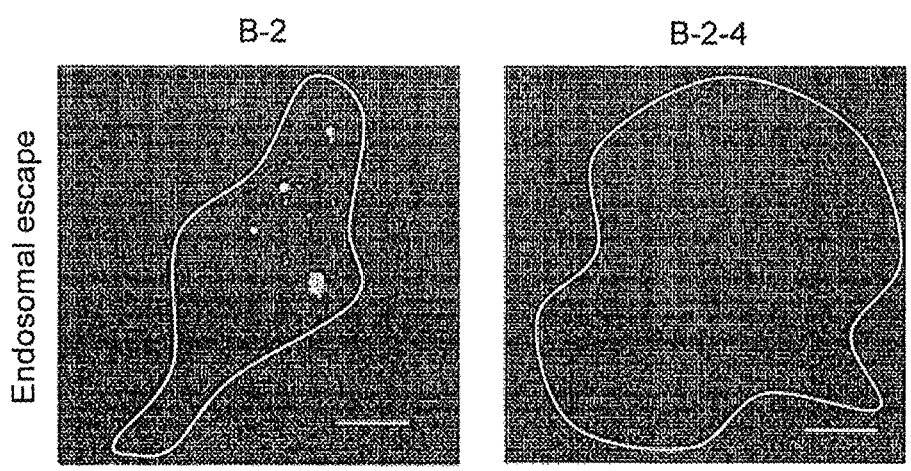
FIG. 21 presents photographs showing the intracellular kinetics of MEND prepared from B-2 and MEND prepared from B-2-4, which include rhodamine-labeled pDNA.

HT1080 cells were plated on a glass bottom dish at $5 \times 10^4$ cells/2 mL/dish 24 hr before. MEND was diluted with DMEM (FBS 10%+) to achieve pDNA 1.6 µg/2 mL and transfected into cells. After 5.5 hr, Lysotracker Green (Life technologies) was added at 2 µL/dish. 6 hr after the transfection, the cells were washed twice with heparin (20 units/mL, 2 mL), Krebs buffer (1 mL) was added, and the cells were observed by a confocal laser scan microscope. The results are shown in FIG. 21.

Rhodamine-labeled pDNA, endosome/lysosome and nucleus were shown in pseudo colors of red, green and blue, respectively. The endosomal escape efficiency was calculated according to the following formula.

$$\text{endosomal escape efficiency} = 1 - \frac{\text{intraendosomal gene amount (yellow pixel number)}}{\text{total gene amount (red pixel number)}}$$

Figure 22:
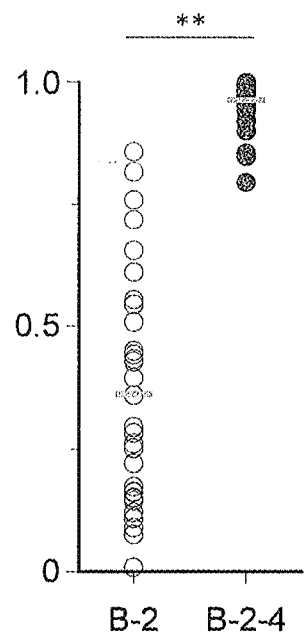
FIG. 22 is a graph showing the endosomal escape efficiency of genes introduced by various MENDs prepared from B-2 or B-2-4.

The results are shown in FIG. 22. It was clarified therefrom that B-2-4 shows significantly higher endosomal escape efficiency than B-2.

(2) Evaluation of Endosome Amount

MENDs having a composition of B-2-4 (Example 4):DOPE:Chol=3:3:4, B-2 (Example 1):SOPE:Chol=5:3:2 were prepared by the method described in [Experimental Example 1] (2). For the preparation, PEG$_{2000}$-DMG was used as PEG lipid, and MEND solutions corresponding to 0.55 mM of the lipid concentration were prepared.

Figure 23:
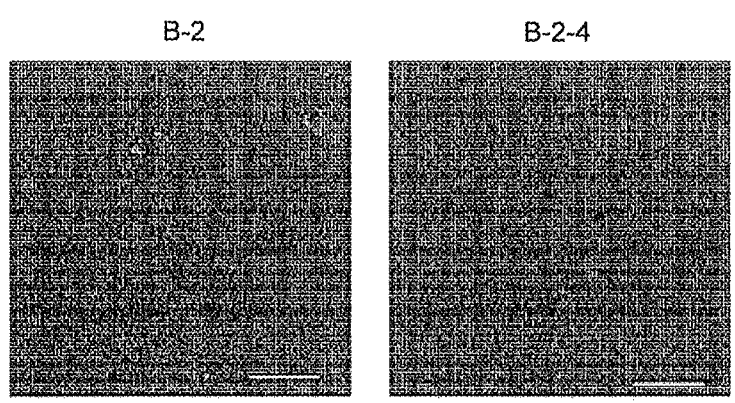
FIG. 23 presents photographs showing evaluation of the endosome amount of cells treated with various MENDs prepared from B-2 or B-2-4.

HT1080 cells were plated on a glass bottom dish at 5×10$^4$ cells/2 mL/dish 24 hr before. MEND was diluted with DMEM (FBS 10%+) to achieve pDNA 1.6 μg/2 mL and transfected into the cells. The cells without transfection of MEND were used as a control. After 5.5 hr, Lysotracker Green (Life technologies) was added at 2 μL/dish and Hoechst 33342 (Dojindo) was further added at 2 μL/dish 30 min later. 6 hr after the transfection, the cells were washed twice with heparin (20 units/mL, 2 mL), Krebs buffer (1 mL) was added, and the cells were observed by a confocal laser scan microscope. The results are shown in FIG. 23.

Endosome/lysosome and nucleus were shown in pseudo colors of green and blue, respectively. The relative endosome amount was calculated according to the following formula.

$$\text{relative endosome amont} = \frac{\text{endosome area (green pixel number)}}{\text{nucleus area (blue pixel number)}}$$

Figure 24:
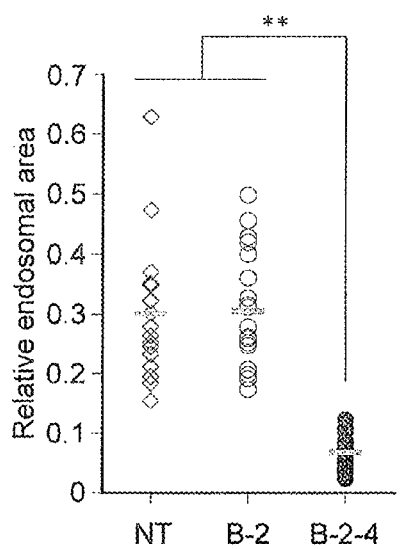
FIG. 24 is a graph showing the relative endosome amount of cells treated with various MENDs prepared from B-2 or B-2-4.

The results are shown in FIG. 24. It was clarified therefrom that the cells transfected with B-2-4 shows a significant decrease in endosome than the untreated group and the B-2 treatment group. The high endosomal escape efficiency shown in [Experimental Example 20] (1) was suggested to have been caused by an endosome destruction effect.

[Experimental Example 21]
Intracellular Kinetics (Decapsulation Efficiency)

For MEND preparation, Rhodamine-labeled pDNA prepared by the method of [Experimental Example 1] (4) was used. For preparation of MEND encapsulating the rhodamine-labeled pDNA, 50% of the pDNA solution described in [Experimental Example 1] (1) was replaced by the rhodamine-labeled pDNA. In addition, the lipid constituting the MEND was labeled with fluorescence by the method described in [Experimental Example 1] (3). MENDs having a composition of B-2-4 (Example 1):DOPE:Chol=3:3:4, B-2 (Comparative Example 2):SOPE:Chol=5:3:2 were prepared by the method described in [Experimental Example 1] (2). For the preparation, PEG$_{2000}$-DMG was used as PEG lipid, and MEND solutions corresponding to 0.55 mM of the lipid concentration were prepared.

Figure 25:
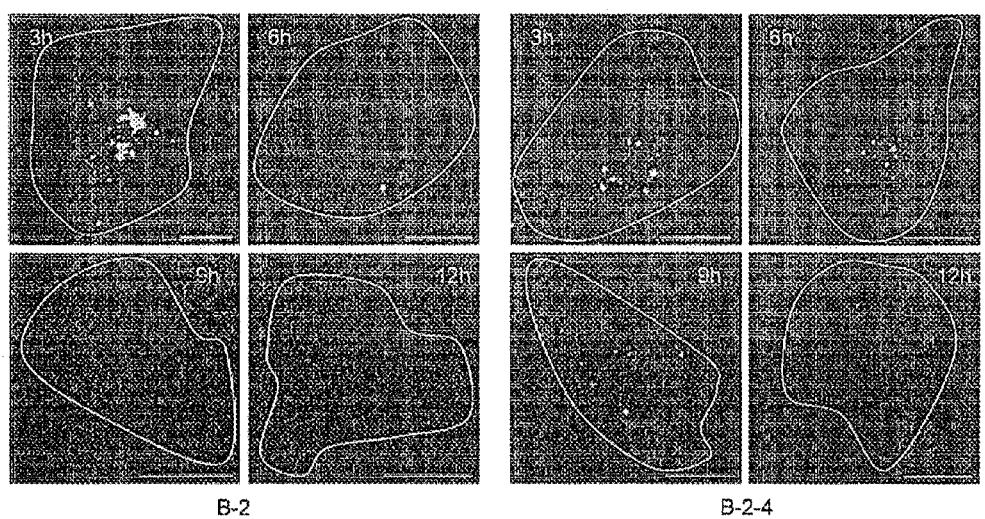
FIG. 25 presents photographs showing evaluation of the decapsulation efficiency of genes introduced by various MENDs prepared from B-2 or B-2-4.

HT1080 cells were plated on a glass bottom dish at 5×10$^4$ cells/2 mL/dish 24 hr before. MEND was diluted with DMEM (FBS 10%+) to achieve pDNA 1.6 μg/2 mL and transfected into cells. 3, 6, 9, 12 hr later, the cells were washed twice with heparin solution (20 units/mL, 2 mL), Krebs buffer (1 mL) was added, and the images at 3, 6, 9, 12 hr after the transfection were obtained by a confocal laser scan microscope. The results are shown in FIG. 25.

Rhodamine-labeled pDNA and lipid membrane of MEND were shown in pseudo colors of red and green, respectively. The decapsulation efficiency was calculated according to the following formula.

$$\text{decapsulation efficiency} = 1 - \frac{\text{amount of gene possessing lipid membrane (yellow pixel number)}}{\text{total gene amount (red pixel number)}}$$

Figure 26:
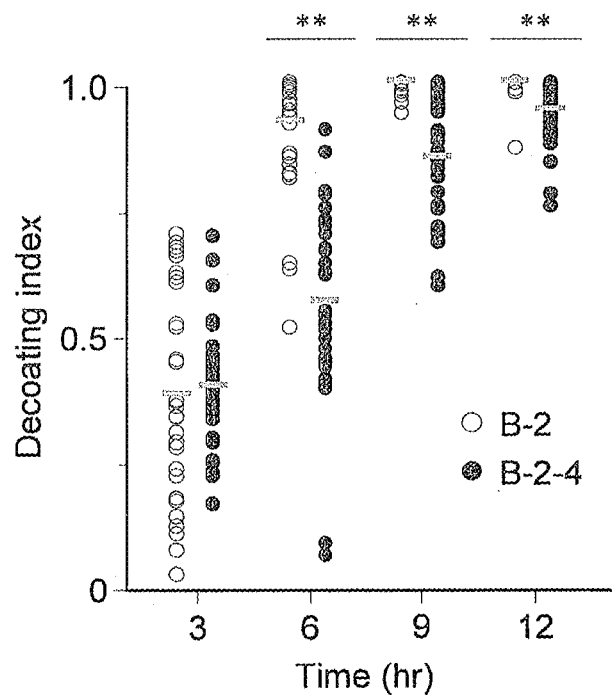
FIG. 26 is a graph showing the decapsulation efficiency of genes introduced by various MENDs prepared from B-2 or B-2-4.

The results are shown in FIG. 26. It was suggested that B-2 causes good decapsulation from early stages. It was suggested that B-2-4 causes gradual decapsulation with the passage of time.

[Experimental Example 22]
Intracellular Kinetics (Intracellular Uptake Pathway)
(1) Influence on Intracellular Uptake Amount MENDs of B-2-4 (Example 4), B-2 (Example 1) were prepared according to [Experimental Example 1] (1), (2), [Experimental Example 18]. For the preparation, PEG$_{2000}$-DMG was used as PEG lipid, and MEND solutions corresponding to 0.55 mM of the lipid concentration were prepared. pDNA was labeled with fluorescence according to the method described in [Experimental Example 15] (2).

Figure 27:
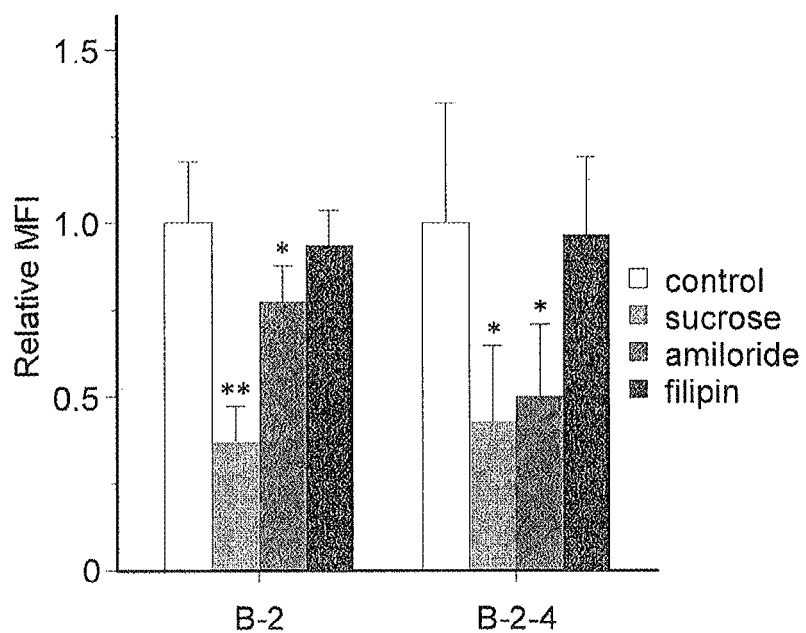
FIG. 27 is a graph showing the influence of sucrose, amiloride and filipin on the intracellular uptake of various MENDs prepared from B-2 or B-2-4.

HT1080 cells were plated on a 6-well plate at 2×10$^5$ cells/2 mL/well 24 hr before. The medium was changed to DMEM (FBS+) containing filipin at a final concentration of 10 μg/μL 30 min before transfection. The medium was changed to DMEM (FBS+) containing a final concentration of 0.3M sucrose, and 1 mM amiloride 15 min before transfection. For transfection, various MENDs were added to the dish at 1.6 μg/2 mL/dish based on the pDNA amount. 3 hr after the transfection, the intracellular pDNA amount was measured by the method described in [Experimental Example 19] (1). The results are shown in FIG. 27.

The intracellular uptake was sucrose- and amiloride-sensitive for both B-2 and B-2-4, suggesting involvement of clathrin mediated endocytosis and macropinocytosis.

(2) Influence on Gene Expression Activity

Using compositions of B-2-4 (Example 4):DOPE:Chol=3:3:4, B-2 (Example 1):SOPE:Chol=5:3:2 as lipid, MENDs were prepared according to [Experimental Example 1] (1), (2). For the preparation, PEG$_{2000}$-DMG was used as PEG lipid, and MEND solutions corresponding to 0.55 mM of the lipid concentration were prepared.

Figure 28:
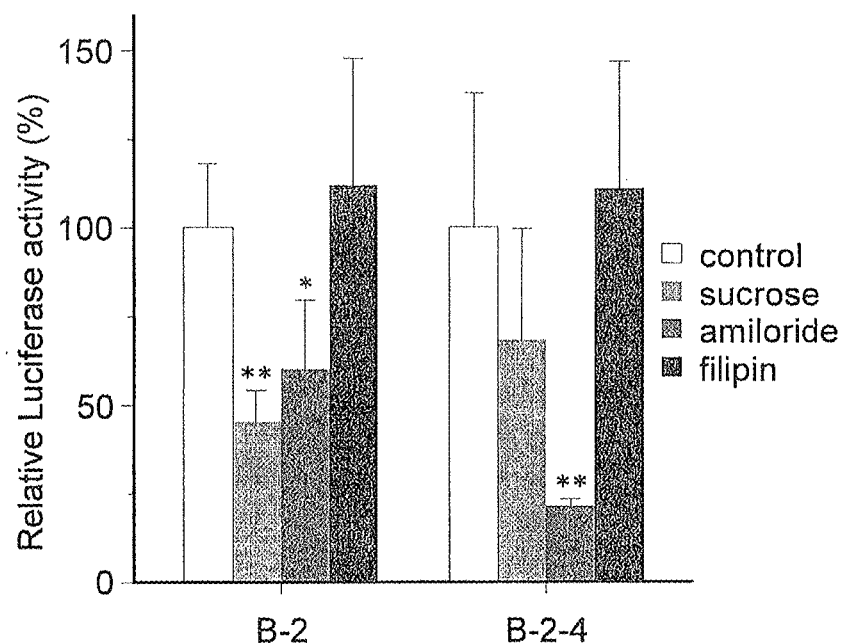
FIG. 28 is a graph showing the influence of sucrose, amiloride and filipin on the gene expression activity of various MENDs prepared from B-2 or B-2-4.

HT1080 cells were plated on a 24-well plate at 4×10$^4$ cells/500 μL/well 24 hr before. The medium was changed to DMEM (FBS+) containing filipin at a final concentration of 10 μg/μL 30 min before transfection. The medium was changed to DMEM (FBS+) containing a final concentration of 0.3M sucrose, and 1.5 mM amiloride 15 min before transfection. For transfection, various MENDs were added to the well at 0.8 μg/500 μL/well based on the pDNA amount. Thereafter, the gene expression activity was evaluated by the method described in [Experimental Example 4] (2). The results are shown in FIG. 28.

The gene expression of B-2 was inhibited by sucrose and amiloride. The gene expression of B-2-4 was inhibited by amiloride. As a result, both B-2, B-2-4 are incorporated by sucrose- and amiloride-sensitive pathway. It was suggested that an amiloride-sensitive pathway greatly contributes to the gene expression in B-2-4.

[Experimental Example 23]

Evaluation of Influence of Endosomal Acidification Inhibitor

MENDs of B-2-4 (Example 4), B-2 (Example 1) were prepared according to [Experimental Example 1] (1), (2), [Experimental Example N8]. For the preparation, $PEG_{2000}$-DMG was used as PEG lipid, and MEND solutions corresponding to 0.55 mM of the lipid concentration were prepared.

Figure 29:
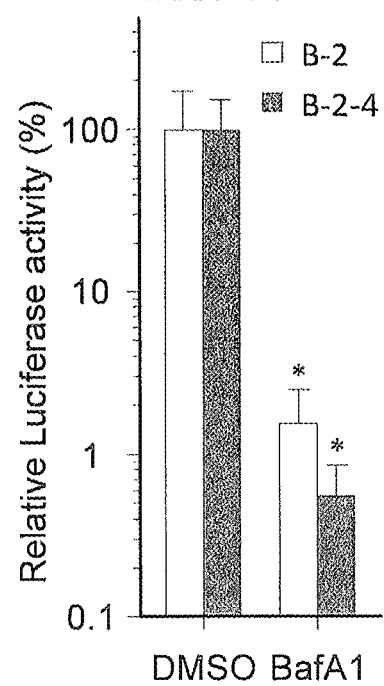
FIG. 29 is a graph showing the influence of endosomal acidification inhibition on the gene expression activity of various MENDs prepared from B-2 or B-2-4.

HT1080 cells were plated on a 3.5 cm cell culture dish at $4\times10^4$ cells/2 mL/dish 24 hr before. The medium was changed to DMEM (FBS 10%+) containing 0.5 µM BafA1 (Bafilomycin A1) 30 min before transfection. 30 min later, various MENDs were added to the dish at 1.6 µg/2 mL/dish based on the pDNA amount. 3 hr after the transfection, the medium was changed to DMEM (FBS 10%+, Phenol red free) containing a final concentration 200 µM of D-luciferin potassium. According to the Kronos Dio package insert, the luminescence amount was measured for 2 min every 20 min and taken as the luciferase activity (RLU/2 min). The results are shown in FIG. 29.

Endosomal acidification inhibition using BafA1 inhibited the activity of B-2-4 and B-2. It was suggested that B-2-4 is activated by endosomal acidification and cause gene expression.

[Experimental Example 24]

Evaluation of Inhibitory Effect by Retinoic Acid (RA)

(1) Gene Expression Inhibitory Effect

MENDs of B-2-4 (Example 4), B-2 (Example 1) were prepared according to [Experimental Example 1] (1), (2), [Experimental Example 18]. For the preparation, $PEG_{2000}$-DMG was used as PEG lipid, and MEND solutions corresponding to 0.55 mM of the lipid concentration were prepared.

HT1080 cells were plated on a 3.5 cm cell culture dish at $4\times10^4$ cells/2 mL/dish 24 hr before, various MENDs were diluted with DMEM (FBS 10%+, Phenol red free) containing a final concentration 200 µM of D-luciferin potassium and 0, 5, 7.5, 10 µM RA (sigma) to achieve 1.6 µg/2 mL/dish based on the pDNA amount and transfection was performed. According to the Kronos Dio package insert, the luminescence amount was measured for 2 min every 20 min and taken as the luciferase activity (RLU/2 min). The results are shown in FIG. 30.

Figure 30:
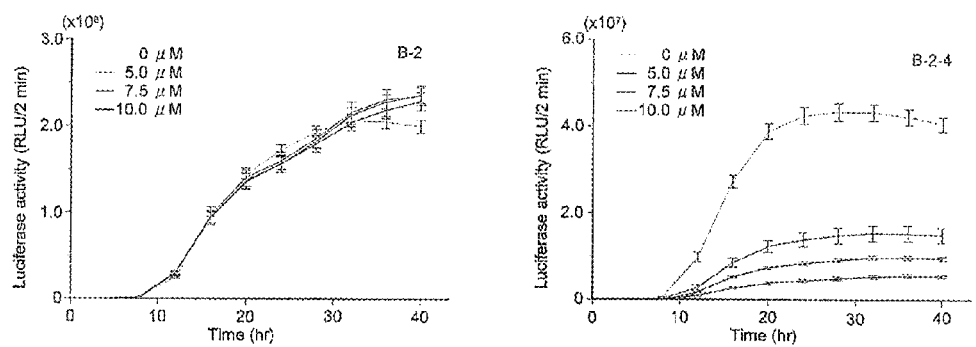
FIG. 30 presents graphs showing the influence of retinoic acid on the gene expression activity of various MENDs prepared from B-2 or B-2-4.

The gene expression activity of MEND formed from B-2-4 was decreased by RA in a concentration dependent manner (FIG. 30, right). The gene expression activity of MEND formed from B-2 was not decreased (FIG. 30, left). It was suggested that the recognition of RA is involved in the gene expression due to B-2-4.

[Experimental Example 25]

Intracellular Kinetics (Nuclear Transport)

For MEND preparation, Rhodamine-labeled pDNA prepared by the method of [Experimental Example 1] (4) was used. For preparation of MEND encapsulating the rhodamine-labeled pDNA, the pDNA solution described in [Experimental Example 1] (1) was completely replaced by rhodamine-labeled pDNA. In addition, the lipid constituting MEND was labeled with fluorescence by the method described in [Experimental Example 1] (3). MENDs having a composition of B-2-4 (Example 4):DOPE:Chol=3:3:4, B-2 (Example 1):SOPE:Chol=5:3:2 were prepared by the method described in [Experimental Example 1] (2). For the preparation, $PEG_{2000}$-DMG was used as PEG lipid, and MEND solutions corresponding to 0.55 mM of the lipid concentration were prepared.

Figure 31:
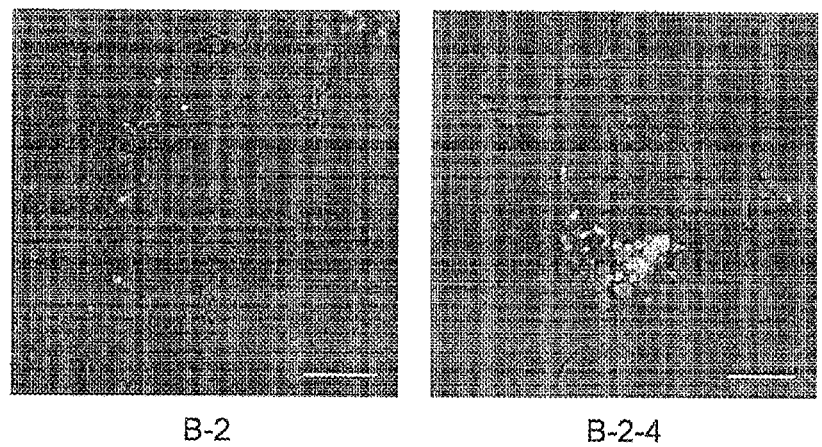
FIG. 31 presents photographs showing the intracellular kinetics of MEND prepared from B-2 and MEND prepared from B-2-4, which include rhodamine-labeled pDNA.

HT1080 cells were plated on a glass bottom dish at $5\times10^4$ cells/2 mL/dish 24 hr before. MEND was diluted with DMEM (FBS 10%+) to achieve pDNA 1.6 µg/2 mL and transfected into cells. After 3 hr, hoechst33342 (1 µL) was added and, 10 min later, the cells were washed twice with heparin solution (20 units/mL, 2 mL). Krebs buffer (1 mL) was added, and the image was obtained by a confocal laser scan microscope. The results are shown in FIG. 31.

While B-2 was diffused in the cell, B-2-4 was observed to accumulate near the nucleus. This suggests presence of a nuclear transport mechanism.

[Experimental Example 26]

Evaluation of Inhibitory Effect by GA (Ginkgolic Acid)

MENDs of B-2-4 (Example 4), B-2 (Example 1) were prepared according to [Experimental Example 16], [Experimental Example 1] (1), (2). For the preparation, $PEG_{2000}$-DMG was used as PEG lipid, and MEND solutions corresponding to 0.55 mM of the lipid concentration were prepared.

Figure 32:
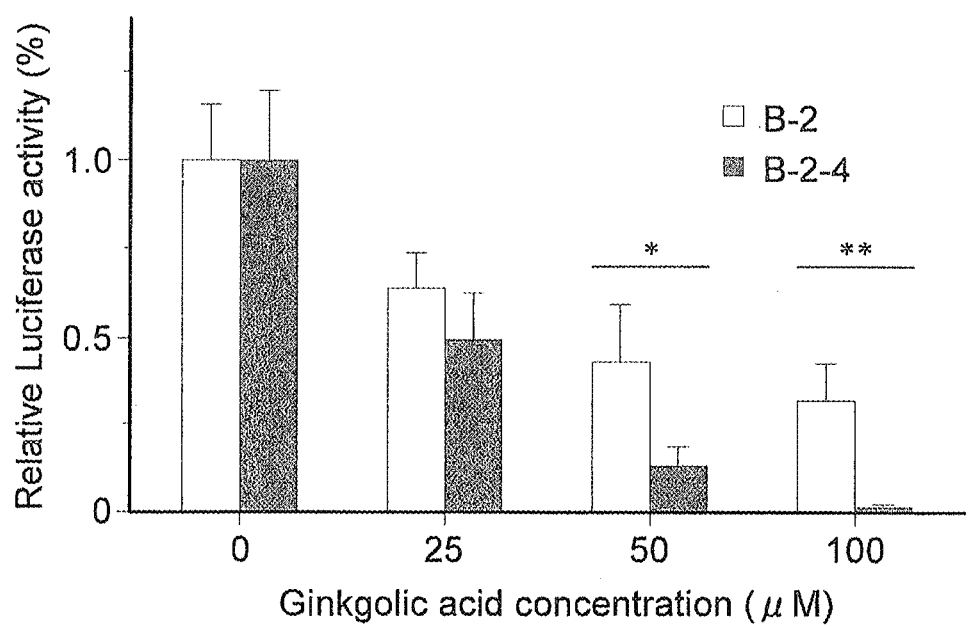
FIG. 32 is a graph showing the influence of GA on the gene expression activity of various MENDs prepared from B-2 or B-2-4.

HT1080 cells were plated on a 3.5 cm cell culture dish at $4\times10^4$ cells/2 mL/dish 24 hr before, various MENDs were diluted with DMEM (FBS 10%+, Phenol red free) containing a final concentration of 200 µM of D-luciferin potassium and 0, 25, 50, 100 µM of GA (Calbiochem) to achieve 1.6 µg/2 mL/dish based on the pDNA amount and transfection was performed. According to the Kronos Dio package insert, the luminescence amount was measured for 2 min every 20 min and taken as the luciferase activity (RLU/2 min). The results are shown in FIG. 32.

GA showed a higher inhibitory effect on B-2-4 than on B-2. GA is a small molecule that inhibits sumoylation of intracellular protein. HT1080 expresses intracellular retinoic acid binding protein II (CRABPII) that transports RA to the nucleus in a sumoylation dependent manner. The drastic decrease in the gene expression activity of B-2-4 is considered to have been caused by a decreased activity of CRABPII due to GA.

[Experimental Example 27]

Formation of Nucleic Acid Electrostatic Complex Composed of siRNA and Protamine

A siRNA solution and protamine (CALBIOCHEM) solution were diluted with 10 mM HEPES buffer (pH 5.3) to 0.3 mg/mL and 0.2 mg/mL, respectively. While stirring 0.3 mg/mL siRNA solution (250 µL), 0.2 mg/mL protamine solution (250 µL) was added dropwise in small portions to prepared an electrostatic complex of siRNA and protamine (N/P ratio=1.0) as a core of the vector.

As a siRNA sequence for Factor VII (FVII), one described in Akinc et al, Molecular Therapy, 17(5) 872-879 (2009), which was free of chemical modification, was used.

[Experimental Example 28]

Preparation of siRNA-Encapsulated MEND by Ethanol Dilution Method

A lipid solution in ethanol was mixed at a ratio of B-2:SOPE:Chol=5:3:2 for B-2 MEND (Example 1), at a ratio of B-2-4:DOPE:Chol=3:3:4 for B-2-4 MEND (Example 4), and at a ratio of B-2-5:POPE:Chol=3:4:3 for B-2-5 MEND (Example 5), to a total lipid of 660 nmol in a 5 mL tube. Further, PEG2000-DMG was added as PEG lipid in an amount equivalent to 3 mol % of the total lipid, and ethanol was added to a total volume of 400 µL each. While stirring the lipid solution by a vortex mixer, a solution (400 µL) of a nucleic acid electrostatic complex composed of siRNA/protamine prepared in [Experimental Example 27] was mixed, then 10 mM HEPES buffer (pH 5.3, 2.4 mL) was quickly added, and the mixture was vigorously stirred. The mixture was subjected to centrifugal ultrafiltration using Amicon Ultra-15 100K device (Millipore) at 1000 g, 10 min, 30° C. The mixture was sufficiently diluted with 10 mM HEPES buffer (pH 7.4), and again subjected to centrifugal ultrafiltration. This solution was adjusted to an object lipid concentration with 10 mM HEPES buffer (pH 7.4).

[Experimental Example 29]
Measurement of Particle Size and Surface Potential of siRNA-Encapsulated MEND The particle size and surface potential were measured using the dynamic light scattering method (Zetasizer Nano; Malvern). The particle size and surface potential of various MENDs prepared by the preparation method of [Experimental Example 28] are shown in Table 5. They all showed a weak negative charge at physiological pH.

TABLE 5

|  | size (nm) | PDI | zeta (mV) |
|---|---|---|---|
| B-2 (Example 1) | 186 | 0.07 | −1.7 |
| B-2-4 (Example 4) | 186 | 0.11 | −5.1 |
| B-2-5 (Example 5) | 218 | 0.13 | −9.1 |

[Experimental Example 30]
Knockdown Effect of siRNA-Encapsulated MEND

Figure 33:
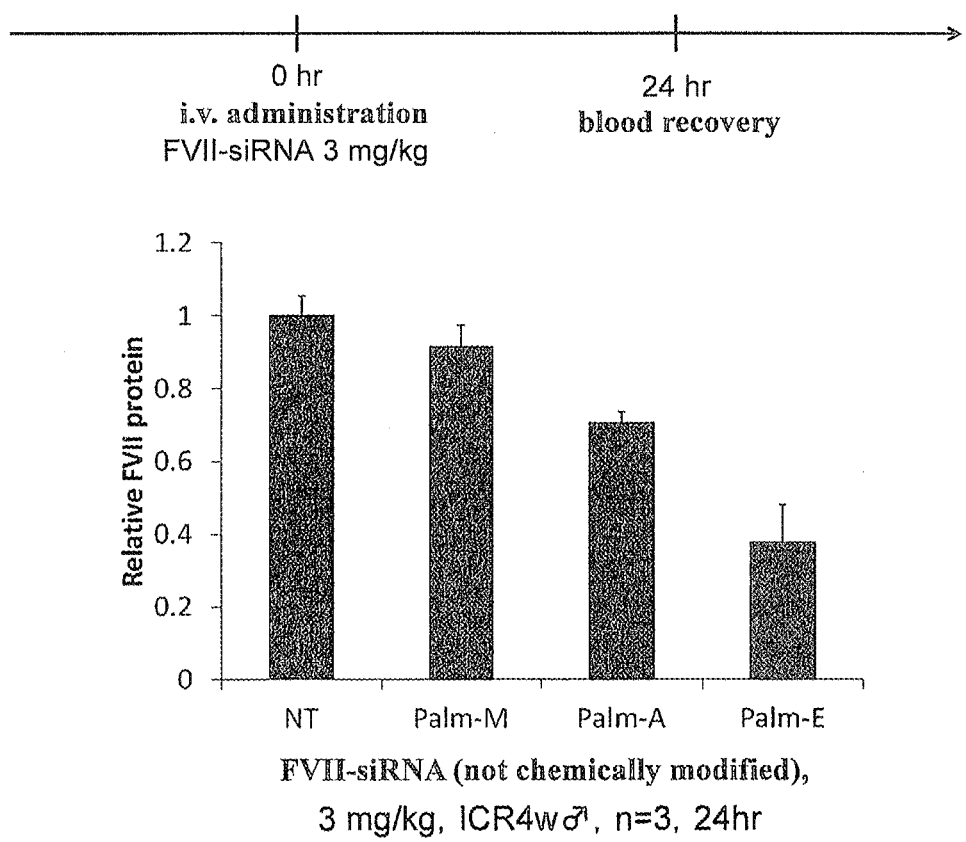
FIG. 33 is a graph showing the effect of introduction of siRNA against FVII by various MENDs prepared from B-2, B-2-4 or B-2-5.

A MEND solution prepared by the method shown in [Experimental Example 28] was administered to 4-week-old male ICR mice at 3 mg siRNA/kg from the tail vein, and blood was collected 24 hr later. This blood sample was centrifuged at 1000 g, 10 min, 4° C., and the supernatant was recovered to obtain plasma. The amount of Factor VII (FVII) in the plasma was quantified by BIOPHEN FVII CHROMOGENIC ASSAY (HYPHEN BioMed). The results are shown in FIG. 33. All of B-2, B-2-4, B-2-5 showed a decrease in the FVII expression level as compared to the non-treatment group. Among them, B-2-5 MEND showed the greatest knockdown effect.

Figure 34:
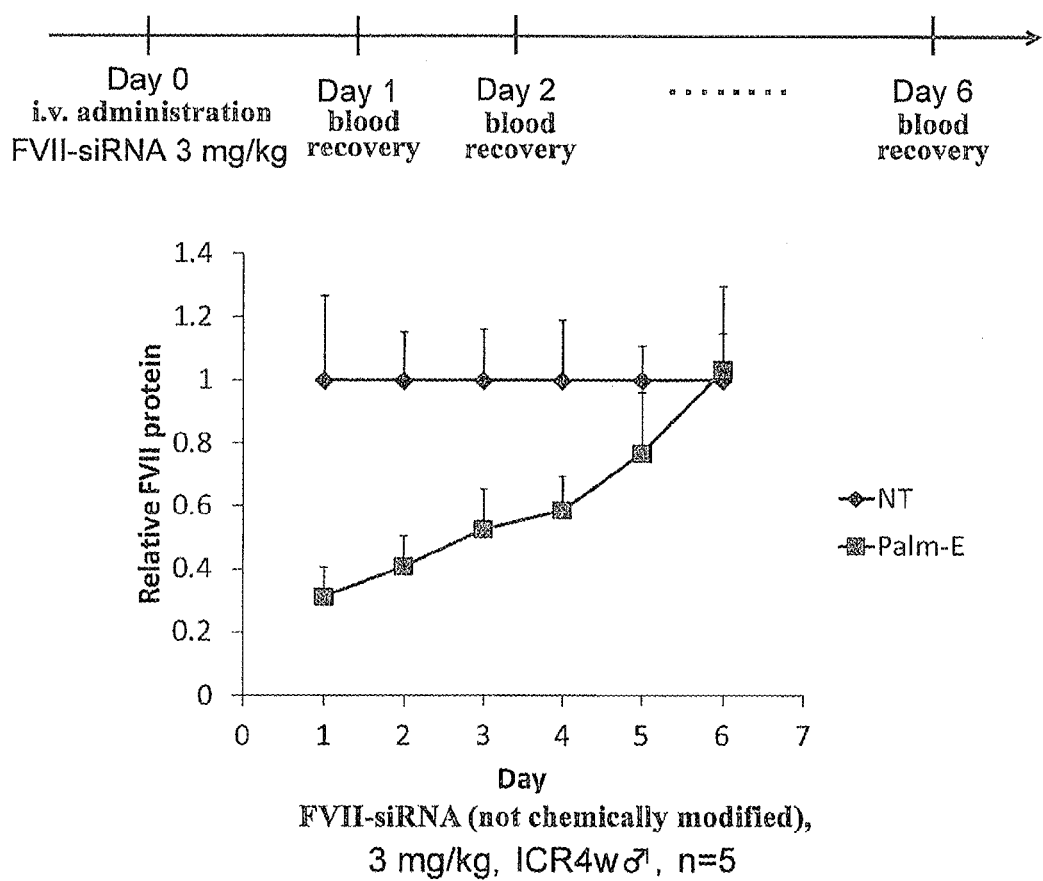
FIG. 34 is a graph evaluating the sustainability of gene knockdown effect of siRNA against FVII introduced by various MENDs prepared from B-2-5.

[Experimental Example 31]
Evaluation of Sustainability of siRNA-Encapsulated MEND A MEND solution prepared by the method shown in [Experimental Example 28] was administered to 4-week-old male ICR mice at 3 mg siRNA/kg from the tail vein, and blood was collected sequentially every 24 hr from the tail vein up to day 6 from the administration to follow the expression level of FVII over, time. The results are shown in FIG. 34.

It was clarified that the gene knockdown effect reaches a peak one day after the administration, and thereafter gradually disappears in about 7 weeks.

[Experimental Example 32]
Preparation of MEND by t-BuOH Injecting Method

A lipid solution in t-BuOH with a composition of cationic lipid/cholesterol=70/30, DMG-PEG2000 3% and a total lipid amount of 3000 nmol/400 µL (7.5 mM) was prepared in a 1.7 mL tube. In a separate 1.7 mL tube, an siRNA solution was prepared by mixing an siRNA aqueous solution containing siRNA (160 µg) and 20 mM malate buffer (pH 4.00, 30 mM NaCl) to total 50 µL. With vigorous stirring of the lipid solution, the siRNA solution was gradually added dropwise, and the mixed solution was taken in a 1 mL syringe. Then, 20 mM malate buffer (pH 4.00, 30 mM NaCl, 2 mL) was added into a 5 mL tube, and the mixed solution was gradually injected with vigorous stirring. Thereafter, the mixture was further diluted with PBS (7 mL) and centrifuged at 1000 g, 30° C. for 10 min in Amicon Ultra-15-100K to a volume of less than 1.5 mL. PBS (15 mL) was added, and the solution was centrifuged again to about 500-1000 µL. Finally, the MEND solution was adjusted by diluting with PBS to the object lipid concentration.

The particle size and surface potential of various MENDs were measured according to the method described in [Experimental Example 2] and the results are shown in Table 6. MENDs prepared using the compounds of Examples 5-14 showed a weak negative charge at physiological pH, and a MEND prepared using the compound of Example 15 showed a weak positive charge at physiological pH.

TABLE 6

|  | Size (nm) | PDI | Zeta (mV) |
|---|---|---|---|
| B-2-5 (Example 5) | 110 | 0.076 | −9.5 |
| TS-C4E (Example 6) | 118 | 0.07 | −9.8 |
| TS-C5P (Example 7) | 125 | 0.13 | −6.4 |
| TS-P2C1 (Example 8) | 114 | 0.12 | −12.2 |
| TS-P3C1 (Example 9) | 118 | 0.13 | −9.8 |
| TS-P4C1 (Example 10) | 113 | 0.13 | −11.9 |
| TS-P4C2 (Example 11) | 125 | 0.07 | −8.5 |
| TS-P4C3 (Example 12) | 123 | 0.09 | −6.6 |
| TS-P4C4 (Example 13) | 123 | 0.11 | −6.9 |
| TG-C3M (Example 14) | 120 | 0.13 | −13.0 |
| TSamide-C3M (Example 15) | 93 | 0.21 | 7.0 |

[Experimental Example 33]
Knockdown Effect of siRNA-Encapsulated MEND

Figure 35:
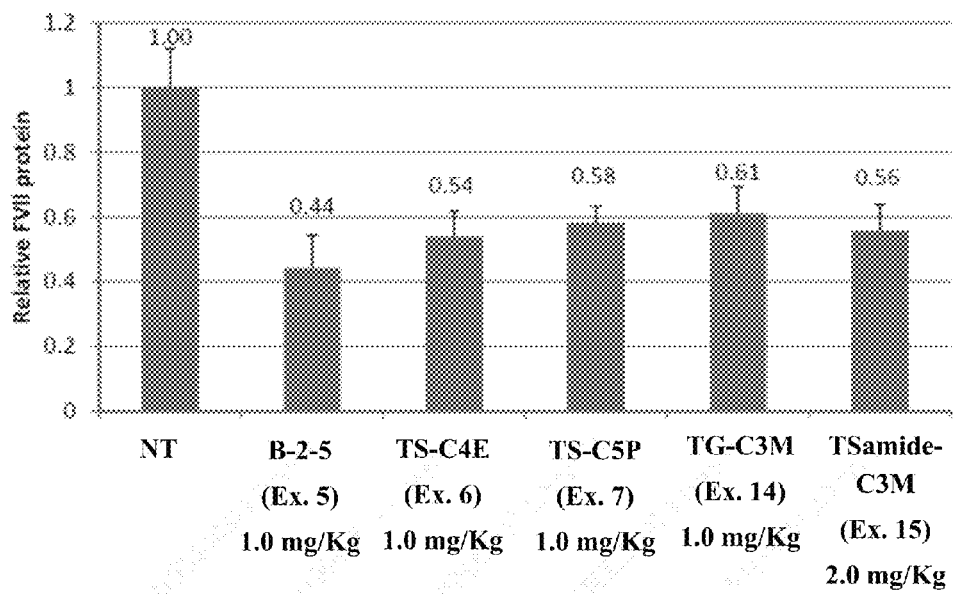
FIG. 35 is a graph showing the effect of introduction of siRNA against FVII by various MENDs prepared from B-2-5, TS-C4E, TS-C5P, TG-C3M or TSamide-C3M.
Figure 36:
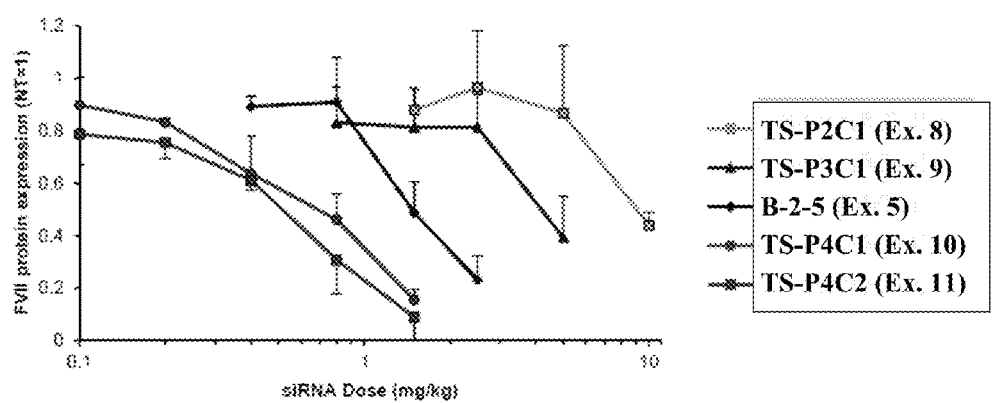
FIG. 36 is a graph showing the effect of introduction of siRNA against FVII by various MENDs prepared from TS-P2C1, TS-P3C1, B-2-5, TS-P4C1 or TS-P4C2.
Figure 37:
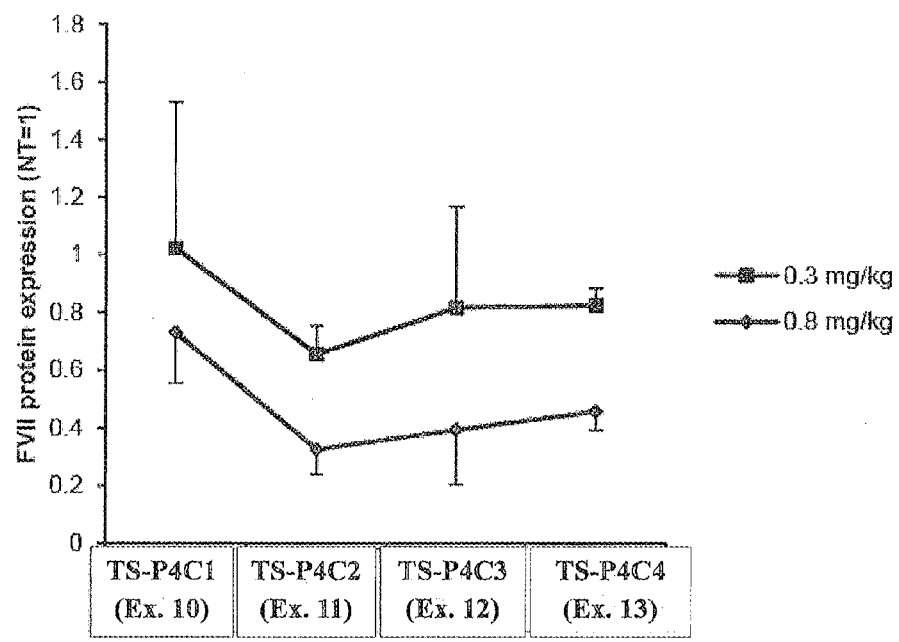
FIG. 37 is a graph showing the effect of introduction of siRNA against FVII by various MENDs prepared from TS-P4C1, TS-P4C2, TS-P4C3 or TS-P4C4.

MENDs prepared by the method shown in Experimental Example 32 were administered by a method similar to the method shown in Experimental Example 30 with varying doses of siRNA, and the knockdown effect was evaluated. The results are shown in FIG. 35, FIG. 36, and FIG. 37. As compared to non-treatment group, all MENDs prepared using the compounds of Examples 5-15 showed a decrease in the FVII expression level. Among them, MENDs prepared using the compounds of Examples 10, 11, 12 and 13 showed the highest knockdown effect.

Figure 38:
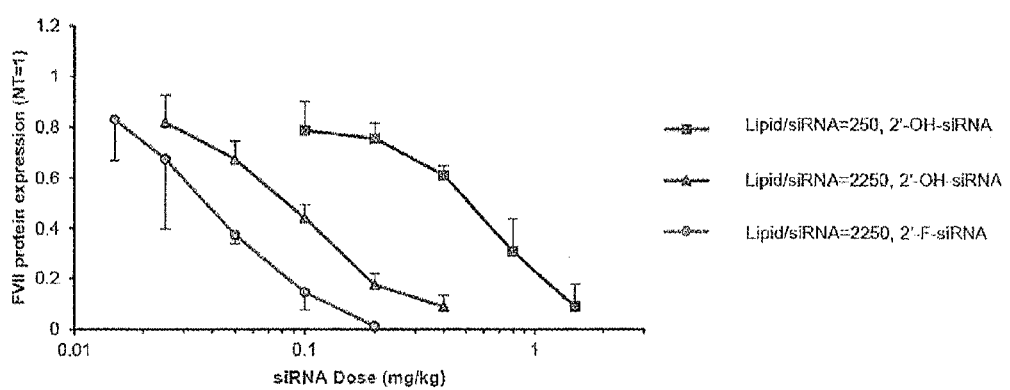
FIG. 38 is a graph showing the effect of chemical modification of siRNA on the knockdown effect of siRNA.

[Experimental Example 34]
Knockdown Effect of Chemically-Modified siRNA-Encapsulated MEND A MEND (Lipid/siRNA ratio=250) prepared using the compound of Example 13 and by the method shown in Experimental Example 32, and a MEND having the ratio of lipid and siRNA of Lipid/siRNA ratio=2250 were prepared. Furthermore, of Lipid/siRNA ratio=2250, MENDs wherein siRNA was replaced by chemically-modified one (2'-F) were prepared, and the knockdown effect was evaluated by the method shown in Experimental Example 33. The results are shown in FIG. 38. By setting Lipid/siRNA ratio to 2250, the knockdown effect was enhanced, and use of chemically-modified siRNA further enhanced the knockdown effect.

INDUSTRIAL APPLICABILITY

According to the present invention, since nucleic acid can be intracellularly introduced with high efficiency, it is useful for gene therapy and biochemical experiments.

The invention claimed is:

1. A compound represented by the formula (1)

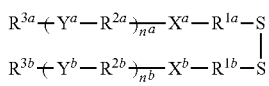 (1)

wherein $X^a$ and $X^b$ are each independently $X^1$ or $X^2$;

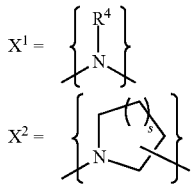

s is 1 or 2,
$R^4$ is an alkyl group having 1-6 carbon atoms,
$n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each independently —CO—O— or —CO—NH—, and
$R^{3a}$ and $R^{3b}$ are each independently a sterol residue, a liposoluble vitamin residue or an aliphatic hydrocarbon group having 12-22 carbon atoms,
wherein the sterol residue is a cholesteryl group, cholestaryl group, stigmasteryl group, β-sitosteryl group, or a lanosteryl group,
wherein the liposoluble vitamin residue is a group obtained by replacing a hydroxyl group or carboxyl group in the liposoluble vitamin with a bond, —O—CO—CH$_2$—CH$_2$— or —O—CO—CH$_2$—CH$_2$—CH$_2$—, and
wherein the liposoluble vitamin is retinoic acid, retinol, ergosterol, 7-dehydrocholesterol, calciferol, cholecalciferol, dihydroergocalciferol, dihydrotachysterol, tocopherol, or tocotrienol.

2. The compound of claim 1, wherein $X^a$ and $X^b$ are each independently $X^1$.

3. The compound of claim 1, wherein $X^a$ and $X^b$ are each independently $X^2$.

4. The compound of claim 1, wherein $R^{3a}$ and $R^{3b}$ are each independently a liposoluble vitamin residue or an aliphatic hydrocarbon group having 12-22 carbon atoms.

5. The compound of claim 1, wherein $R^{3a}$ and $R^{3b}$ are each independently a liposoluble vitamin residue.

6. The compound of claim 1, wherein $R^{3a}$ and $R^{3b}$ are each independently an aliphatic hydrocarbon group having 12-22 carbon atoms.

7. A lipid membrane structure comprising the compound of claim 1 as a membrane-constituting lipid.

8. An agent for introducing a nucleic acid, comprising the compound of claim 1 or a lipid membrane structure comprising the compound as a membrane-constituting lipid.

9. A method of introducing a nucleic acid into a cell, comprising encapsulating the nucleic acid with the lipid membrane structure of claim 7 and contacting the cell with the encapsulated nucleic acid.

10. A method of introducing a nucleic acid into a cell, comprising encapsulating the nucleic acid with the lipid membrane structure of claim 7, and administering the encapsulated nucleic acid to a living organism to deliver the nucleic acid to the cell.

11. The compound of claim 2, wherein $R^{3a}$ and $R^{3b}$ are each independently a liposoluble vitamin residue.

12. The compound of claim 2, wherein $R^{3a}$ and $R^{3b}$ are each independently an aliphatic hydrocarbon group having 12-22 carbon atoms.

13. The compound of claim 3, wherein $R^{3a}$ and $R^{3b}$ are each independently a liposoluble vitamin residue.

14. The compound of claim 3, wherein $R^{3a}$ and $R^{3b}$ are each independently an aliphatic hydrocarbon group having 12-22 carbon atoms.

15. A lipid membrane structure comprising the compound of claim 2 as a membrane-constituting lipid.

16. A lipid membrane structure comprising the compound of claim 3 as a membrane-constituting lipid.

17. A method of introducing a nucleic acid into a cell, comprising encapsulating the nucleic acid with the lipid membrane structure of claim 15 and contacting the cell with the encapsulated nucleic acid.

18. A method of introducing a nucleic acid into a cell, comprising encapsulating the nucleic acid with the lipid membrane structure of claim 15, and administering the encapsulated nucleic acid to a living organism to deliver the nucleic acid to the cell.

19. A method of introducing a nucleic acid into a cell, comprising encapsulating the nucleic acid with the lipid membrane structure of claim 16 and contacting the cell with the encapsulated nucleic acid.

20. A method of introducing a nucleic acid into a cell, comprising encapsulating the nucleic acid with the lipid membrane structure of claim 16, and administering the encapsulated nucleic acid to a living organism to deliver the nucleic acid to the cell.

* * * * *